US005821111A

United States Patent [19]
Grady et al.

[11] Patent Number: 5,821,111
[45] Date of Patent: Oct. 13, 1998

[54] BIOCONVERSION OF WASTE BIOMASS TO USEFUL PRODUCTS

[75] Inventors: James L. Grady; Guang Jiong Chen, both of Fayetteville, Ark.

[73] Assignee: Bioengineering Resources, Inc., Fayetteville, Ark.

[21] Appl. No.: 808,088

[22] Filed: Feb. 28, 1997

Related U.S. Application Data

[63] Continuation of Ser. No. 220,686, Mar. 31, 1994, abandoned.

[51] Int. Cl.$^6$ ............................... C12P 1/04; C12P 3/00; C12N 1/20
[52] U.S. Cl. ...................... 435/252.5; 435/135; 435/139; 435/140; 435/168; 435/832
[58] Field of Search .................................. 435/168, 252.5, 435/139, 135, 140, 832

[56] References Cited

U.S. PATENT DOCUMENTS

| | | | |
|---|---|---|---|
| 4,497,637 | 2/1985 | Purdy et al. | 48/111 |
| 4,515,759 | 5/1985 | Burnes et al. | 423/220 |
| 4,553,981 | 11/1985 | Fuderer | 48/62 |
| 4,568,644 | 2/1986 | Wang et al. | 435/161 |
| 4,652,526 | 3/1987 | Hsu | 435/253 |
| 4,692,172 | 9/1987 | Stellaccio et al. | 48/197 |
| 4,721,676 | 1/1988 | Zeikus | 435/253 |
| 4,732,855 | 3/1988 | Zeikus et al. | 435/141 |
| 4,771,001 | 9/1988 | Bailey et al. | 435/139 |
| 4,919,813 | 4/1990 | Weaver | 210/603 |
| 4,921,799 | 5/1990 | Kitaura et al. | 435/167 |
| 4,935,360 | 6/1990 | Klemps et al. | 435/140 |
| 4,994,093 | 2/1991 | Wetzel et al. | 48/197 |
| 5,026,647 | 6/1991 | Tomes et al. | 435/244 |
| 5,036,005 | 7/1991 | Tedder | 435/161 |
| 5,059,288 | 10/1991 | Curry | 203/43 |
| 5,077,208 | 12/1991 | Sublette | 435/168 |
| 5,110,319 | 5/1992 | Turpin et al. | 44/451 |
| 5,134,944 | 8/1992 | Keller et al. | 110/234 |
| 5,173,429 | 12/1992 | Gaddy | 435/163 |
| 5,238,469 | 8/1993 | Briesacher et al. | 95/115 |
| 5,593,886 | 1/1997 | Gaddy | 435/252.7 |

FOREIGN PATENT DOCUMENTS

| | | | |
|---|---|---|---|
| 0282750 | 9/1988 | European Pat. Off. | 435/266 |
| 282750A | 10/1987 | Germany . | |

OTHER PUBLICATIONS

Photoproduction of Molecular Hydrogen by *Rhodospirillum Rubrum*, Howard Gest and Martin D. Kamen, Science, Jun. 3, 1949, vol. 109, pp. 558–559.
Proton Translocation Coupled to the Oxidation of Carbon Monoxide to $CO_2$ and $H_2$ in *Methanosarcina Barkeri* Michael Bott and Rudolf K. Thauer, pp. 469–472, 1989.
Identification of a Carbon Monoxide–Metabolizing Bacterium as a Strain of *Rhodopseudomonas Geletinosa* (Molisch) van Niel, M.P. Dashekvicz and R.L. Uffen, International Journal of Systematic Bacteriology, Apr. 1979, pp. 145–148.

Carbon Monoxide Fixation Into the Carboxyl Group of Acetate During Growth of *Acetobacterium Woodii* and $H_2$ and $CO_2$, Gabriele Diekert and Maria Ritter, FEMS Microbiology Letters 17 (1983), pp. 299–302.
Photosynthetic Carbon Metabolism in the Green and Purple Bacteria, R. C. Fuller, Chapter 36, pp. 691–705, 1978.
Sulfinol Process Has Several Key Advantages, B. Gene Goar, The Oil and Gas Journal, Jun. 30, 1969, pp. 117–120.
Oxidation of Hydrogen and Reduction of Methanol to Methane is the Sole Energy Source for a Methanogen Isolated from Human Feces, Terry L. Miller and M.J. Wolin, Journal of Bacteriology, Feb. 1983, pp. 1051–1055.
Association of Hydrogen Metabolism with Unitrophic or Mixotrophic Growth of *Methanosarcina barkeri* in Carbon Monoxide, Jill M. O'Brien et al., Journal of Bacteriology, Apr. 1984, pp. 373–375.
Fuel Gas from Municipal Waste in an Integrated Circulating Fluid–Bed Gasification/Gas–Cleaning Process, Erik Rensfelt et al., 1988.
Carbon Monoxide Fixation into the Carboxyl Group of Acetyl Coenzyme A During Autotrophic Growth fo Methanobacterium, E. Stuperich et al., FEBS Letters, Vol. 152, No. 1, pp. 21–23, Feb. 1983.
Mutants of *Rhodospirillum rubrum* Obtained After Long–Term Anaerobic, Dark Growth, R.L. Uffen et al., Journal of Bacteriology, Dec. 1971, pp. 1348–1356.
Anaerobic Growth of a Rhodopseudomonas Species in the Dark With Carbon Monoxide as Sole Carbon and Energy Substrate, Robert L. Uffen, Proc. Natl. Acad. Sci. USA, vol. 73, No. 9, pp. 3298–3302, Sep. 1976.
Hydrogenase, Nitrogenase, and Hydrogen Metabolism in the Photosynthetic Bacteria, Paulette M. Vignais et al., Advances in Microbial Physiology vol. 26, pp. 155–234, 1985.
Demain et al., "Industrial Microbiology and Biotechnology", AJM 1986, pp. 332–335.
Crueger & Crueger, "Biotechnology: A Textbook of Industrial Microbiology", 2d Ed., Sinauer Assoc., Inc., pp. 74–89.

(List continued on next page.)

Primary Examiner—Herbert J. Lilling
Attorney, Agent, or Firm—Howson and Howson

[57] ABSTRACT

A process is provided for converting waste biomass to useful products by gasifying the biomass to produce synthesis gas and converting the synthesis gas substrate to one or more useful products. The present invention is directed to the conversion of biomass wastes including municipal solid waste, sewage sludge, plastic, tires, agricultural residues and the like, as well as coal, to useful products such as hydrogen, ethanol and acetic acid. The overall process includes the steps of gasifying the waste biomass to produce raw synthesis gas, cooling the synthesis gas, converting the synthesis gas to the desired product or products using anaerobic bioconversion, and then recovering the product or products. In accordance with a particular embodiment of the present invention, waste biomass is converted to synthesis gas containing carbon monoxide and, then, the carbon monoxide is converted to hydrogen by an anaerobic microorganism ERIH2, *bacillus smithii* ATCC No. 55404.

7 Claims, 42 Drawing Sheets

OTHER PUBLICATIONS

Biotechnology Company Set for Fayetteville, Patricia May, Springsdale Morning News, Oct. 29, 1992, p. 1A.

Industrial Innovations for Tomorrow, New Process Uses Bacteria To Transform Waste Gases Into Useful Chemicals, U.S. Dept, of Energy Publication Aug. 1992.

The Production of Acetic Acid From Carbon Dioxide and Hydrogen by an Anaerobic Bacterium, Tsuyoshi Morinaga and Naoki Kawada, Journal of Biotechnology, 14 (1990). 187–194.

Biological Conversion of Coal Synthesis Gas to Methane; S. Barik et al., Energy Progress, Vol. 7, No. 3, Sep., 1987, pp. 157–160.

Chemical and Fuel Production by Anaerobic Bacteria J.G. Zeikus, Annual Review Microbiology, 1980, pp. 423–464.

Energy From Biomass and Wastes, H. Alden, E. Bjorkman, B.Espenas, L. Waldheim, IGT, Mar. 1991.

Gas–Solid Pyrolysis of Tire Wastes—Kinetics and Material Balances of Batch Pyrolysis of Used Tires, J. M. Bouvier, F. Charbel and M. Gelus, Resources and Conservation, 1987, vol. 15, pp. 205–214.

Fermentation as an Advantageous Route for the Production of an Acetate Salt for Roadway De–Icing, C. W. Marynowski, J. L. Jones, D. Tuse, and R. L. Boughton, American Chemical Society, 1985, vol. 24, pp. 457–465.

Photosynthetic Carbon Metabolism in the Green and Purple Bacteria, "The Photosynthetic Bacteria", ed. by R. K. Clayton and W. R. Sistrom, Plemun Press, New York, pp. 691–705 (1978).

Biomethanation of Biomass Pyrolysis Gases, C.A. Tracey and E. Ashare, Solar Energy Research Institute, Jun. 1981, pp. 1–148.

Bioconversion of Synthesis Gas Into Liquid of Gaseous Fuels, K.T. Klasson, M.D. Ackerson, E.C. Clausen and J.L. Gaddy, Enzyme Microbiology Technology Aug. 1992, vol. 14, pp. 602–608.

Production of Acetic Acid by Actogenium Kivui, R. klemps, S.M. Schoberth, H. Sahm, Applied Microbiology and Biotechnology, 1987, pp. 229–234.

Mechanism of Acetate Synthesis from $CO_2$ by Clostridium Acidiurici, L.J. Waber and H.G. Wood, Journal Bacteriology, Nov. 1979, vol. 140, pp. 468–478.

Hydrogenase. Nitrogenase, and Hydrogen Metabolism in the Photosynthetic Bacteria, P.M. Vignais, A. Colbeau, J.C. Willison, Y. Jouanneau, Advances in Microbial Physiology, vol. 26, 1985, pp. 163–177.

Photoproduction of Molecular Hydrogen by *Rhodopirillum Rubrum*, H. Gest and M.D. Kamen, Science Jun. 3, 1949, vol. 109, pp. 558–559.

A Comparative Study of the Light and Dark Fermentations of Organic Acids By *Rhodospirillum Rubrum*, E. f. Kohlmiller, Jr., and H. Gest, Department of Microbiology, School of Medicine, Western Reserve University, Cleveland 6, Ohio, Dec. 5, 1950, vol. 61, pp. 269–282.

Carbon Monoxide Fixation Into the Carboxyl Group of Acetate During Growth of *Acetobacterium Woodii* on $H_2$ and $CO_2$, G. Diekert and M. Ritter, Federation of European Microbiological Societies, Microbiology Letters, 17 (1983) pp. 299–302.

Isolation From Soil and Properties of the Extreme Thermophile Clostridium Thermohydrosulfuricum, Jurgen Wiegel et al, Journal of Bacteriology, Sep. 1979, pp. 800–810.

Solvent Equilibria of Carboxylic Acids from Water, James M. Wardell and C. Judson King, Journal of Chemical and Engineering Data, vol. 23, No. 2, 1978, pp. 144–148.

Removing Carboxylic Acids From Aqueous Wastes, CEP, May 1977 R. W. Helsel, Hydroscience Environmental Systems, Knoxville, TN.

Acetogenium Kivui, A New Thermophilic Hydrogenoxidizing, Acetogenic Bacterium, J.A. Leigh et al, Arch. Microbiol., 129:275–280.

Sporomusa, A New Genus of Gram–Negative Anaerobic Bacteria Including *Sporomusa Sphaeroides* Spec. Nov. and Sporomusa Ovata Spec. Nov., Moller et al, Arch Microbiology (1984) 139:388–396.

Acetobacterium, A New Genus of Hydrogen–Oxidizing, Carbon Dioxide–Reducing, Anaerobic Bacteria, Balch et al, International Journal of Systematic Bacteriology, Oct. 1977, pp. 355–361.

Peptostreptococcus Products Strain That Grows Rapidly with CO as the Energy Source, William H. Lorowitz and Marvin P. Bryant, Applied and Environmental Microbiology, May 1984, pp. 70–74.

Growth of *Eubacterium Limosum* with Carbon Monoxide as the Energy Source, B.R. Sharak Genthner and M.P. Bryant, Applied and Environmental Microbiology, Jan. 1982, pp. 70–74.

Carbon Monoxide Metabolism of the Methylotrophic Acidogen *Butyribacterium Methylotrophicum*, Lee Lynd R. Kerby and J.G. Zeikus, Journal of Bacteriology, Jan. 1982, pp. 255–263.

Revival of the Name *Clostridium Aceticum*, Gerhard Gottschalk and Manfred Braun, International Journal of Systematic Bacteriology, Oct. 1981, p. 476.

Hydrogen Utilization by Clostridia in Sewage Sludge, Kyoko Ohwaki and R.E. Hungate, Applied and Environmental Microbiology, Jun. 1977, pp. 1270–1274.

Single–Carbon Catabolism in Acetogens: Analysis of Carbon Flow in *Acetobacterium Woodii* and *Butyribacterium Methylotrophicum* by Fermentation and $^{14}C$ Nuclear Magnetic Resonance Measurement, R. Kerby et al, Journal of Bacteriology, Sep. 1983, pp. 1208–1218.

Production of Acetic Acid by *Clostridium Thermoaceticum* in Batch and Continuous Fermentations, K. Sugaya et al, Biotechnology and Bioengineering, vol. XXVIII, (1986), pp. 678–683.

Isolation of a Strain of *Clostridium Thermoaceticum* Capable of Growth and Production at Ph 4.5, Robert D. Schwartz and Frederick A. Keller Jr., Aplied and Environmental Microbiology, Jan. 1982, pp. 117–123.

Acetic Acid Production by *Clostridium Thermoaceticum* in Ph–Controlled Batch Fermentations at Acidic pH, Robert D. Schwartz and Frederick A. Keller Jr., Applied and Environmental Microbiology, Jun. 1982, pp. 1385–1392.

Characterization of the $H_2$—and Co–Dependent Chemolithotrophic Potentials of the Acetogens *Clostridium Thermoaceticum* and *Acetogenium Kivui*, Steven L. Daniel et al, Journal of Bacteriology, Aug. 1990, pp. 4464–4471.

*Clostridium Thermosaccharolyticum* Strain Deficient in Acetate Production, David M. Rothstein, Journal of Bacteriology, Jan. 1986, pp. 319–320.

Nickel Transport by the Thermophilic Acetogen *Acetogenium Kivui*, Applied and Environmental Microbiology, May 1989, pp. 1078–1081.

Differential Effects of Sodium on Hydrogen– and Glucose–Dependent Growth of the Acetogenic Bacterium *Acetogenium Kivui*, Hsuichih Yang and Harold L. Drake, Applied and Environmental Microbiology, Jan. 1990, pp. 81–86.

Influence of Environmental Factors in the Production of R(–)–1,2–Propanediol by *Clostridium Thermosaccharolyticum*, F. Sanchez–Riera et al, Biotechnology Letters, vol. 9, No. 7, pp. 449–454.

Analysis if Hydrogen Metabolism in Methanosarcina Barkeri: Regulation of Hdrogenase and Role of Co–Dehydrogenase in $H_2$ Production, L. Bhatnagar, J.A. Krzycki, and J.G. Zeikus, Federation of European Microbiological Societies, Microbiology Letters, 41 (1987) pp. 337–343.

Identification of a Carbon Monoxide–Metabolizing Bacterium as a Strain of *Rhodopseudomonas Gelantinosa* (Molisch) Van Niel, M.P. Dashekvicz and R.L. Uffen, International Journal of Systematic Bacteriology, Apr. 1979, vol. 29, pp. 145–148.

Mutants of *Rhodospirillum Rubrum* Obtained After Long–Term Anaerobic, Dark Growth, R.L. Uffen, C. Sybesma and R.S. Wolfe, Journal of Bacteriology, Dec. 1971, vol. 108, No. 3, pp. 1348–1356.

The Active Species on $CO_2$' Utilized by Reduced Ferredoxin: $CO_2$ Oxidoreductase from *Clostridium Pasteurianum*, R.K. Thauer et al, European Journal of Biochemistry, 55, 111–117 (1975).

Biological Production of Alcohols from Coal Through Indirect Liquefaction, S. Barik et al, The Humana Press, 1988, pp. 363–378.

Biological Production of Liquid and Gaseous Fuels from Synthesis Gas, K.T. Klasson et al, Applied Biochemistry and Biotechnology, vol. 24/25, 1990.

The Biological Production of Ethanol from Synthesis Gas, J.L. Vega et al, Applied Biochemistry and Biotechnology, vol. 20/21, 1989.

Sulfinol Process Has Several Key Advantages, B.G. Goar, The Oil and Gas Journal, Jun. 30, 1969, pp. 117–120.

Carbon Monoxide Fixation Into the Carboxyl Group of Acetyl Coenzyme a During Autotrophic Growth of Methanobacterium, E. Stupperich, K.E. Hammel, G. Fuchs and R.K. Thauer, Federation of European Biochemical Societes, Microbiology Letters, vol. 152, No. 1, Feb. 1983, pp. 21–23.

Proton Translocation Coupled to the Oxidation of Carbon Monoxide To $CO_2$, and $H_2$ In *Methanosarcina Barkeri*, M. Bott and R.K. Thauer, European Journal of Biochemistry, 1989, pp. 469–472.

Photosynthesis in *Rhodospirillum Rubrum* I. Autotrophic Carbon Dioxide Fixation, L. Anderson and R.C. Fuller, Plant Physiology, 1967, pp. 487–490.

Biological Upgrading of COA–Derived Synthesis Gas: Final Report (Abstract), S. Barik, E.R. Johnson, C.W. Ko, E.C. Clausen, J.L. Gaddy, Fossil Fuels, vol. 110, 1989, p. 201.

Pyrolysis Process for Scrap Tires, S. Kawakami, K. Inoue, H. Tanaka, T. Sakai, American Chemical Society Symposium Series, 130, 1980, Washington, DC.

Biomass and Wastes, Inst. Gas Tech., E. Rensfelt, C. Ekstrom, 1991.

Chemical and Fuel Production by Anaerobic Bacteria, J.G. Zeikus, Annual Review of Microbiology, 1980, pp. 423–464.

Parameters Affecting the Kinetics of Ethanol Production from CO, $CO_2$, and $H_2$ by *Clostridium Ljungdahlii*, K.M.O. Lundback et al, Presented at Twelfth Symposium on Biotechnology for Fuels and Chemicals, Gatlinburg, Tennessee, May 1990.

*Clostridium Ljungdahlii* Petc SP.Nov., A New Acetogenic, Gram–Positive, *Anaerobic Bacterium*, R.S. Tanner and D. Yang, Abstracts of the 1990 Annual Meeting of the American Society for Microbiology, No. R–21, p. 249.

Indirect Coal Liquification, GADDY, Technical Support, 1985.

Study of Gaseous Substrate Fermentations: Carbon Monoxide Conversion to Acetate. 2. Continuous Culture, J.L. Vega, G.M. Antorrena, E.C. Clausen, and J.L. Gaddy, Biotechnology and Bioengineering, vol. 34, Sep. 1989, pp. 785–793.

Dashekvich et al. Identification of a Carbon Monoxide–Metabolizing Bacterium as a Strain of *Rhodopseudomonas gelatinosa* (Molisch) van Niel. International Journal of Systematic Bacteriology, Apr. 1979, vol. 29, pp. 145–148.

Uffen, R.L. Anaerobic growth of Rhodopseudomonas species in the dark with carbon monoxide as sole carbon and energy substrate. Proceedings of the National Academy of Sciences. Sep. 1976, vol. 73, No. 9, pp. 3298–3302.

Stupperich et al. Carbon monoxide fixation into the carbonyl group of acetyl coenzyme A during autotrophic growth of Methanobacterium. FEBS Letters, Feb. 1983, vol. 152, No. 1, pp. 21–23.

O'Brien et al. Association of Hydrogen Metabolism with Unitrophic or Mixotrophic Growth of *Methanosarcina Barkeri* on Carbon Monoxide, Journal of Bacteriology. Apr. 1984, vol. 158, No. 1, pp. 373–375.

Miller et al. Oxidation of Hydrogen and Reduction of Methanol to Methane is the Sole Energy Source for a Methanogen Isolated from Human Feces, Journal of Bacteriology, Feb. 1983, vol. 153, No. 2, pp. 1051–1055.

Diekert et al. Carbon monoxide fixation into the Carboxyl group of acetate during growth of *Acetobacterium woodii* on $H_2$ and CO2. FEMS Microbiology Letters, 1983, vol. 17, pp. 299–302.

Nakamura et al. Taxonomic Study of *Bacillus coagulans* Hammer 1915 with a Proposal for *Bacillus smithii* sp. nov. International Journal of Systematic Bacteriology. Jan. 1988, vol. 38, No. 1, pp. 63–73.

Kruger et al. Thermophilic Bacilli growing with carbon monoxide. Archives of Mirobiology. Nov. 1984, vol. 139, No. 4, pp. 402–408.

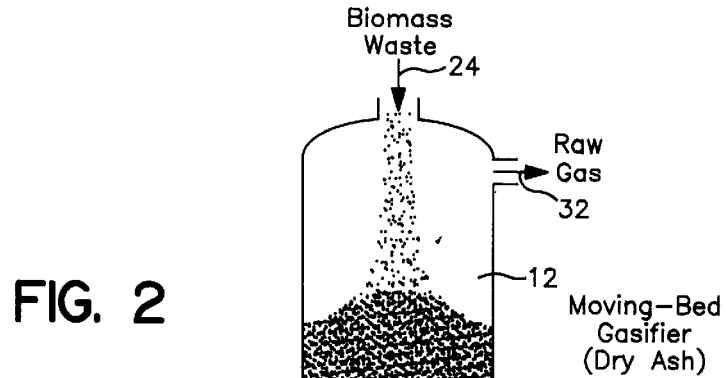
FIG. 2
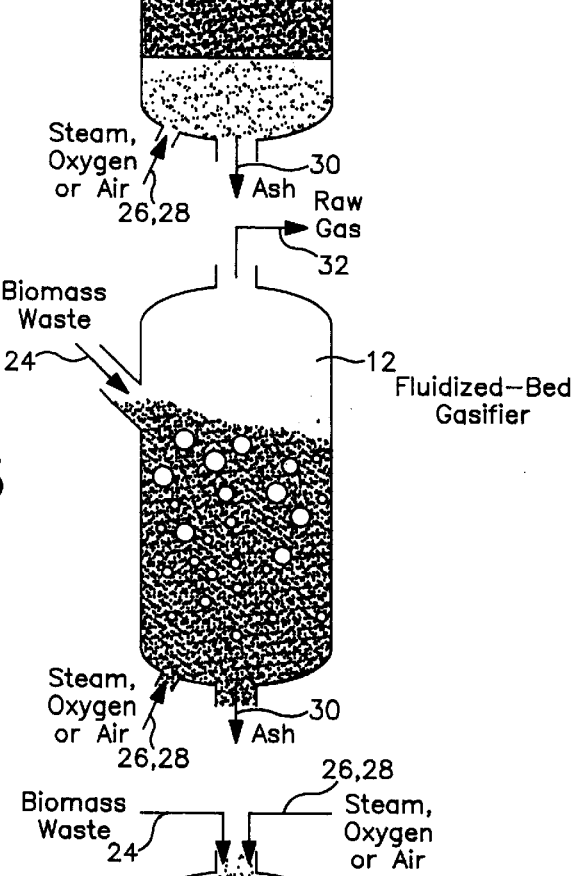
FIG. 3
FIG. 4
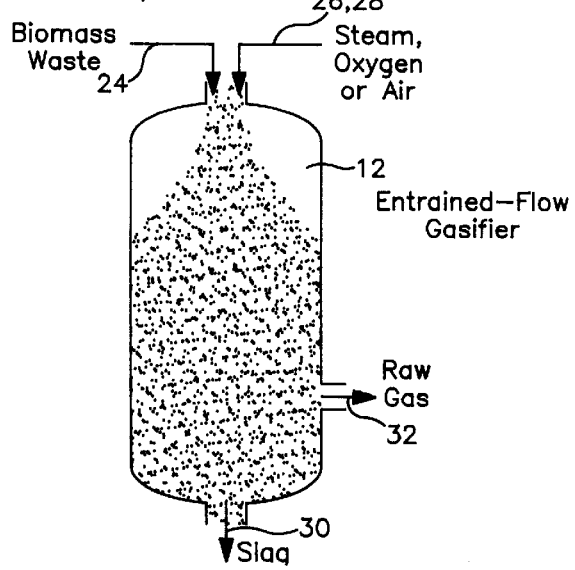

BIOCONVERSION OF WASTE BIOMASS TO USEFUL PRODUCTS

CROSS REFERENCE TO RELATED APPLICATION

This application is a continuation of Ser. No. 08/220,686, filed Mar. 31, 1994, now abandoned.

U.S. GOVERNMENT LICENSE RIGHTS

This invention was made with U.S. Government support under Department of Energy Small Business Innovation Research Program Contract No. DE-FG05-90ER81057 awarded by the Department of Energy.

BACKGROUND OF THE INVENTION

The present invention relates to a process for converting waste biomass to useful products utilizing anaerobic bioconversion in at least one stage of the process and to a biologically pure culture of an isolated anaerobic microorganism capable of producing useful products from synthesis gas.

The U.S. currently consumes 3.6 trillion cubic feet (TCF) of hydrogen annually, with worldwide consumption about three times this amount. The U.S. demand for hydrogen is expected to grow 60percent, or 1.4 TCF, in the next five years. This growth is primarily for refinery requirements to produce higher quality gasoline and to remove heteroatoms from lower quality crude. In addition, large quantities of hydrogen will be required for the production of alternative liquid fuels from coal, shale oil, or tar sands. The current contract price for hydrogen delivered by pipeline on the Gulf Coast is about $1.85 per MCF and is heavily dependent upon the price of natural gas. Further gas price increases will raise hydrogen prices proportionately.

This nation has a severe shortage of liquid fuel, but an abundance of coal. Logically, research has been directed toward developing technology for producing liquid fuels from coal. Processes have been developed for direct coal liquefaction, as well as liquefaction of synthesis gas by Fisher Tropsch reactions, methanol homologation, etc. (Hessley et al., 1986; Payne, 1987).

The liquid fuels produced have atomic hydrogen to carbon ratios (H/C) of about two and water is often a by-product, requiring additional hydrogen. Coal has a H/C ratio of, at best, one. Consequently, production of liquid fuels from coal requires substantial amounts (>50 percent) of added hydrogen.

The liquids from coal liquefaction, as well as from other fossil resources, such as bitumen from tar sands or kerogen from oil shale, contain large fractions of heteroatom compounds that must be removed before refining. These oxygen, sulfur and nitrogen contaminants are removed by reaction with hydrogen. Therefore, hydrogen is a key ingredient in the utilization of coal and other fossil energy reserves.

Most of the hydrogen produced throughout the world is made from synthesis gas. The synthesis gas may be derived by reforming of natural gas or by gasification of coal. Carbon monoxide in synthesis gas reacts with water to produce hydrogen by the water-gas shift reaction:

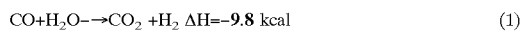

$$CO + H_2O \rightarrow CO_2 + H_2 \quad \Delta H = -9.8 \text{ kcal} \quad (1)$$

This slightly exothermic reaction is catalyzed by heterogeneous mixtures of metals such as chromium, iron, zinc, copper, cobalt, etc. (Wender, 1987). The catalysts are deactivated by sulfur, carbon deposition, and high temperature. Following the shift reaction, the $CO_2$ and other components may be removed by absorption and a pure hydrogen product is obtained. Alternatively, the water-gas shift reaction may be used to adjust the $H_2$ composition in synthesis gas, for subsequent reaction.

In today's economy, the cost of hydrogen by catalytic processes is excessive, which makes alternative liquid fuels uncompetitive. Consequently, coal conversion processes, and tar sands and oil shale development, are severely impeded by a lack of low cost hydrogen. An economical process for production of large quantities of hydrogen is required for development of these alternative energy strategies.

Therefore, there is a need for an improved, simple and economical process for the biological production of hydrogen.

SUMMARY OF THE INVENTION

In accordance with the present invention, a biological process is provided for converting waste biomass to useful products by gasifying the biomass to produce synthesis gas and converting the synthesis gas to a useful product or intermediate utilizing one or more microorganisms capable of converting a synthesis gas substrate to one or more useful products, such as hydrogen, acetic acid or ethanol.

In accordance with a particular embodiment of the present invention, waste biomass is converted to synthesis gas containing carbon monoxide (CO) and the CO is converted to hydrogen ($H_2$) by an anaerobic microorganism ERIH2, *Bacillus smithii* ATCC No. 55404.

The first stage in the development of the present invention was to demonstrate the technical feasibility of producing hydrogen by a unique biochemical route. The anaerobic photosynthetic bacterium *Rhodospirillum rubrum* was used to convert CO and water to hydrogen. Three tasks were performed: definition of the conditions of media, light, pH and temperature to maximize bacterial growth and hydrogen production; preliminary continuous reactor experiments to determine reaction rates and reactor volumes; and a preliminary process design and economic evaluation from the preceding data.

As described in more detail later, the first stage objectives were satisfactorily achieved. Stoichiometric yields of hydrogen have been obtained from CO with *R. rubrum*. Fast growth was observed on synthesis gas only; however, growth was maximized with a small amount of yeast extract at 30° C. and pH 7. Intrinsic kinetic parameters have been determined and show that fast hydrogen production rates are possible. Virtually complete conversion was obtained with short retention times in the CSTR. The projected economics show that hydrogen can be produced for $0.77 per MSCF including $H_2$ separation, so that commercialization at this price would be assured. The technical and economic feasibility of this technology was demonstrated.

The second stage of the present invention concentrated on defining the optimal culture and bioreactor for hydrogen production. To ensure that the best possible system was developed, cultures were screened for enzyme activity and hydrogen production. Promising cultures were optimized for hydrogen yield and CO conversion. Bioreactors that achieve high mass transfer rates, as well as high cell concentrations, were studied. Immobilized cell reactors and trickle bed reactors are especially suited for this application. Advanced bioreactor concepts such as solid-state fermentation, non-aqueous fermentation, and high pressure fermentation were applied to these reactors to enhance gas mass transport. Equivalent retention times of seconds are conceivable for this technology. Process design and economic evaluations of the various alternatives were used to guide the development of the present invention.

The third stage of development of the present invention involved the study of sources of synthesis gas, gasification methods and apparatus, and synthesis gas compositions in order to optimize an overall process of converting waste biomass, including coal, municipal solid waste, sewage sludge, plastic, tires, agricultural and fisheries waste and the like to useful products such as hydrogen, ethanol and acetic acid. The overall process includes the steps of gasifying the waste biomass to produce synthesis gas, converting the synthesis gas to the desired product or products using anaerobic gaseous-substrate fermentation, then recovering the product or products.

A principal objective of the present invention is the provision of a process for producing hydrogen from synthesis gas by anaerobic conversion.

Another object of the present invention is the provision of a biological process for converting synthesis gas to useful products.

Yet another object of the present invention is the provision of a process for converting waste biomass to useful products.

Still yet another object of the present invention is the provision of a commercially viable process for producing hydrogen from waste biomass by gasification of the biomass to produce synthesis gas, anaerobic bioconversion of the synthesis gas to hydrogen, and recovery of the hydrogen.

Another object of the present invention is the provision of a biologically pure culture of an isolated anaerobic microorganism *Bacillus smithii*, ERIH2, ATCC No. 55404.

Other objects and further scope of the applicability of the present invention will become apparent from the detailed description to follow, taken in conjunction with the accompanying drawings.

BRIEF DESCRIPTION OF THE DRAWINGS

FIGS. 2–4 are schematic illustrations of generic moving-bed, fluidized-bed, and entrained-flow gasification reactors, respectively;

FIGS. 5–19 initial conditions: 1 atm, 100 rpm, 30° C., various initial cell concentrations.

FIG. 5 Effect of Temperature on *R. rubrum* ATCC 9791

FIG. 6 Performance of *R. rubrum* ATCC 9791 and 25903

FIG. 7 $H_2$ Yield of *R. rubrum* ATCC 9791 and 25903

FIG. 8 Performance of *R. rubrum* ATCC 17032 and 25903

FIG. 9 $H_2$ Yield of *R. rubrum* ATCC 17032 and 25093

FIG. 10 Performance of *R. rubrum* ATCC 19613 and 25903

FIG. 11 $H_2$ Yield of *R. rubrum* ATCC 19613 and 25903

FIG. 12 Performance of *R. rubrum* ATCC 17031 and 25903

FIG. 13 $H_2$ Yield of *R. rubrum* ATCC 17031 and 25903

FIG. 14 Performance of *R. rubrum* ATCC 17036 and 25903

FIG. 15 $H_2$ Yield of *R. rubrum* ATCC 17036 and 25903

FIG. 16 Performance of *R. rubrum* ATCC 25852 and 25903

FIG. 17 $H_2$ Yield of *R. rubrum* ATCC 25852 and 25903

FIG. 18 Performance of *R. rubrum* ATCC 27048 and 25903

FIG. 19 $H_2$ Yield of *R. rubrum* ATCC 27048 and 25903

FIG. 82 Typical Equilibrium Lines for Chemical and Physical Solvents.

DETAILED DESCRIPTION OF THE PREFERRED EMBODIMENTS

Synthesis gases (syngas) consisting mainly of CO, $H_2$, and $CO_2$, may be produced from carbonaceous materials according to the approximate reaction:

$$CH_2O + 0.125O_2(+0.5N_2) \rightarrow 0.75CO + 0.25CO_2 + H_2 + 0.5N_2 \qquad (2)$$

Biomass Various biomass wastes are available for gasification, including paper, municipal solid waste (MSW), tires, bagasse, sewage sludge, sawdust, rice hulls, plastic paper-mill sludges, etc. (TABLES 1 and 2). Many of these wastes have a negative value because of their disposal costs. Coal, of course, may also be gasified by similar stoichiometry. The resultant gas composition is a function of the amount of air, or oxygen, necessary to generate the heat for pyrolysis of the biomass waste. An average synthesis gas composition is CO-30 percent, $H_2$-40 percent, $CO_2$-10 percent, and $N_2$-20 percent. If oxygen is used, nitrogen is eliminated. Typically, synthesis gas components will generally fall in these ranges: CO-10 to 50%, $CO_2$-8 to 50%, $H_2$-10 to 40%, $N_2$-0.5 to 60%, $CH_4$-0.01 to 10%, and S gas compounds -0.02 to 10%.

In accordance with the present invention, carbon monoxide may be converted into hydrogen by certain anaerobic bacteria according to:

$$CO + H_2O \rightarrow H_2 + CO_2 \qquad (3)$$

The performance of these bacteria is summarized later; however, very fast reaction rates have been achieved. Also, these bacteria are not sensitive to sulfur and, thus, raw synthesis gas can be used as the source of CO.

Figure 1:
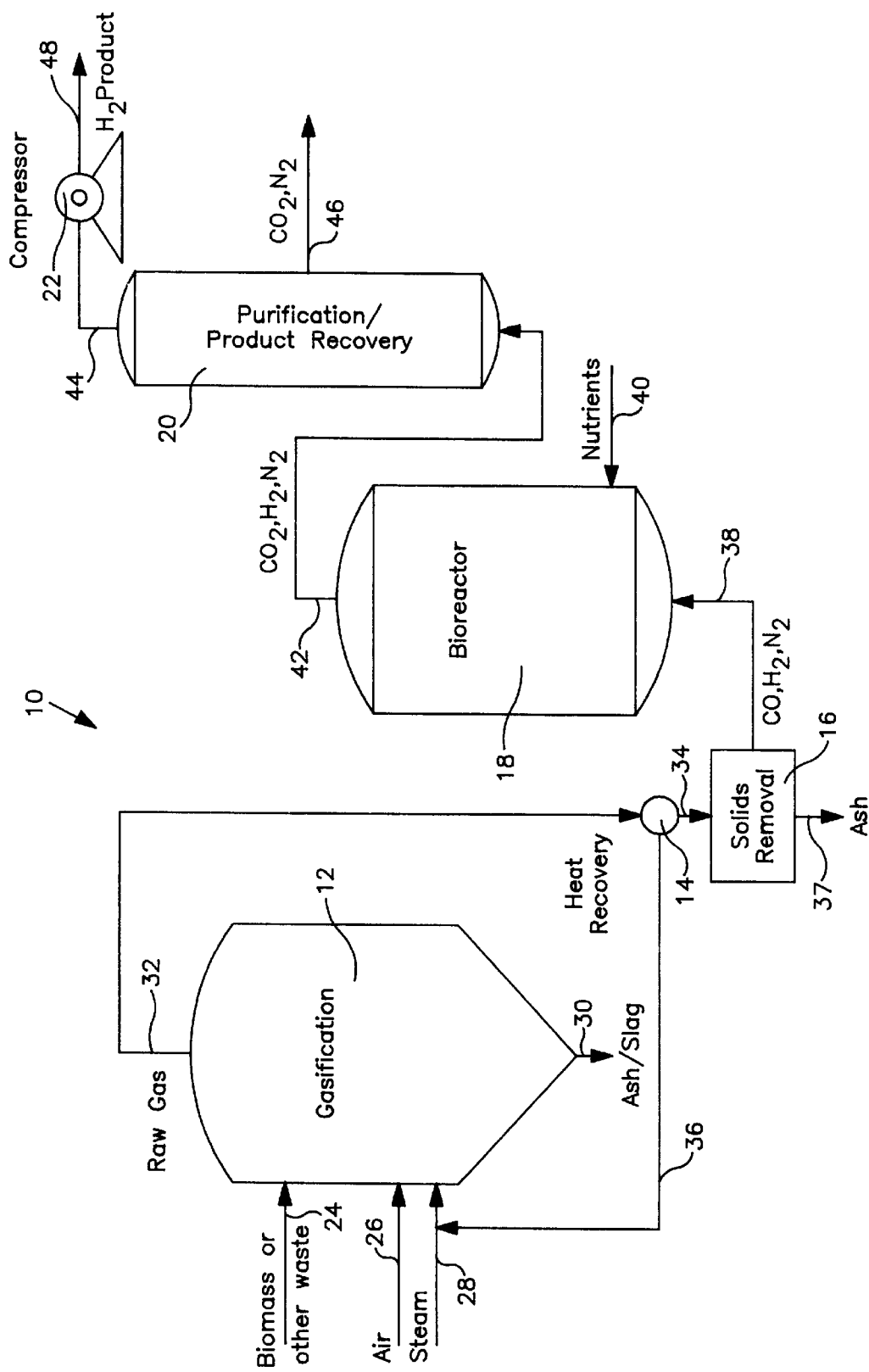
FIG. 1 of the drawings is a schematic representation of a system and process for converting waste biomass to useful products in accordance with the present invention.

The schematic flow diagram of the biological process and system for hydrogen production in accordance with an exemplary embodiment of the present invention is shown in FIG. 1. The process and system 10 includes a gasification unit or section 12 a heat recovery unit or gas cooler 14, a solids removal unit 16, a bioreactor 18, a purification unit or system 20 and a compressor 22. The gasification unit 12 is of conventional structure such as a moving-bed gasifier (dry ash), a fluidized-bed gasifier, or an intrained-flow gasifier, all of which are typically used for coal gasification. The gasification unit 12 has a biomass waste input 24, an air or oxygen input 26 (oxidant) and a steam input 28. The gasification unit 12 (reactor) has an ash or slag output 30 and a raw synthesis gas output 32 composed of high temperature and high pressure synthesis gas containing contaminants such as fly ash, dusty tar and oil. Typically, the biomass waste is input to the gasification unit 12 at a temperature of less than 500° F. and is gasified so as to produce an ash at a temperature of about 500°–1500° F. or a slag at 1500°–2500° F. and a raw synthesis gas at about 1000°–2500° F. The raw gas 32 is cooled to less than 80° F. in heat recovery unit 14, preferably cooled to 37° C. to produce a cooled gas output 34 and a steam output 36 which is recycled to the gasification unit 12. The cooled gas 34 passes through solids removal unit 16 to remove ash, slag, dusty tar, oil, light hydrocarbon liquids and the like contaminants 37 therefrom to produce a synthesis gas 38 which is fed to bioreactor 18.

The cooled gas 38 is fed into bioreactor 18 along with an aqueous nutrient media 40 and is converted by bacteria in the bioreactor into hydrogen and carbon dioxide which exits the bioreactor along with any nitrogen as a vent gas 42.

The vent gas 42 is treated by purification unit or system 20 which separates the hydrogen 44 from the other gas components 46. The hydrogen output 44 of purification unit 20 is compressed by compressor 22 to form a hydrogen product 48. Thus is described a system for converting biomass waste 24 into a useful product such as hydrogen 48.

The bioreactor 18 is operated at the same pressure as the gasifier 12. The hydrogen product 48 can be introduced into a pipeline or delivered to a customer or customers.

The biological process offers the advantages of high efficiency and low capital and operating cost. The microorganisms in the bioreactor 18 use only a small fraction of the syngas substrate 38 for growth and energy, therefore high product yields (98 percent) are obtained. The biocatalyst is automatically regenerated by slow growth of the bacteria, which are not inhibited by synthesis gas components. Biological processes are compatible with the environment and the utilization of wastes is environmentally beneficial.

The primary disadvantage of biological processes is generally the slow reaction rates. Cultures and bioreactors for this reaction have been studied extensively and are described later. Retention times of seconds have been achieved for the biocatalytic reaction, which makes this process competitive with catalytic processes.

MICROBIOLOGICAL PRODUCTION OF HYDROGEN FROM CARBON MONOXIDE

There are a large number of microorganisms that utilize CO and a few of these produce $H_2$ according to Equation (3). Many aerobic bacteria can grow on CO and $O_2$ as the sole carbon and energy sources (Hegemann, 1980; Uffen, 1981; Meyer and Schlegel, 1983). These organisms contain a membrane-associated carbon monoxide oxidase which catalyzes the irreversible oxidation of carbon monoxide in the presence of electron acceptors such as methylene blue. The aerobic enzyme contains molybdenum and is stable in the presence of molecular oxygen. Among the aerobic CO-oxidizing microorganisms, the carboxydobacteria are probably the most important and are recognized to be a major factor in the removal of carbon monoxide from the atmosphere (Spratt and Hubbard, 1981).

The bacterium *Rhodospirillum rubrum* has been shown to oxidize CO to $CO_2$ and produce stoichiometric amounts of $H_2$ from water nonphotosynthetically (Vega et al., 1988a). The cell growth, however, requires light and was not previously thought to require CO, but to utilize other organic carbon sources (Gest et al., 1950). Results from the first stage of development of the present invention have shown that *R. rubrum* can grow on the components of synthesis gas as the sole carbon source.

Recent research also indicates that $CO_2$ fixation can occur with *R. rubrum*. Quayle and Pfenning (1975) reported that several photosynthetic bacteria, including *R. rubrum*, are able to use the ribulose biphosphate pathway for $CO_2$ assimilation. *R. rubrum* can also grow autotrophically with $H_2$ (Anderson and Fuller, 1967). The primary product of autotrophic $CO_2$ fixation in *R. rubrum* is 3-PGA (Fuller, 1978). The path of carbon in *R. rubrum* during autotrophic metabolism involves CO2 fixation via the Calvin cycle and numerous ancillary carboxylations. Thus, coal gas can provide the components necessary for cell growth.

A basal medium, containing $NH_4Cl$ as the nitrogen source and acetate as a carbon source, has been recommended for growth of *R. rubrum* (Gest et al., 1950). Light is also needed as an energy source for growth. Small amounts of oxygen in the gas phase are not lethal to the bacteria. This bacterium can also tolerate high concentrations of $H_2S$ and COS (Vega et al., 1989a).

Recently, it has been found that other species have the potential to carry out the water-gas shift reaction. Certain CO utilizing methanogens have been found to produce $H_2$ from CO when methane formation is inhibited. Daniels et al. (1977) studied the CO oxidation of *Methanobacterium thermoautotrophicum*. Cell suspensions, previously frozen at $-20°$ C., produced stoichiometric $H_2$ and $CO_2$ for every mole of CO used. Only small amounts of $CH_4$ were formed. In the presence of chloroform, the formation of $CH_4$ was completely eliminated, with only $H_2$ and $CO_2$ as the end products.

O'Brien et al. (1984) reported that $H_2$ was produced when CO-adapted strains of *Methanosarcina barkeri* grow with more than 20percent CO as the sole carbon source and energy source, while $H_2$ was consumed when the CO concentration was below 20 percent. Bhatnagar (1987) reported that the purified CO-dehydrogenase from *M. barkeri* has $H_2$ production activity of 278.9 mmole $H_2$/min mg protein when 2 mM methyl viogen and 1 atm CO is supplied. Bott and Thauer (1989) reported that cell suspensions of acetate-grown *M. barkeri* catalyze the stoichiometric conversion of free CO to $CO_2$ and $H_2$ when methane formation from the products is inhibited.

Martin et al. (1983) observed the carbon monoxide-dependent evolution of $H_2$ by *Clostridium thermoaceticum*. Hydrogen was formed when *C. thermoaceticum* was cultivated heterotrophically on dextrose under a carbon monoxide gas phase. Resting cells from the CO-grown culture also formed $H_2$ when under CO with dextrose. In contrast, when cultivated under $CO_2$ only minimal levels of $H_2$ were detected. It was suggested that the mechanism involved some of the reducing equivalents generated by CO dehydrogenase ($CO+H_2O \rightarrow CO_2+2H^++2e^-$) to be converted to $H_2$ by subsequent action of hydrogenase. However, $H_2$ was not generated in the absence of dextrose, and it was not certain that $H_2$ was derived by the water-gas shift reaction.

One objective of the present invention was to determine the feasibility of the biological production of hydrogen from the water-gas shift reaction with *R. rubrum*. This objective was achieved by successfully enhancing culture performance and continuous reactor performance.

Stoichiometric yields of hydrogen were obtained from CO by *R. rubrum* ATCC strain 25903. Fast reaction rates were achieved in batch and continuous culture. *R. rubrum* can grow with coal gas as the sole carbon source, but small quantities of yeast extract were required to enhance growth rates. The optimal pH and temperature to maximize the growth and hydrogen production for *R rubrum* are 7° and 30° C., respectively. A light intensity of 1500 lux promotes cell growth, but light is not required for hydrogen production. Therefore, the synthesis gas bioreactor does not require a light source. The intrinsic kinetic parameters have been defined and indicate that fast rates in continuous culture, without substrate inhibition, are possible.

The results of experiments to define reaction rates in continuous culture show that retention times of less than 2 hours give virtually complete conversion of CO. The reaction is mass transfer limited and increasing the agitation rate improves the conversion. Mass transfer rates of 42 mmole/hr-L-atm have been achieved in the CSTR. The high conversions at short retention times and high mass transfer rates establish the technical feasibility of this process.

The purpose of the second stage of development of the present invention was to define the optimal culture and bioreactor system to maximize the yield and production of hydrogen from synthesis gas. The tasks performed in order to satisfy this objective were:

1. Culture Screening/Development
2. Continuous Bioreactor Studies
3. Advanced Bioreactor Concepts
4. Bioreactor Modeling/Scale-up The following description summarizes the research effort and demonstrates the technical and economic feasibility of $H_2$ production from synthesis gas with a composition representative of that from coal.

The objective of culture screening and development was two-fold: first, to screen all known shift conversion microorganisms to measure optimal performance and to select those with the best yields, rates, CO and sulfur (S) tolerances, and fastest growth with minimal nutrient and light requirements; and second, manipulation of the enzymatic pathways to further enhance performance. Culture performance was best judged on the basis of hydrogen production rate and yield. While *R. rubrum* was shown to give fast rates of growth and hydrogen production, there was no assurance that another shift conversion organism was not superior. However, rates and yields for other shift conversion organisms had not been determined so that a comparison could be made. Other important factors in selecting the best organism are growth rate, growth conditions (nutrients, light, pH, temperature), and tolerance to CO and sulfur gases. Therefore, all known shift conversion organisms were screened with several of the best organisms selected for subsequent parameter optimization. Tolerance to toxic substances was determined and the cultures manipulated to maximize enzyme activity. The best organism was then selected for continuous bioreactor studies.

There are five bacteria that are known to carry out the water-gas shift reaction: *R. rubrum, Rhodopseudomonas gelatinosa, Methanosarcina barkeri, M. thermoautotrophicum* and *Clostridium thermoaceticum*. However, there are several strains of each of these bacteria that may perform differently. For example, the American Type Culture Collection (ATCC) has 12 strains of *R. rubrum* and three strains of *R. gelatinosa*. Some strains of *R. rubrum* can grow in the dark (Uffen, 1971). Strains of *R. gelatinosa* have been isolated that grow without light and with CO as the sole carbon and energy source (Uffen, 1976; Dashekvicz and Uffen, 1979). In addition, other Rhodospirellaceae (members of Rhodopseudomonas, Rhodosprillum, Rhodocyclus, and Rhodomicrobium) may have the capability of producing hydrogen.

Each of these bacteria and the various strains were studied. An initial screening was conducted to select those bacteria that have promise. These screening experiments were conducted in batch reactors, using 150 ml serum bottles. All the shift conversion bacteria are anaerobes, and the anaerobic methods of Hungate (1969), as modified by Bryant (1972) and Balch and Wolfe (1976), were utilized.

Screening studies were conducted with all 12 strains of *R. rubrum*. The screening process included first activation of the culture, then adaptation to a synthesis gas atmosphere, and finally comparison of the CO consumption rate with other strains at the same cell concentration. Culture activation was performed in 25 ml roll tubes with 10 ml medium (Table 23) under 80 percent $N_2$ and 20 percent $CO_2$ atmosphere. The medium and the incubation temperature for the culture activation were prepared according to the ATCC recommendation for each strain. In all cases, illumination was supplied at 1800 to 1900 lux with a lighted shaking incubator.

Once the culture had grown in the roll tubes, the bacteria were inoculated into 150 ml serum bottles, containing 45 ml of the *R. rubrum* medium. The gas space was purged with synthesis gas, composed of 20.8 percent $H_2$, 64.34 percent CO, 4.06 percent $CH_4$ and 10.8 percent $CO_2$. More synthesis gas was supplied by regassing periodically as needed during the adaptation stage.

After the culture was adapted to synthesis gas and had consistent growth, the screening experiments were initiated. A relationship between cell concentration (dry weight) and optical density (482 nm wavelength) was obtained with *R. rubrum* ATCC strain 25903 as the control. Both strains were inoculated into two separate 150 ml serum bottles with 45 ml of fresh medium for each strain to form the same initial cell concentration. The inoculated bottles were then purged with one atmosphere of synthesis gas and incubated at 100 rpm in the shaker incubator with light at 1800–1900 lux. The gas compositions were periodically sampled and analyzed by gas chromatography to monitor the CO consumption rates and $H_2$ production rates. The performance of the strain was then based upon a comparison of the CO consumption rates and the $H_2$ yield from CO. The specific CO uptake rates and culture growth rates were also calculated.

Figure 5:
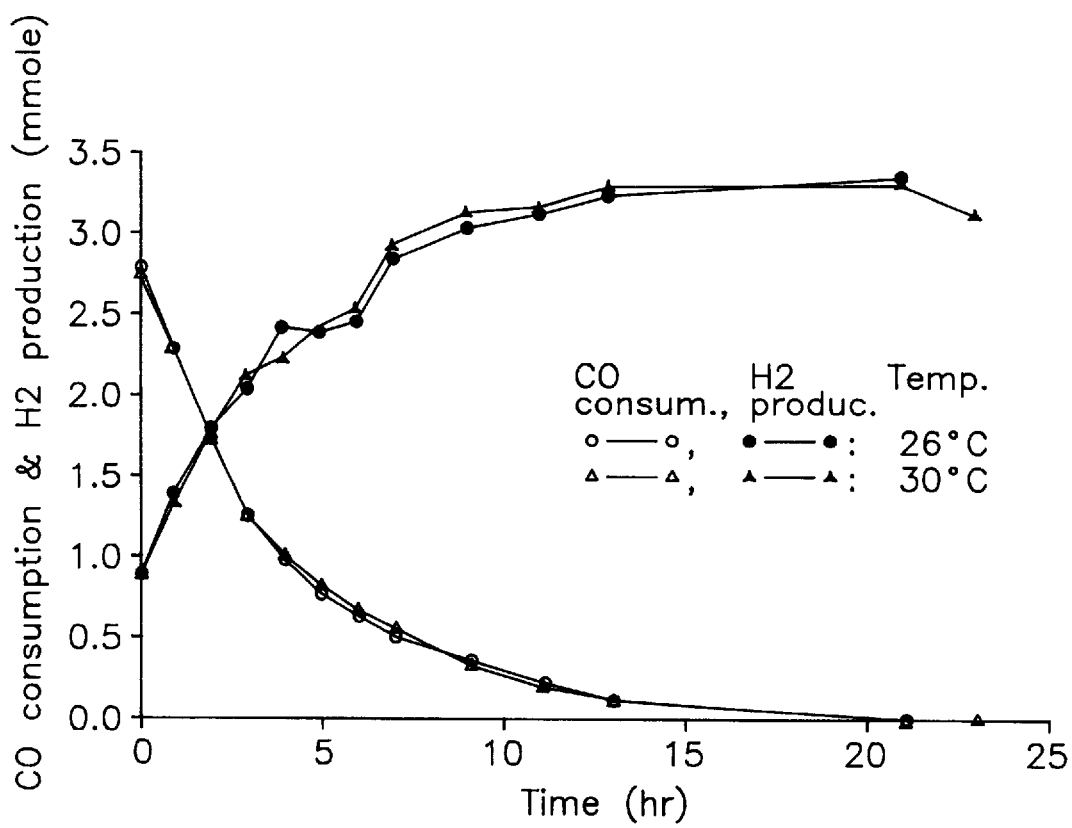
FIGS. 5–82 are graphical illustrations of the below-given relationships.

ATCC *R. rubrum* strains, 9791, 17031, 17032, 17036, 19613, 25852, and 27048 were compared with ATCC 25903 for the ability to utilize synthesis gas to produce $H_2$. The literature recommends that all the strains, except strain 9791, have an optimum incubation temperature of 30° C. However, as is shown in FIG. 5, CO consumption and $H_2$ production are not significantly affected by temperature between the optimum recommended temperatures of 26° C. for strain 9791 and 30° C. used for all other strains. Thus, the screenings were all conducted at 30° C.

Among the *R. rubrum* strains studied, ATCC 9791, 17032, and 19613 showed higher CO uptake rates than strain 25903. Table 4 shows a summary of the comparison. Since strain 25903 was used as the control for comparison in all of the experiments, variable performance was observed for this culture and the maximum and minimum values are listed. Strains 9791, 17032, and 19613 showed performance superior to the best case for strain 25903. The CO consumption rates of strain 17036 and 25852 were close to the minimum level of strain 25903. The performances of strains 17031 and 27048 were much worse than the rest of the group.

Figure 6:
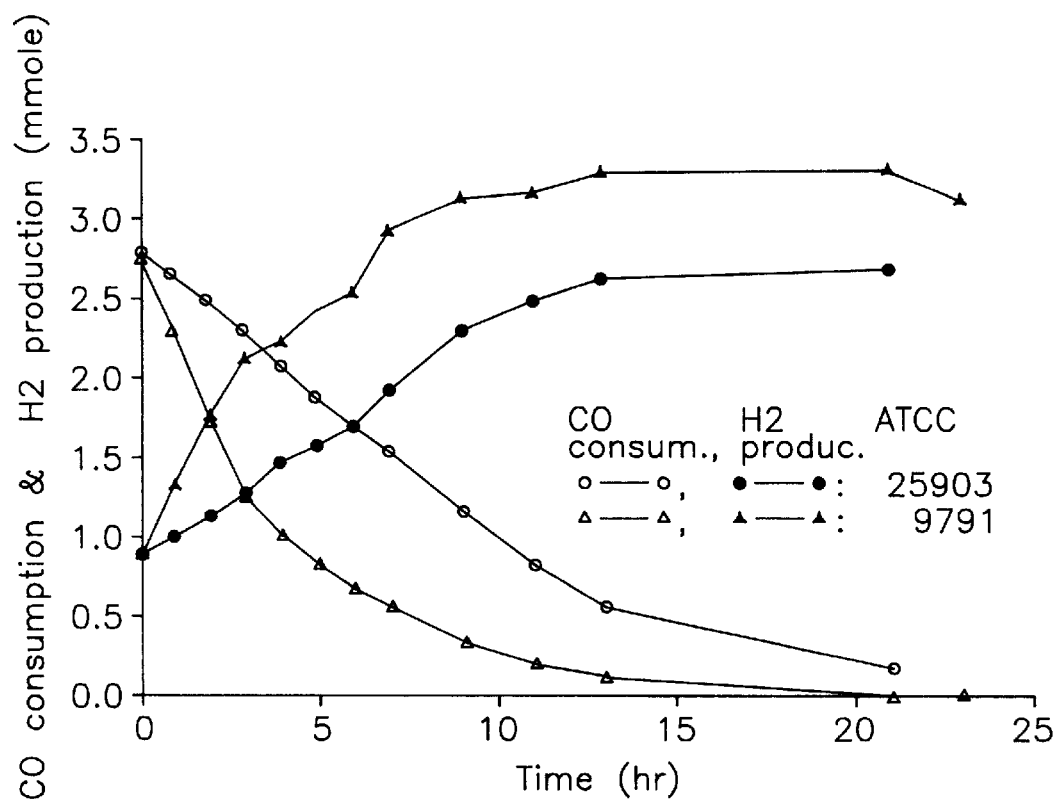
Figure 7:
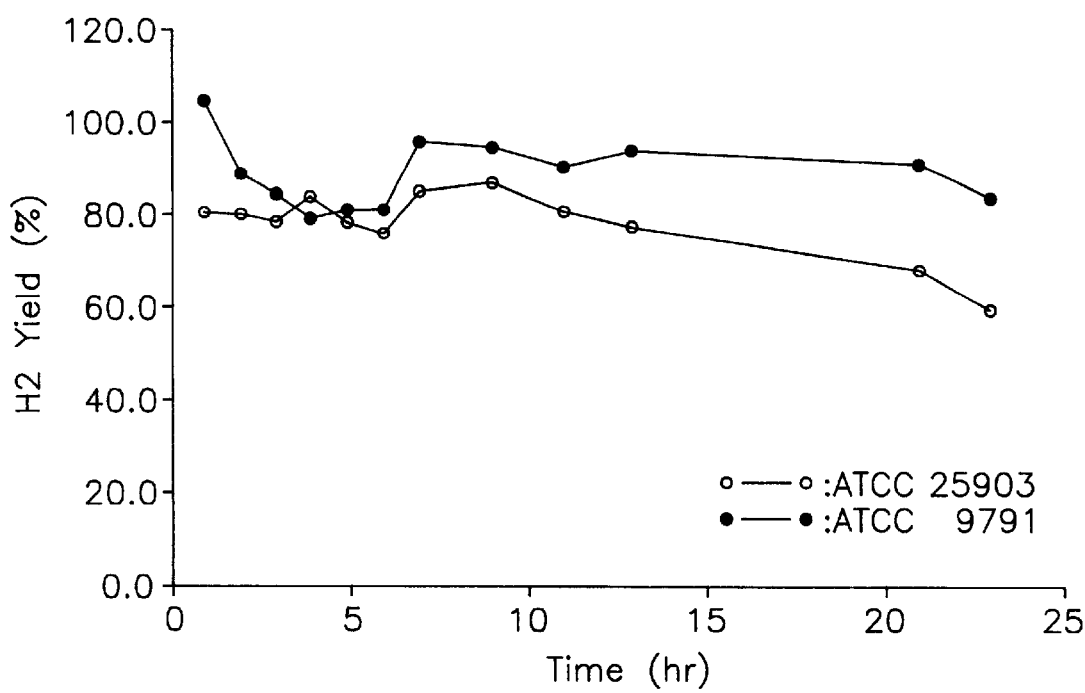

FIG. 6 shows CO consumption and $H_2$ production as a function of time for strains 9791 and 25903. FIG. 7 shows the hydrogen yields for these bacteria. As is shown in these figures, strain 9791 is superior in converting CO to $H_2$. Not only does strain 9791 consume CO faster than strain 25903, but it also gives a higher $H_2$ yield (90 percent compared to 80 percent) As is noted in FIG. 6, strain 9791 had a maximum CO consumption rate nearly three times higher than strain 25903 (27.9 vs. 9.6 mmole/g hr).

Figure 8:
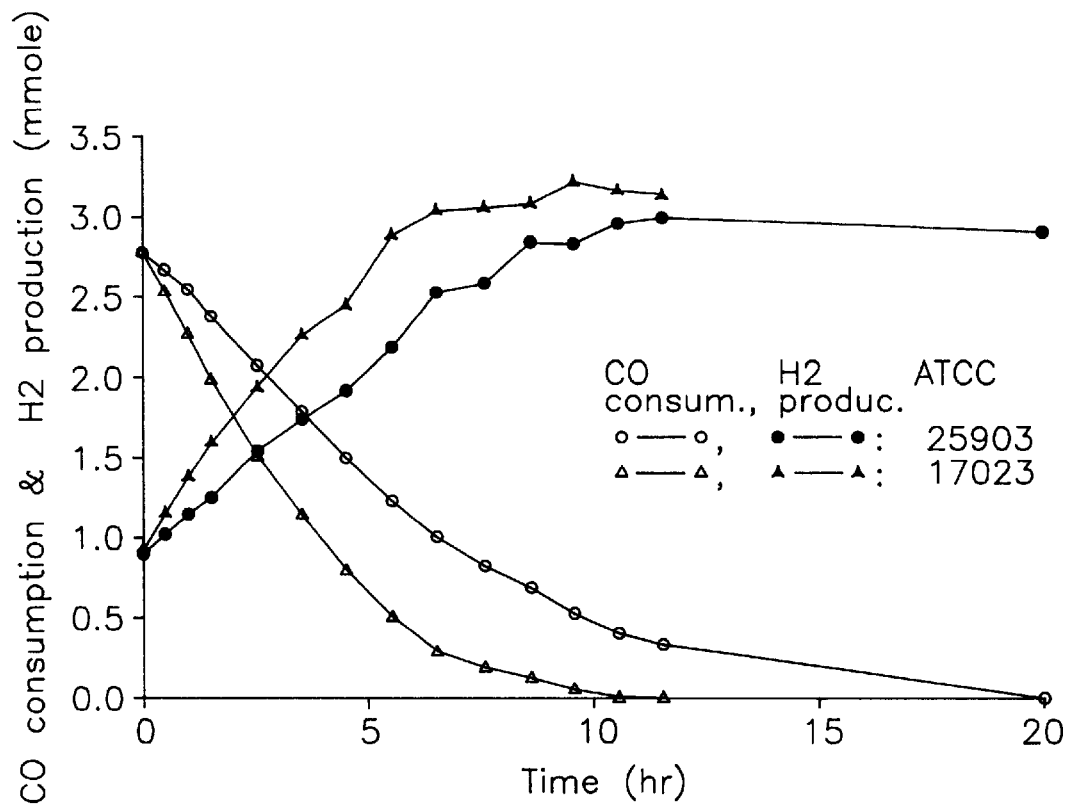
Figure 9:
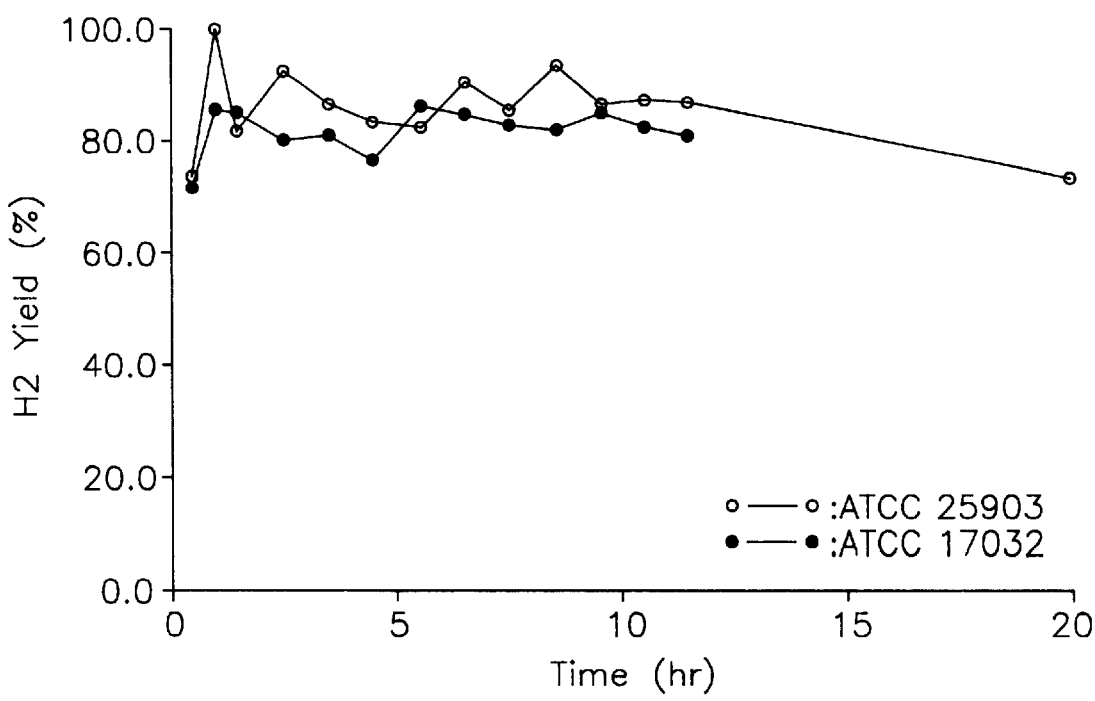

FIGS. 8 and 9 show the comparisons for strains 17032 and 25903. Strain 17032 had a maximum CO consumption rate of 22.5 mmole/g hr, about double that of the 11/3 mmole/g hr observed in strain 25903. However, strain 25903 had a slightly better $H_2$ yield, 85 percent vs. 82 percent.

Figure 10:
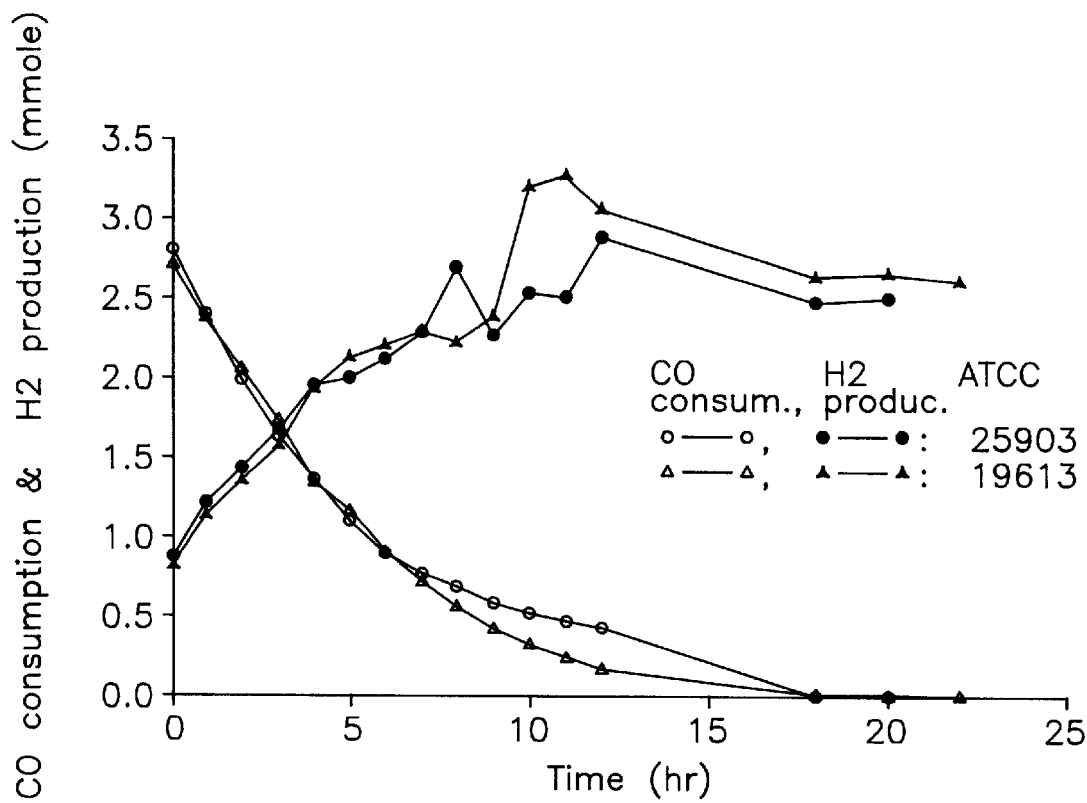
Figure 11:
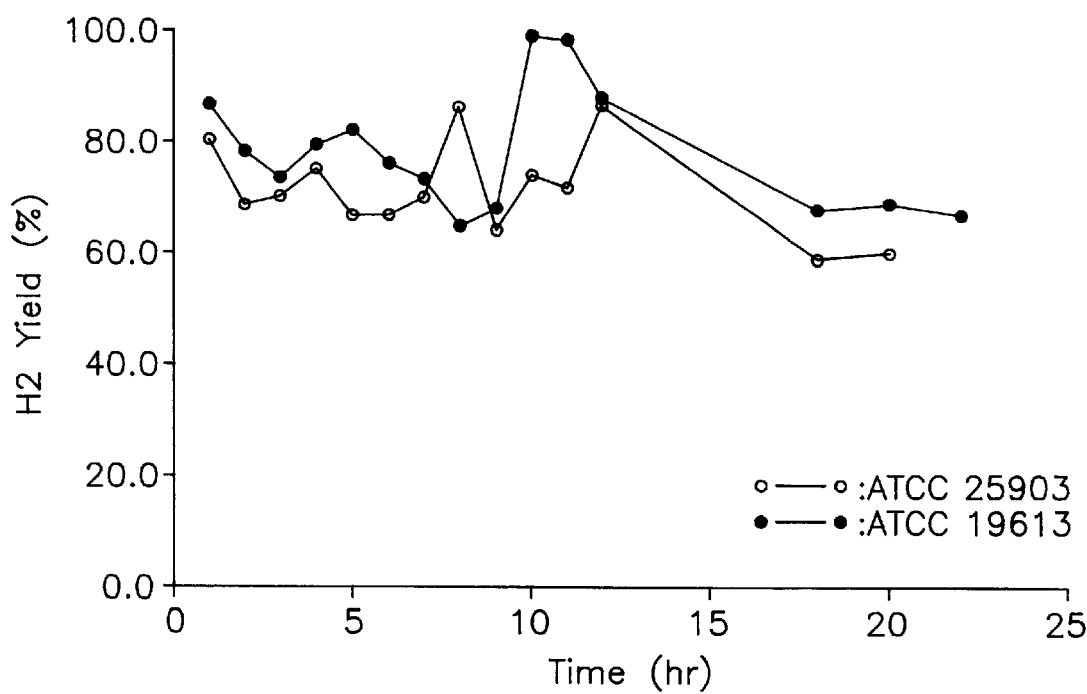
Figure 12:
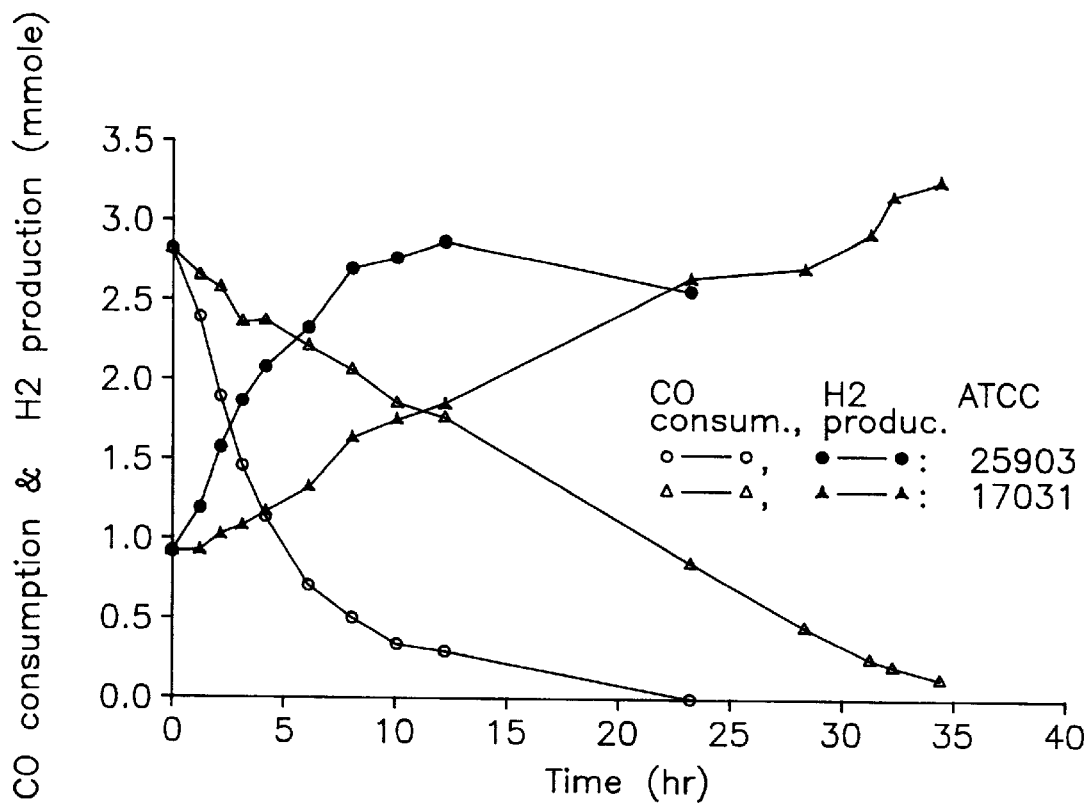
Figure 13:
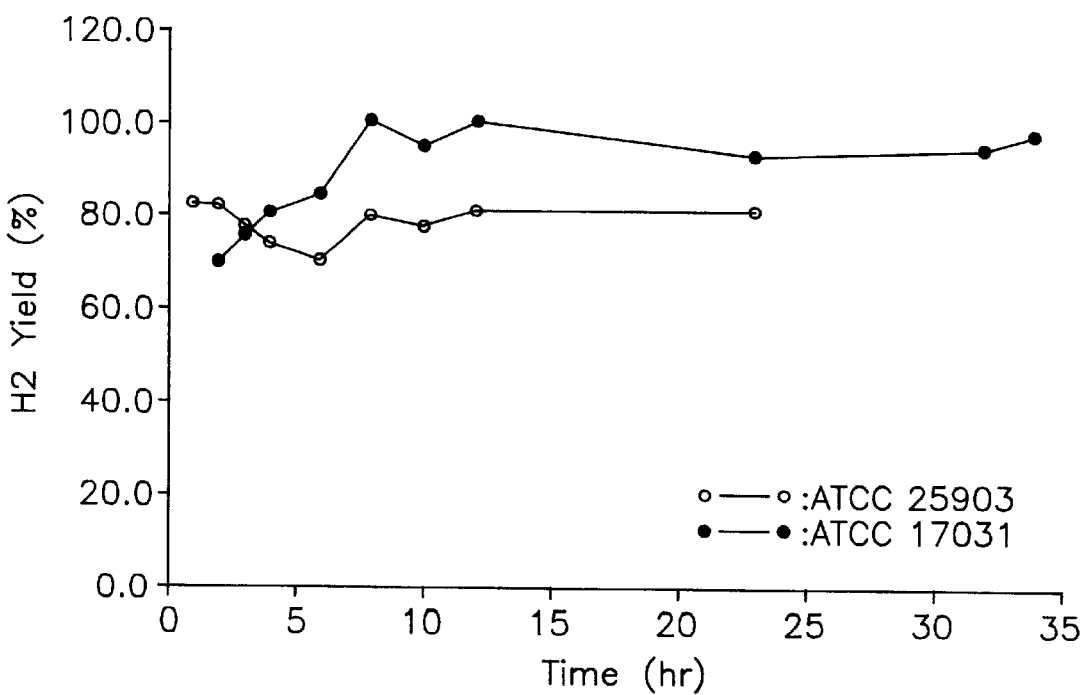
Figure 14:
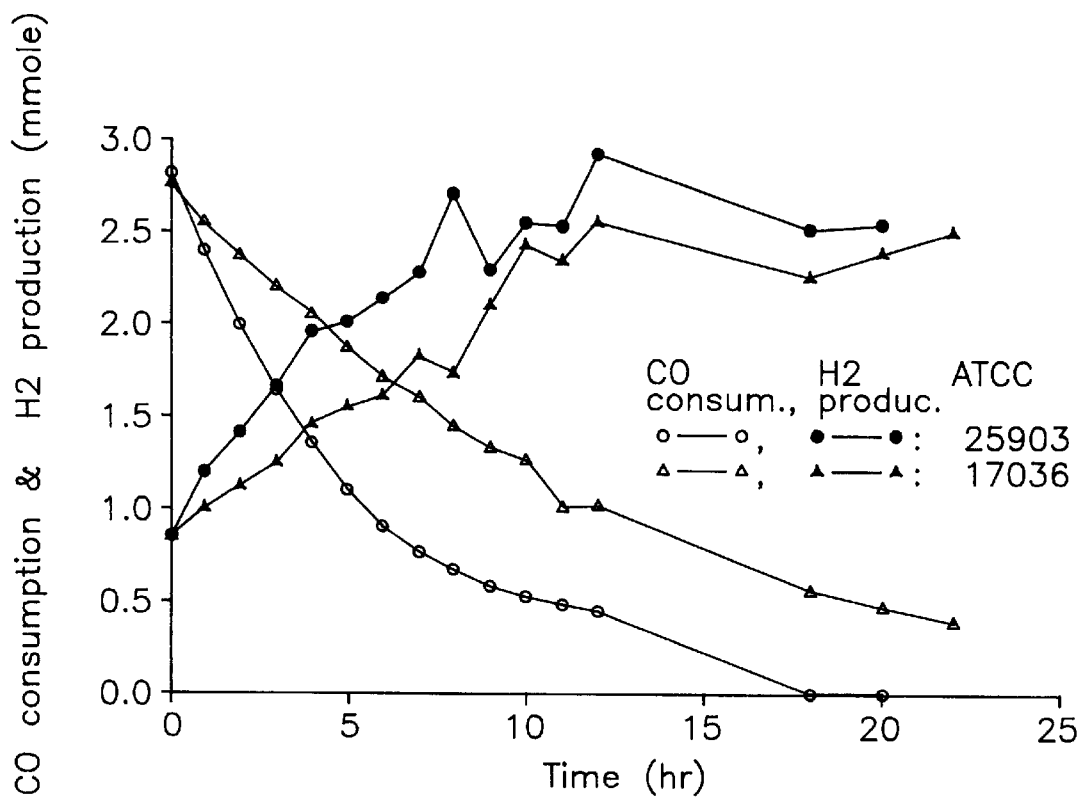
Figure 15:
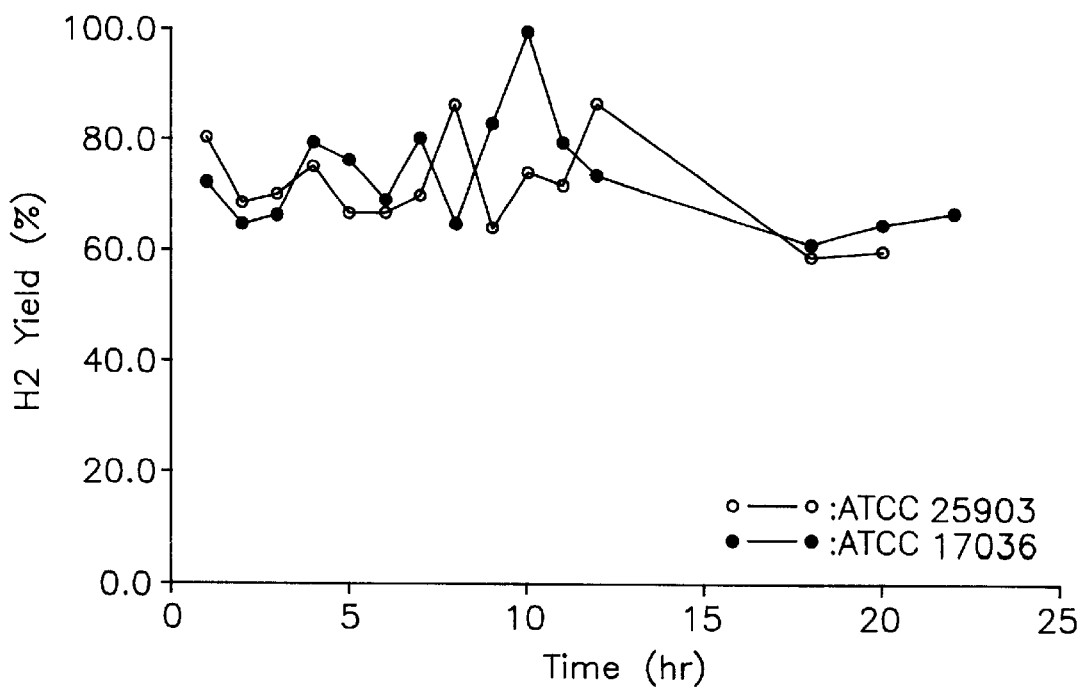
Figure 16:
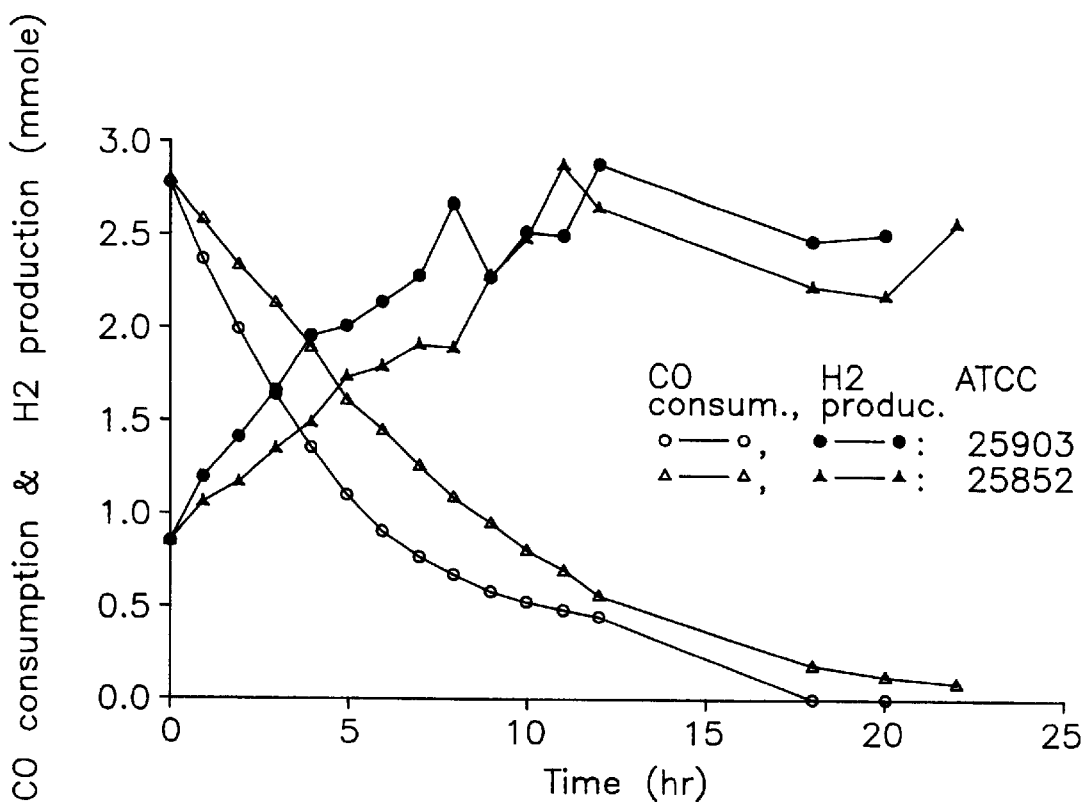
Figure 17:
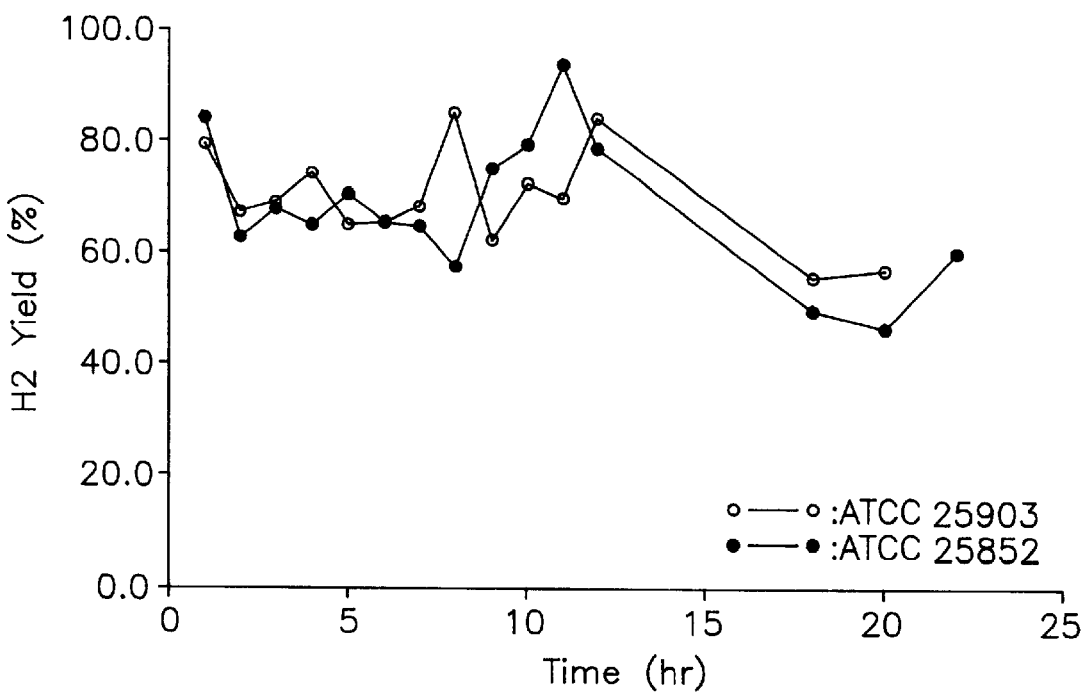
Figure 18:
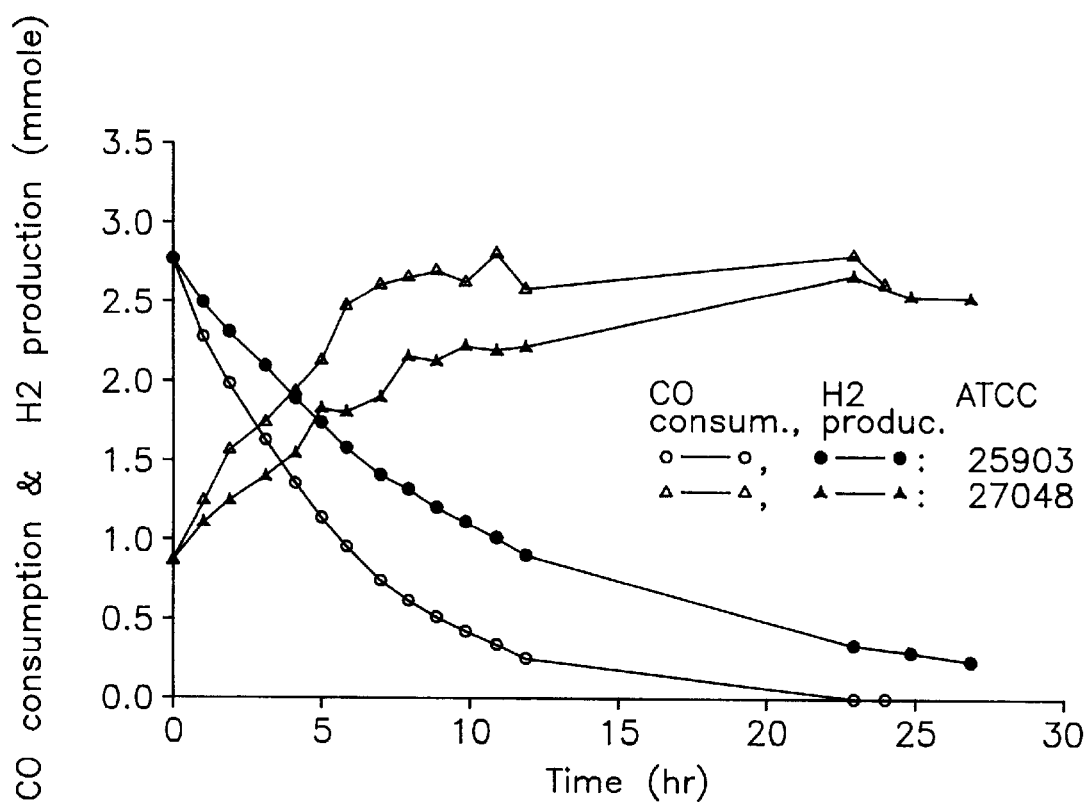
Figure 19:
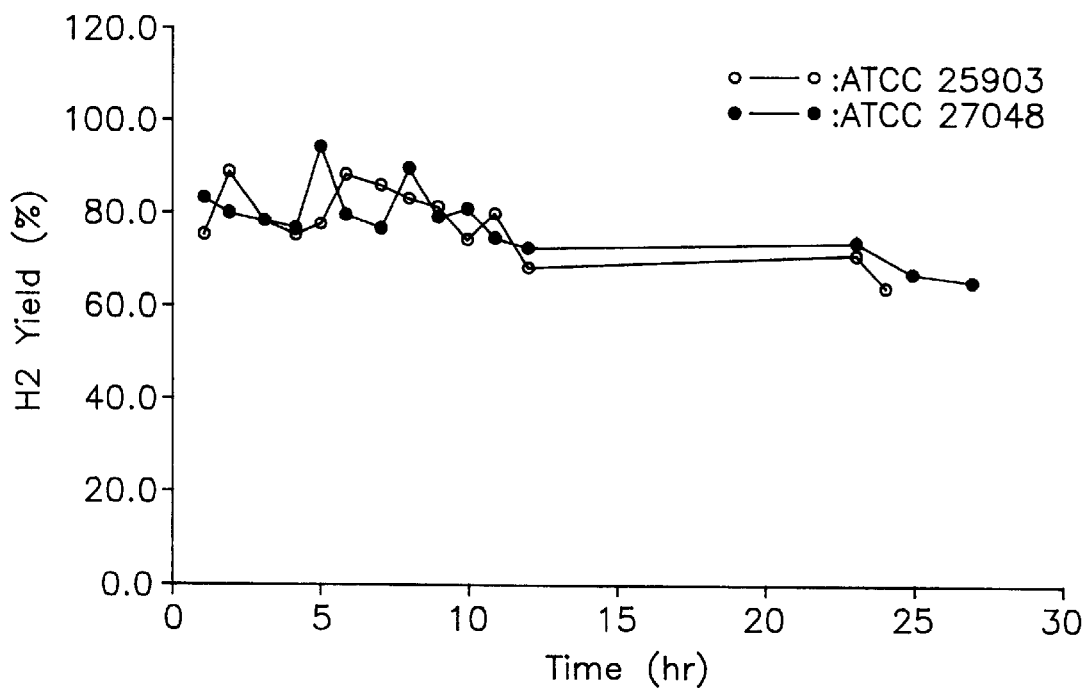
Figure 20:
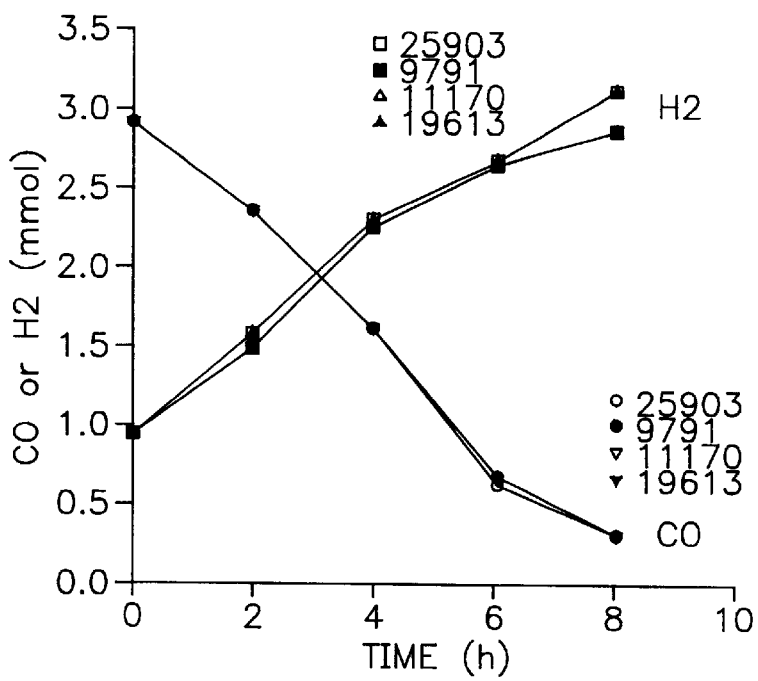
FIG. 20 Comparison of CO Consumption and $H_2$ Production with *R. rubrum* strains (Cell Conc. 0.5 g/L)
Figure 21:
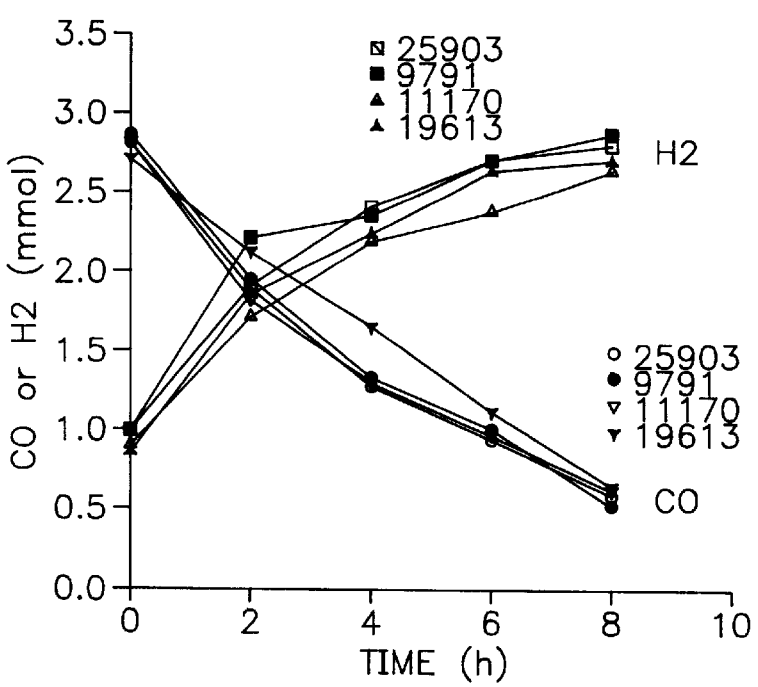
FIG. 21 Comparison of CO Consumption and $H_2$ Production with *R. rubrum* strains (Cell Conc. 0.57 g/L)
Figure 22:
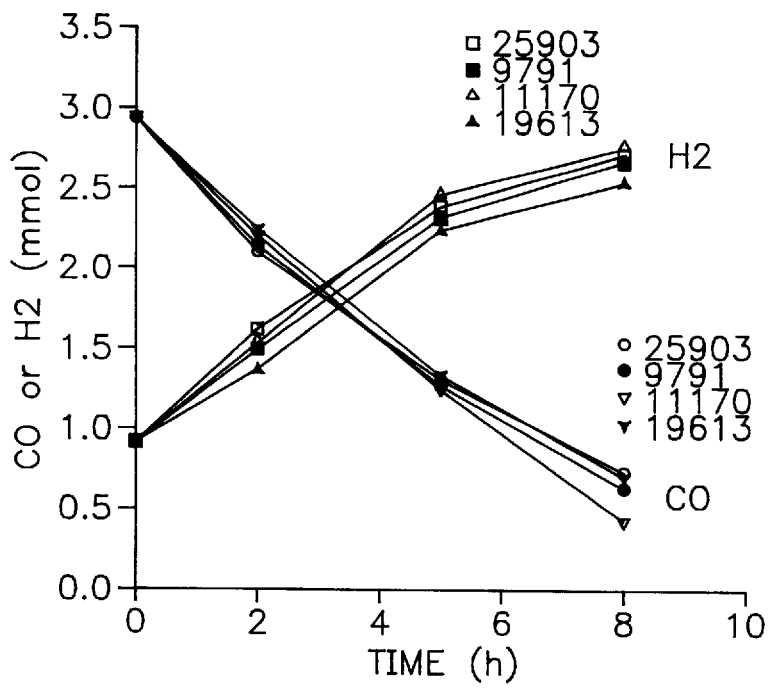
FIG. 22 Comparison of CO Consumption and $H_2$ Production with *R. rubrum* strains (Cell Conc. 0.54 g/L)
Figure 23:
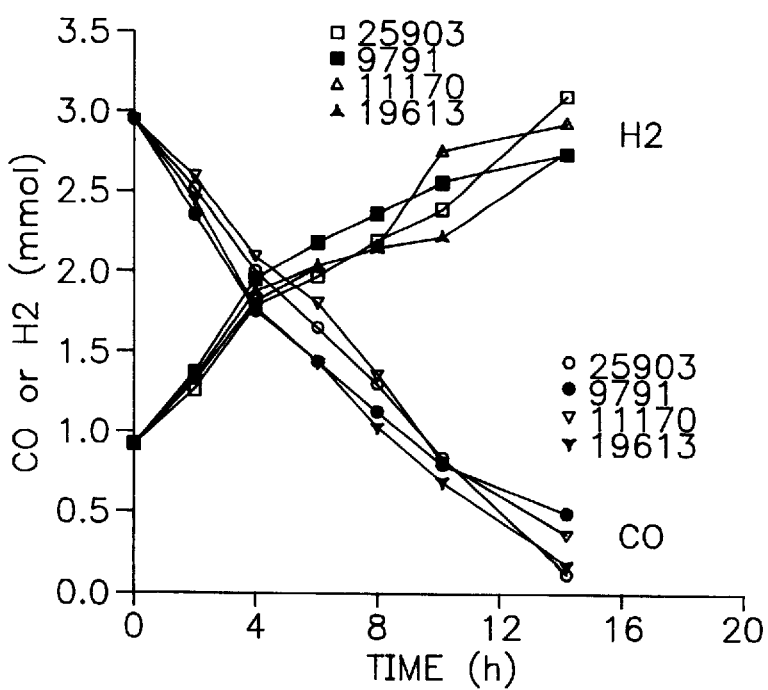
FIG. 23 Comparison of CO Consumption and $H_2$ Production with *R. rubrum* strains (Cell Conc. 0.4 g/L)
Figure 24:
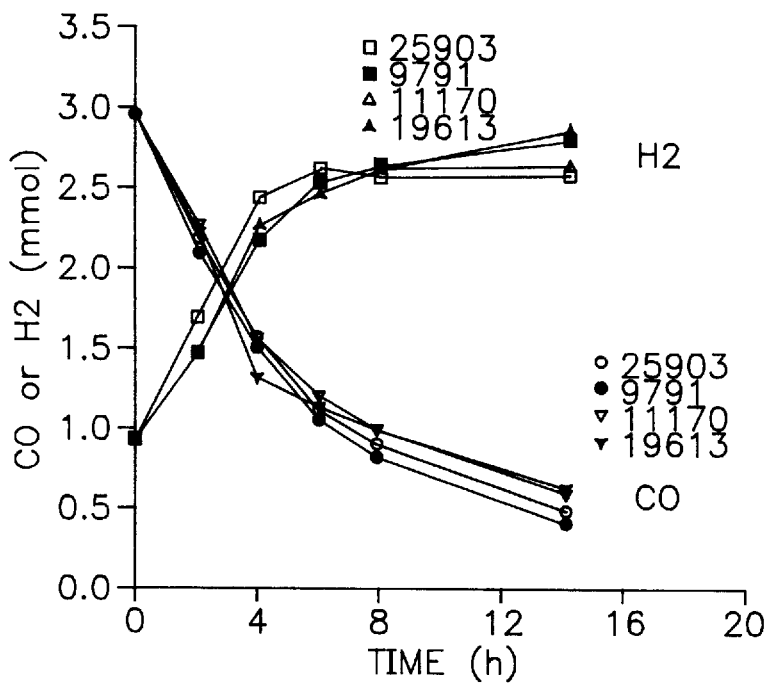
FIG. 24 Comparison of CO Consumption and $H_2$ Production with *R. rubrum* strains (Cell Conc. 0.45 g/L)

FIG. 10 shows the CO consumption and $H_2$ production for strains 19613 and 25903. Even though the overall CO consumption is very close in this comparison, the initial cell concentration of strain 19613 was only about 70 percent of that for strain 25903. Thus, the specific performance of strain 19613 is superior. The maximum CO consumption rates were 22.2 vs. 16mmole/g hr, while the average for the first five hours gave CO uptake rates of 220.1 vs. 12.8 mmole/g hr. FIG. 11 shows the comparison of the $H_2$ yield of these two strains. Strain 19613gave higher yields, 80 percent vs. 70 percent.

FIGS. 12–19 give comparisons of CO consumption, $H_2$production, and $H_2$ yield for the other bacteria. As is noted, these strains are inferior to R. rubrum 25903. Strains 9791, 19613, and 17032 were selected for further study. Each of these strains has a fast CO utilization rate and high yield. Strain 25903 was also studied further because of its fast growth rate.

To help identify the best R. rubrum strain, the specific CO consumption rates and the $H_2$ production yields were compared at five inoculum levels. FIGS. 20–24 show both the CO consumption and $H_2$ production in these five screening experiments. As is shown in these figures, there is no significant difference in the performance of these four strains. The CO consumption rate was in the range of 15 to 16.1 mmole/g hr, and the $H_2$ yield was in the range of 77 to 81 percent. Table 4 summarizes the data of these experiments. The average specific consumption rate was 15.6 mmole/g hr and the average yield was 79 percent.

Three strains of Rhodopseudomonas gelatinosa, ATCC 17011, 17013 and 17014, were obtained from ATCC. These three bacteria grow well on ATCC medium. However, no sign of CO utilization was observed with any of these strains under either lighted or dark conditions. According to Dashekvicz and Uffen (1979), strain 17011 is the only strain in the ATCC collection that exhibits CO dependent growth in the dark. CO adaptation of these strains was attempted by adding supplemental trypticase to replace yeast extract, as recommended by Uffen (1976) for the potential growth on CO. However, CO utilization was still poor such that R. gelatinosa was not considered further.

Figure 25:
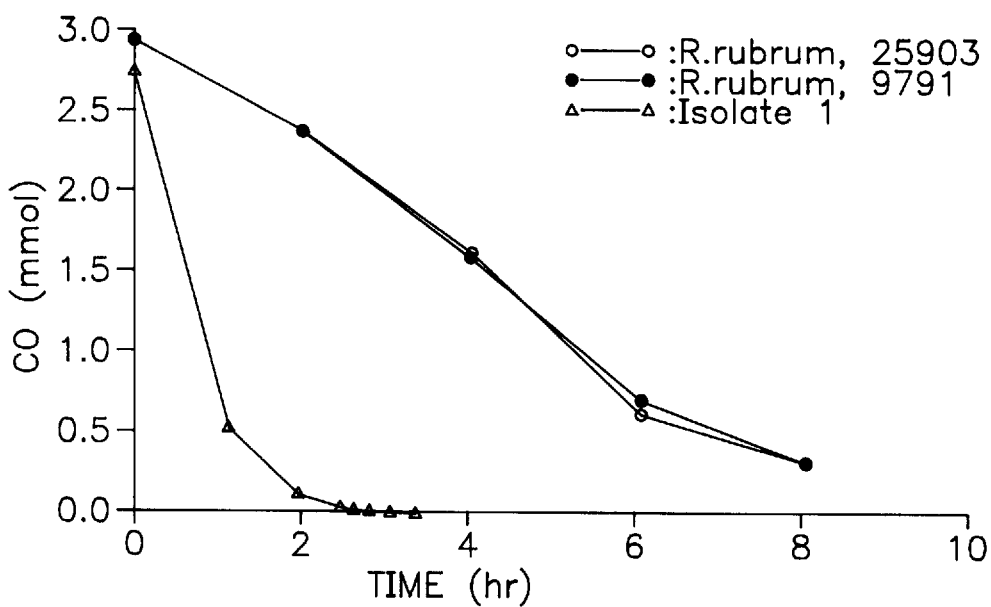
FIG. 25 CO consumption by *R. rubrum* and Isolate 1

Methanosarcina barkeri was activated with an atmosphere of 80 percent $H_2$ and 20 percent $CO_2$. Preliminary data indicated that this culture utilizes CO only at low CO partial pressures (0.15 atm). FIG. 25 shows that $H_2$, CO and $CH_4$ composition changes during a typical run. The initial gas composition was 14.3 percent $H_2$, 12.7 percent CO, and 5.02 percent $CO_2$ with the balance $N_2$. Since no methane inhibitor was provided, all $H_2$, including the gas produced from CO, was converted into $CH_4$. As is shown in FIG. 25, $CH_4$ formation continued after all the $H_2$had been consumed. This phenomena indicates that the water-gas shift reaction does take place in this culture.

Figure 26:
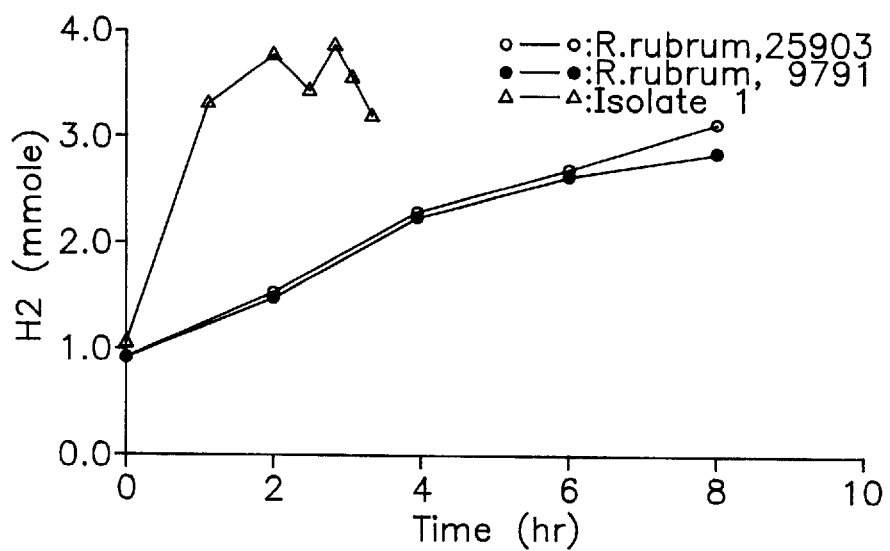
FIG. 26 $H_2$ Production by *R. rubrum* and Isolate 1
Figure 27:
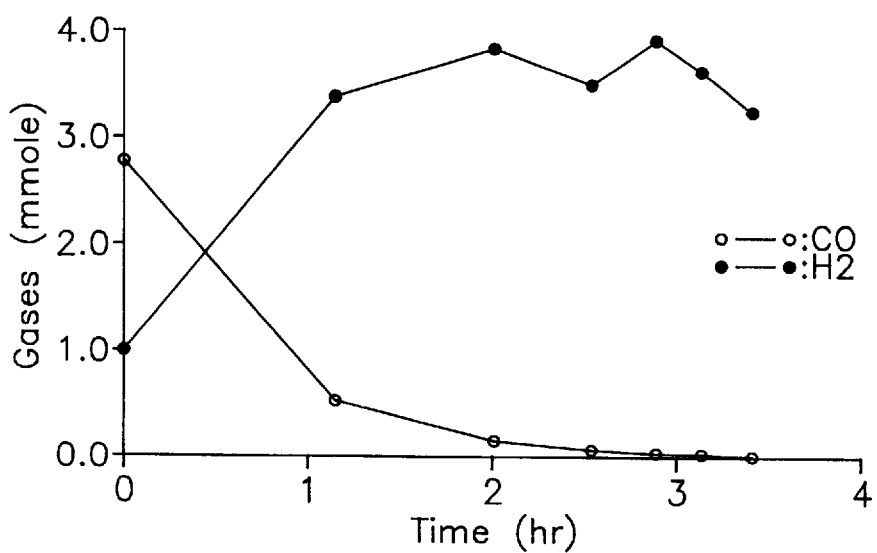
FIG. 27 CO Consumption and $H_2$ Production by Isolate 2
Figure 28:
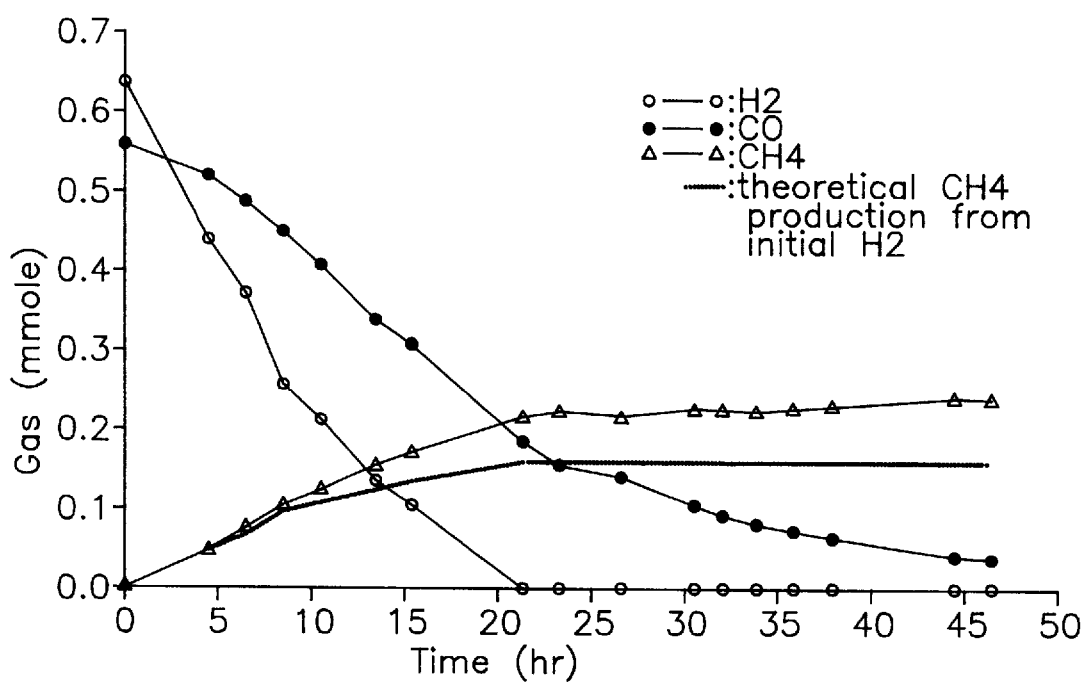
FIG. 28 CO Utilization/Methane Production by *M. barkeri*

In addition to R. rubrum and other cultures from ATCC, experiments were conducted to isolate cultures from nature. An enrichment labeled ERIH2 was obtained from these isolations. The ERIH2 isolate did not require light for growth and hydrogen production, and also had a much faster CO consumption rate. FIGS. 26 and 27 show comparisons of the CO consumption and $H_2$ production rates for R. rubrum and isolate ERIH2. The new isolate completely consumes the CO in about two hours while R. rubrum requires more than eight hours. The $H_2$ yield of the isolate ERIH2 is also very high. FIG. 28 shows the hydrogen production for isolate ERIH2 which is near 100 percent.

The new hydrogen-producing isolate ERIH2, which consumes CO rapidly and gives high hydrogen yields, was thought to be a new bacterial strain. The isolate was purified and sent to a microbiological laboratory for identification. Taxonomical studies were performed to determine the genus of the bacteria. ERIH2 was determined to be a new species of Bacillus and, more particularly, a new strain of Bacillus smithii by 16S rRNA sequencing and a partial phenotypic characterization and was deposited with the American Type Culture Collection, 12301 Parklawn Drive, Rockville, Maryland Md. 20252, on or about Mar. 18, 1993, with ATCC Designation 55404. The anaerobic strain ERIH2 was characterized as a gram-positive rod, that frequently produces distorted cells,and is non-spore forming, facultatively anaerobic, catalase positive, oxidase negative, methyl red positive, Voges-Proskauer negative, starch negative. It ferments glucose, producing formate, acetate and lactate, temperature optimum 50° C., range 35–65° C. Because of the obvious benefits in using ERIH2 (higher yields, no light requirements, faster rates), it was used in the bulk of the remaining development of the invention.

As was discussed previously, the bacterium ERIH2 has been shown to be very effective in producing $H_2$ and $CO_2$ from CO and water by the biological water-gas shift reaction. The specific CO uptake rate of $ERIH_2$ is nearly 20 times the value shown by R. rubrum in batch culture. However, ERIH2 suffers from poor growth rates, which limits the global rate of CO uptake. An experimental program was thus initiated to stimulate the growth of $ERIH_2$ through the use of growth supplements. The results of initial growth stimulation studies are shown below.

The growth of ERIH2 on various substrates was studied. Amino acids, asparagine and several sugars were tested as growth and energy sources. Table 5 shows the cell concentration changes with the addition of 2 g/L sugars. As is noted, nearly all of the sugars are able to support a minimal level of growth. However, only galactose, glucose, mannose, rhamnose and xylose can generate cell concentrations higher than 0.4. Also, for most of the sugars, the cell concentration was reduced after day 2, and only galactose and ribose gave continuous growth into the third day.

Corn steep liquor as a supplement to glucose was also investigated. Cell concentration results from batch studies using glucose plus corn steep liquor as the growth substrate are shown in Table 6. In addition to these carbon sources, the medium contained vitamins, minerals, salts, trypticase and yeast extract. As is noted in Table 6, the addition of corn steep liquor enhanced the cell concentration over glucose alone. However, the increase in cell concentration was not large enough to justify the addition of the additional substrate. It is also interesting to note in Table 6 that the impact of an additional 2 g/L of glucose on cell concentration was not immediate, but seen after 22 hr of incubation.

Glucose and galactose were selected for further growth studies, since glucose is the cheapest sugar and galactose has shown the fastest growth rates. In the second experiments, 5 g/L of sugars was used. Table 7 shows the results of growth and pH change. Both sugars supported growth to high levels within two days, with an accompanying reduction in pH, due to acid production. However, when the pH dropped below 5.5, the culture lost its ability to perform the water-gas shift reaction. As will be shown in the CSTR studies, the reduction in pH due to growth on glucose can be readily avoided by pH control inside the continuous reactor.

ERIH2 was next grown in batch culture on basal medium with 1g/L yeast extract and 1 g/L trypticase, supplemented with 0.75 and 1.5 g/L glucose at 50° C. and pH 6.9. Samples were removed periodically and checked for pH, cell concentration, ammonia production and glucose consumption.

Tables 8 and 9 show the results from this preliminary study. As is noted, ERIH2 grew rapidly during the first 8 hours of incubation, with the cell concentration increasing by a factor of 3.5–10. Glucose was consumed slowly during this period, with a significant amount of ammonia produced. After this initial 8 hours, glucose was consumed at a faster rate and ammonia production continued. The cell concentration continued to increase in one bottle, but fell in the other bottles, perhaps due to pH decreases.

These results indicate that ERIH2 grew mainly on trypticase and yeast extract during the first 8 hours of incubation. The continued production of ammonia after 8 hours of incubation indicates that ERIH2 cannot ferment glucose fast enough to couple all of the amino acids from trypticase and yeast extract into cell protein. Glucose transport across the cell membrane could thus be the growth limiting step. Additional sugars (lactose, sucrose, fructose, galactose) were tested next for their ability to enhance growth.

Based upon the encouraging results presented in Tables 8 and 9, an intensive study was performed to maximize the growth of ERIH2 in the presence of various nutrients. Nutrient supplements such as lactose, mixed vitamins, asparagene and aspartic acid did not appreciably affect growth. However, the use of high concentration of glucose, trypticase and yeast extract resulted in significantly higher cell concentrations. The feeding of 25g/L glucose, 20 g/L yeast extract and 5 g/L trypticase yielded a cell concentration of 5.0 (see Table 10). Thus, high cell concentrations are indeed possible with ERIH2 when using rich media.

Potential toxic compounds in synthesis gas include CO, $H_2S$, COS and trace quantities of hydrocarbons. The effects of these toxic compounds on R. rubrum were studied in batch experiments. The toxicity studies were conducted under optimal culture conditions of 30° C., pH 7, and a light intensity of 1500 lux, with various toxic gas partial pressures.

Figure 29:
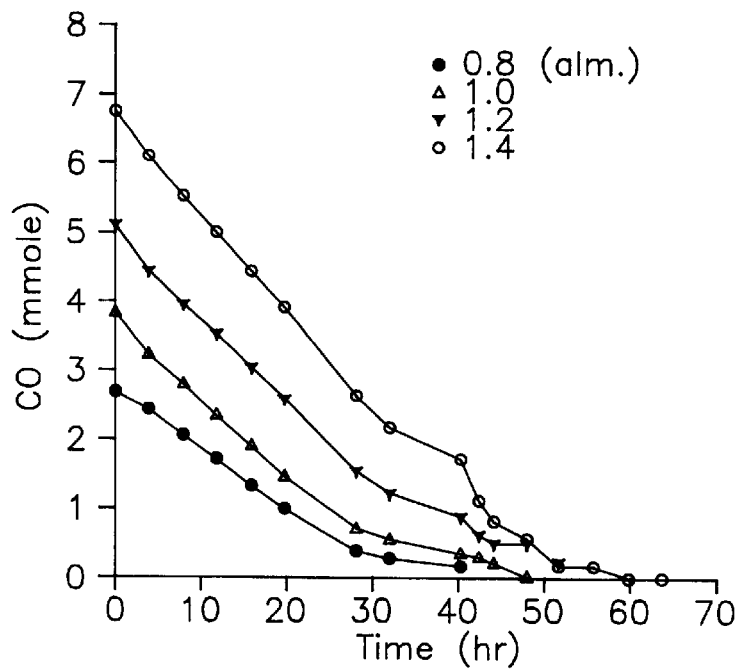
FIG. 29 The Effect of CO Concentration on CO Consumption
Figure 30:
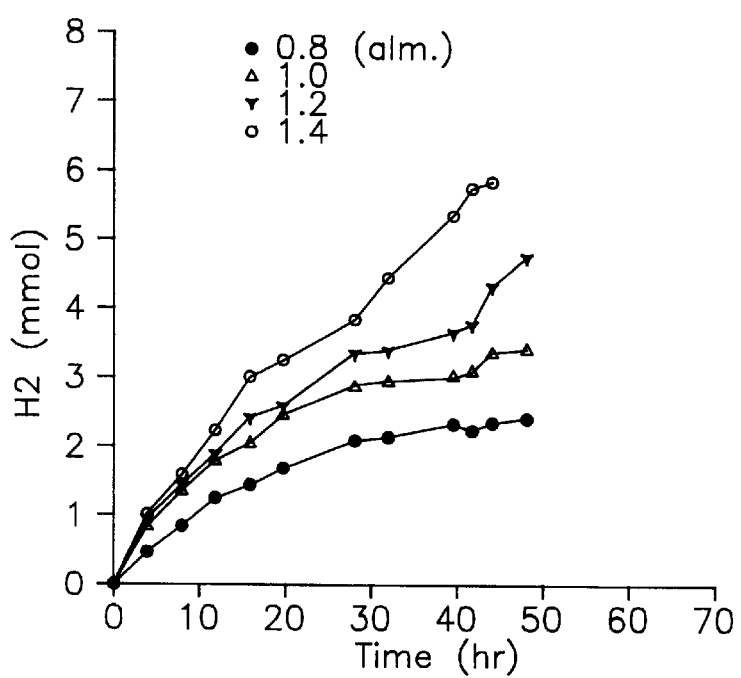
FIG. 30 The Effect of CO Concentration on $H_2$ Production
Figure 31:
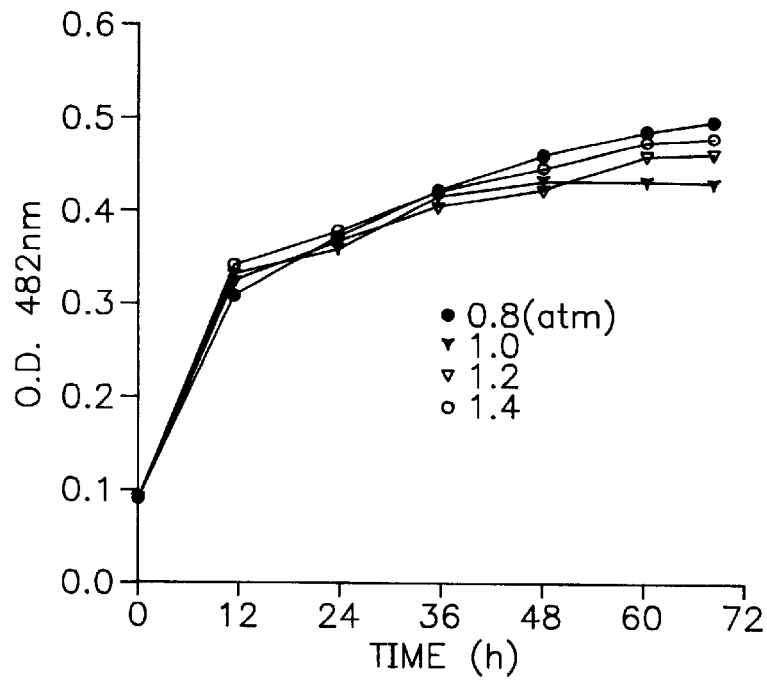
FIG. 31 The Effect of CO Concentration on Bacterial Growth

Even though CO is the major substrate for the water gas-shift reaction, CO has also been reported to be slightly toxic to R. rubrum. In this study, CO partial pressures of 0.8 to 1.4 atm were provided. FIGS. 29 and 30 show CO consumption and $H_2$ production, and FIG. 31 shows the cell growth for these studies. As is noted in FIGS. 29–31, neither CO consumption, nor $H_2$ yield were appreciably affected by CO partial pressures up to 1.4 atm. Similarly, cell growth was not affected by CO partial pressures up to 1.4 atm.

Figure 32:
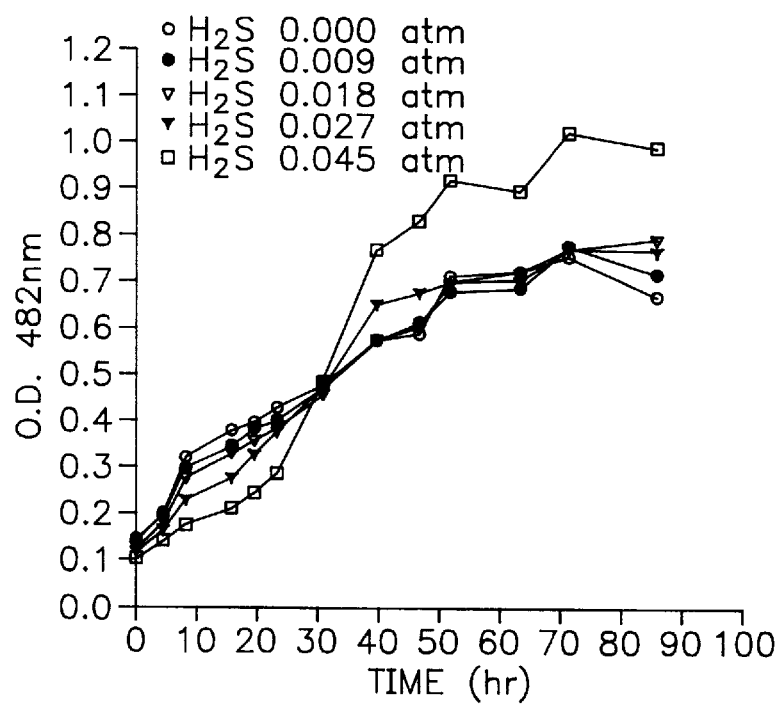
FIG. 32 $H_2S$ Toxicity on *R. rubrum* ATCC 25903
Figure 33:
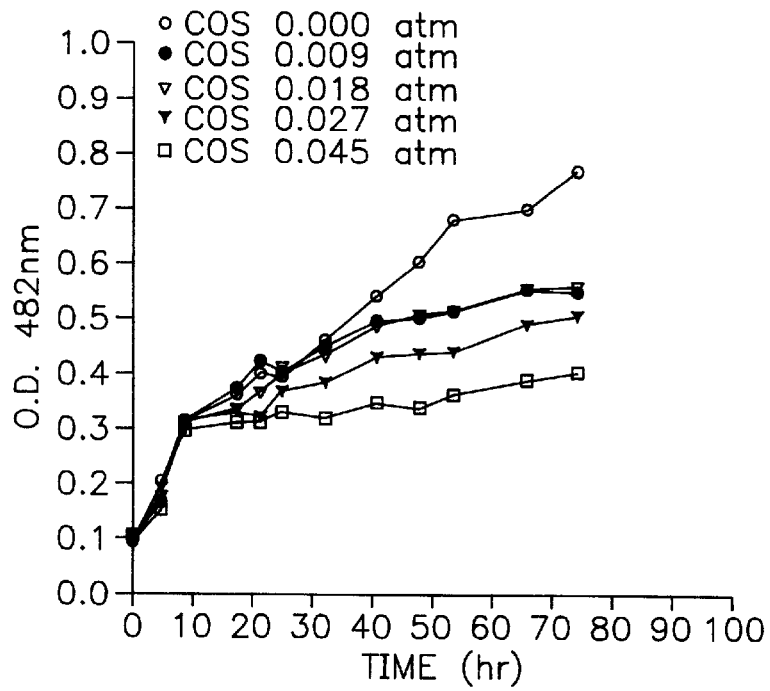
FIG. 33 COS Toxicity on *R. rubrum* ATCC 25903

Studies were also conducted with 0.009 to 0.045 atm $H_2S$ and COS, the expected concentration range for synthesis gas from high sulfur coal. FIGS. 32 and 33 show the cell growth with a sulfur gas environment, without resupply of synthesis gas. As $H_2S$ was added in increasing amounts, cell growth was slowed for the first 30 hours. This result indicates that $H_2S$ inhibits the initial growth with synthesis gas. However, cell growth was enhanced by the addition of higher concentrations of $H_2S$ after 30 hours. The initial charge of synthesis gas was completely utilized in the first 30 hours; thus, the growth was supported either from $H_2$ or yeast extract. For the COS study, there was no difference in growth in the first 10 hours. However, the growth after 10 hours was impaired by the addition of COS.

Figure 34:
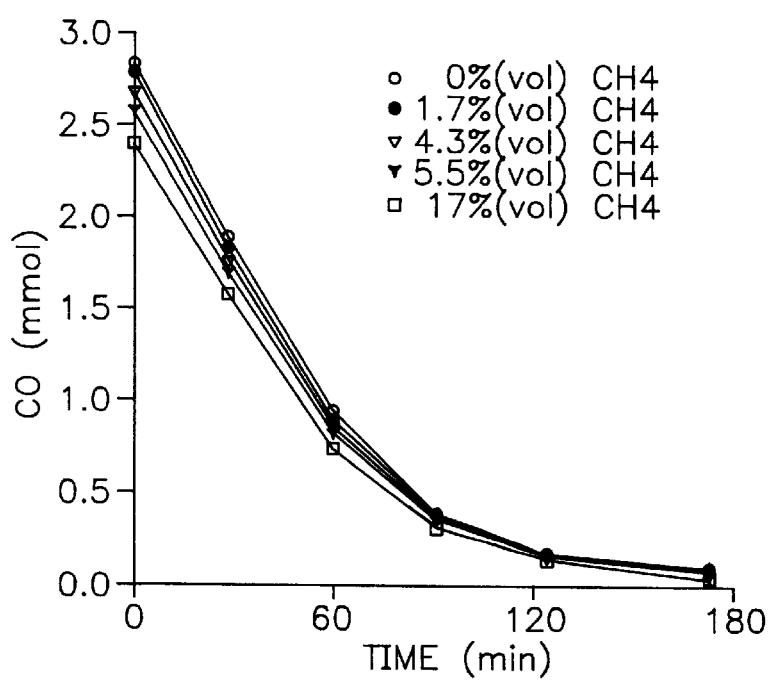
FIG. 34 The Effect of Methane on CO Consumption

The effect of trace hydrocarbons on ERIH2 has been studied using methane gas. FIG. 34 shows the effect of 0 to 17 percent of methane on CO consumption. As is shown in FIG. 34, CO utilization by ERIH2 was not affected by the presence of methane.

The R. rubrum cultures were manipulated to enhance the $H_2$ production. The manipulation of the enzyme pathways is a factor in improving culture performance. The enzymes involved in the biological shift conversion reaction include CO-dehydrogenase, hydrogenase and/or nitrogenase. Hydrogen production depends on the presence of certain metals; for example, carbon monoxide dehydrogenase from R. rubrum has been characterized as a nickel, zinc, iron-sulfur protein. Enhancement of ERIH2 has been by continued culture transfer.

Continuous stirred tank reactor (CSTR) studies with R. rubrum were conducted in a 2.5 L New Brunswick BioFlo IIc fermenter. This fermenter has controlled temperature, agitation, medium (Table 21) flow rate, and pH. The pH was monitored but not controlled in this study since there was no significant pH change involved. The gaseous substrate was manually controlled by a gas flow meter. Light was supplied for growth of R. rubrum by direct illumination to the fermenter and/or by recycling a liquid stream through an illuminated plastic vessel. A 40 watt tungsten bulb was placed inside the center of the vessel and cooling water was circulated inside to absorb the heat from the bulb. This lighted device was used to simulate the lighting system in a commercial size reactor. The illumination was controlled by the flow rate of the recycled liquid stream.

Figure 35:
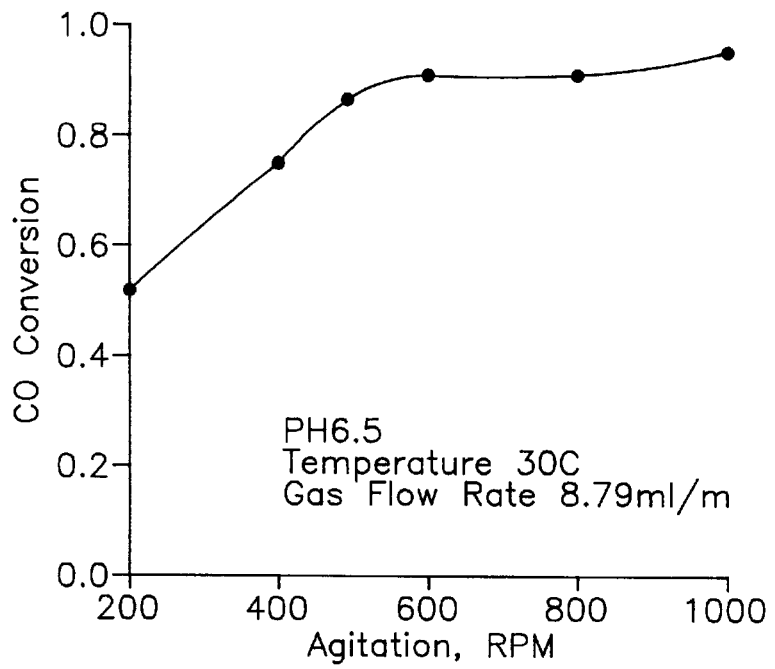
FIG. 35 CO Conversion as a Function of Agitation in Continuous Culture with *R. rubrum* ATCC 25903
Figure 36:
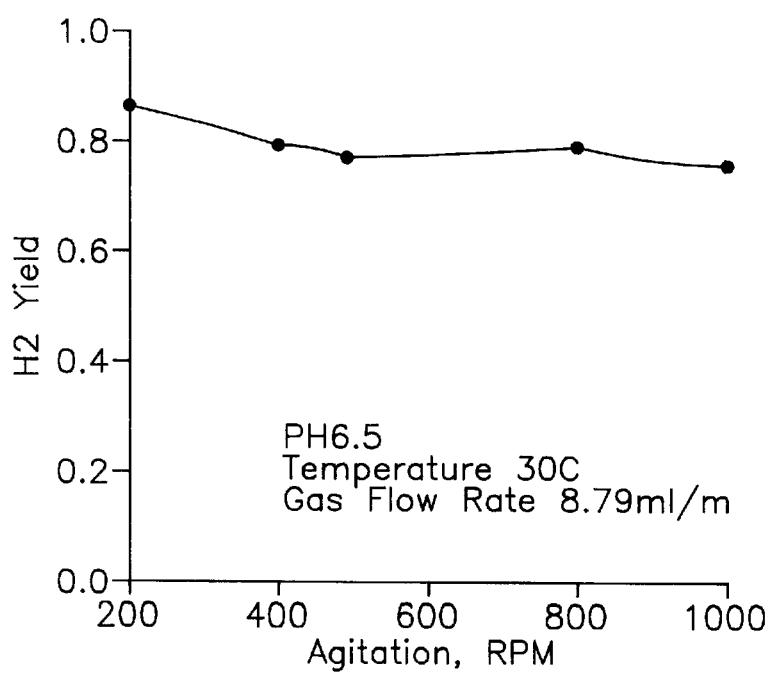
FIG. 36 $H_2$ Yield as a Function of Agitation in Continuous Culture with *R. rubrum* ATCC *25903*

FIG. 35 shows the CO conversion as a function of agitation rate for R. rubrum. The operating conditions included a 2.8 hr gas retention time, 8.6 day medium retention time (1800 ml culture), and steady state cell density of 2.5 g/L. As is shown in FIG. 35, the CO conversion increased from 50 to 90 percent as the agitation rate increased from 200 to 600 rpm. Further increases in the agitation rate above 600 rpm did not further enhance CO conversion. This phenomena indicates that the reaction is no longer mass transfer limited. FIG. 36 shows the $H_2$ yield as a function of agitation rate for R. rubrum in the CSTR. As expected, the yield was not affected by the agitation rate, and remained at about 80 percent.

Figure 37:
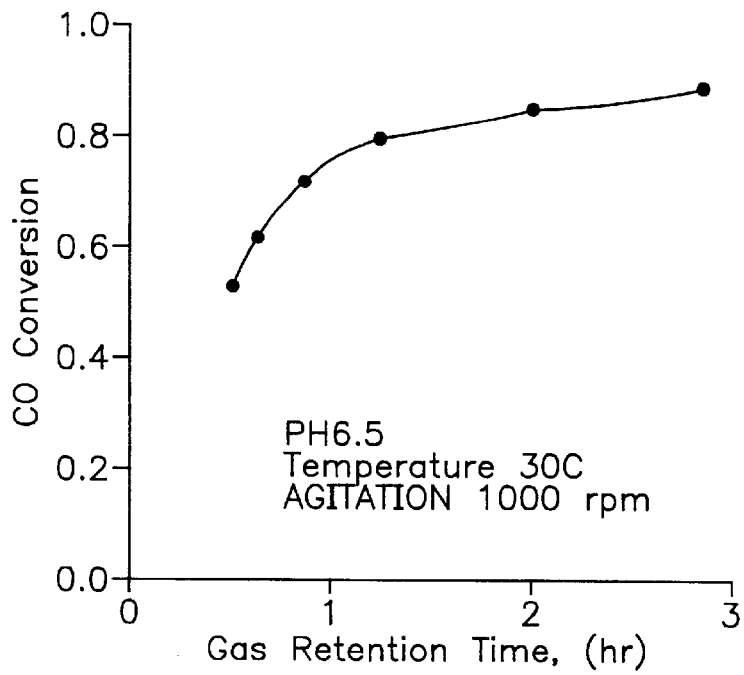
FIG. 37 CO Conversion as a Function of Gas Retention Time for *R. rubrum*

FIG. 37 shows the CO conversion and R. rubrum as a function of gas retention time with an agitation rate of 1000 rpm and an 8.6 day medium retention time. The conversion increased from 50 percent to 90 percent as the gas retention time increased from 0.5 hr to 3 hr.

Figure 38:
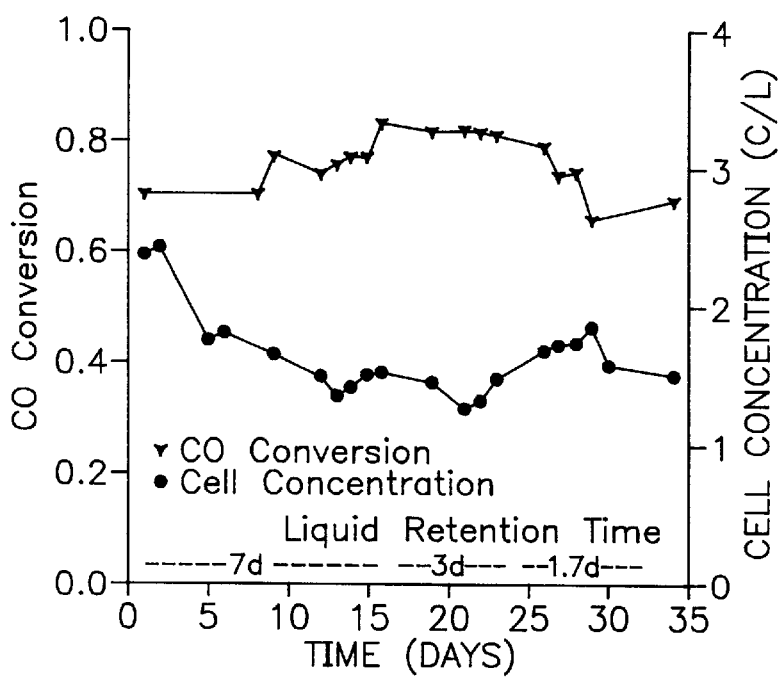
FIG. 38 Performance of CSTR with Varying Liquid Retention Time (*R. rubrum*)

FIG. 38 shows the CO conversion and R. rubrum cell concentration with varying medium retention time. The liquid retention time was controlled at 7, 3, and 1.7 days with the agitation rate at 1000 rpm and a gas retention time of 1 hr. As the average CO conversion was 75, 80, and 70 percent for 7, 3, and 1.7 days liquid retention times, respectively. The cell concentration reduced from 2.5 g/L to 1.5 g/L when the liquid flow rate was increased and the retention time was reduced to 1.7 days retention time.

Figure 39:
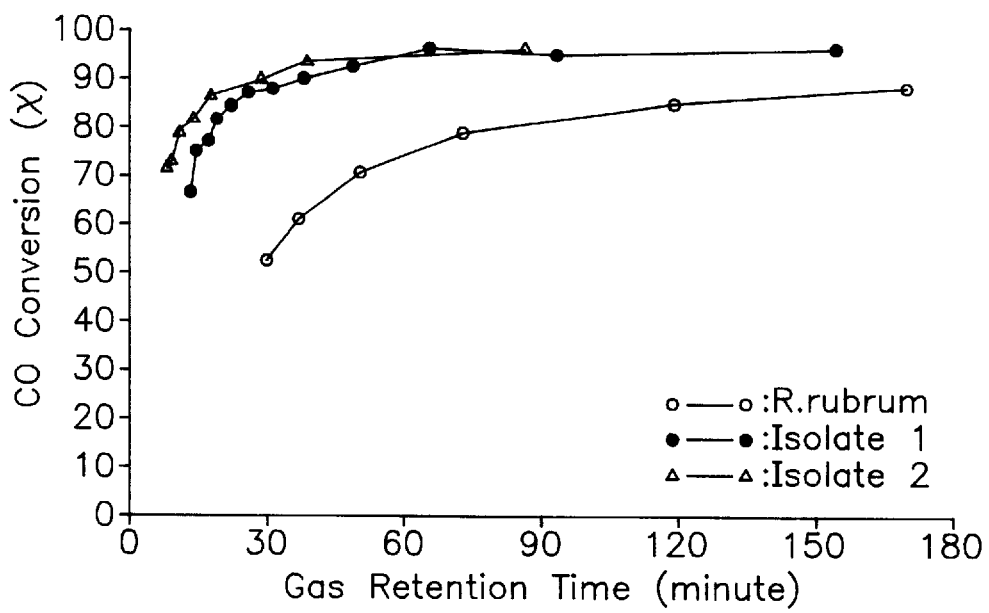
FIG. 39 Effect of Gas Retention Time on CO Conversion, 1000RPM

FIG. 39 shows a comparison of the effect of gas retention time on the CO conversion for R. rubrum and two ERIH2 enrichments (Isolates 1 and 2). The study was conducted at 1000 rpm, with semi-batch liquid for both ERIH2 enrichments. Table 11 shows the conversion for 10, 20, 30, 45, 60, and 90 minutes gas retention time. Obviously both enrichments converted CO much faster than R. rubrum. Isolate 2 shows slightly better performance in this preliminary study. The only problem with the enrichments is the very slow growth, especially for Isolate 1. In these experiments, the optical density for Isolate 1 was only about 0.2, much less than the 0.6 for Isolate 2 and the 3.5 for R. rubrum. Improvement of growth rates of the isolates will significantly improve performance.

Figure 40:
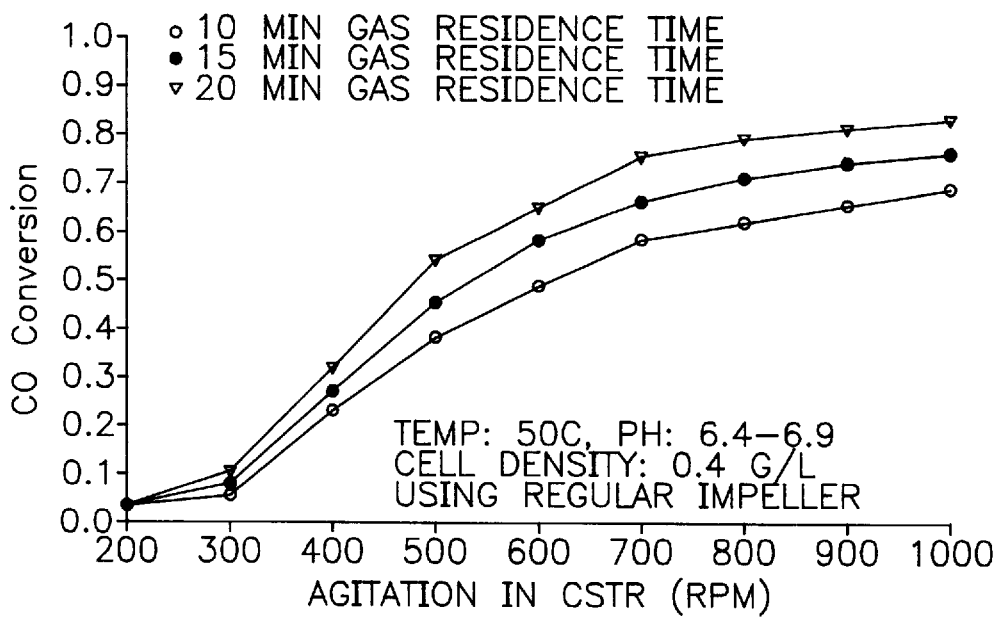
FIG. 40 The Effects of Agitation Rate and Gas Residence Time on CO Conversion in the CSTR by ERIH2

Experiments were continued with the ERIH2 isolates in the CSTR. To minimize the required reactor volume of the CSTR, the cell concentration was maximized. The addition of glucose stimulated growth; however, the reduction in pH from subsequent acid production significantly inhibited the gas utilization. Thus, pH control is essential in successful operation of the CSTR. The chemostat was supplied with 2 g/L glucose in the medium (Table 22) with a liquid retention time of 150 hr. A 1/4horsepower agitator was used in this study. The effect of agitation rate with a 10 to 20 minute gas retention time was studied. Table 12 summarizes the steady state CO conversion in this study. FIG. 40 shows CO conversion as a function of agitation and gas retention time. The $H_2$ yields were from 90 to 95 percent in these runs. As expected, higher agitation rates and longer gas retention times increased the conversion. The effect of agitation is significant and shows the mass transfer limitations of the fermentation. A doubling of agitation rate from 400 to 800 rpm doubles the conversion. Further increases do not have such a pronounced effect, however.

The major problem encountered in operating a CSTR with strain ERIH2 is the inability to maintain high cell concentrations inside the reactor. High cell densities typically translate into high reaction rates, and thereby minimize reactor volume for a given gas retention time. This problem was attacked by utilizing various concentrations of glucose as the substrate for growth and by employing cell recycle. Cell recycle allows a higher concentration of cells inside the reactor by separating the cells from the effluent and returning them to the reactor. For example, the liquid effluent from the reactor is passed to a centrifuge, hollow fiber membrane, or other filtration device to separate out microorganisms that are entrained. These microorganisms are returned to the bioreactor 18 to increase the microorganism concentration. In accordance with a particular example, the culture broth from the bioreactor is recycled through a cross-flow hollow fiber module by a peristaltic pump. The recycling rate is about 80–100 mL/min. The hollow fiber module has the following characteristics; the surface area is 0.35 ft$^2$, the pore size is 0.2 $\mu$ and the lumen diameter is 1 mm. The permeate from the fiber module is pumped to a storage tank. The culture cells from the fiber module are returned to the bioreactor.

In accordance with another example, a bench scale system operating with a CSTR and the anaerobic bacteria ERIH2, consists of a New Brunswick Scientific Bioflow IIc fermenter, a hollow fiber membrane unit for cell recycle, and extraction and distillation columns. Nutrient mixture is fed into the bioreactor at a rate of 3.2 cubic centimeters per minute. Capacity of the reactor is 2.5 liters, within which a constant fluid level of 1.5 liters is maintained. The fluid is agitated at variable rates of up to 1000 revolutions per minute with syngas introduced at a rate of approximately 500 cubic centimeters per minute. The syngas feed is varied with its uptake by the bacteria, which was in turn a function of the cell density. The liquid from the bioreactor is passed to the hollow fiber membrane at a rate of 55 to 70 milliliters per minute. From the hollow fiber membrane, permeate is gathered at a rate of 1 to 15 milliliters per minute. Culture cells and liquid is returned to the fermenter at a rate of 40 to 69 milliliters per minute.

Figure 41:
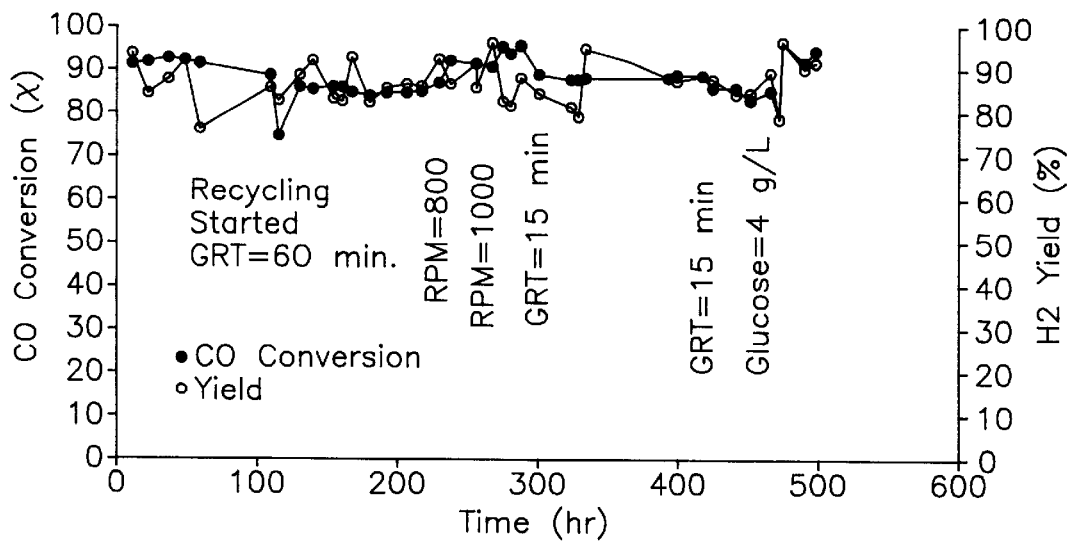
FIG. 41 CO Conversion and $H_2$ Yield by ERIH2 in the CSTR with Cell Recycle (2–4 g/L glucose)
Figure 42:
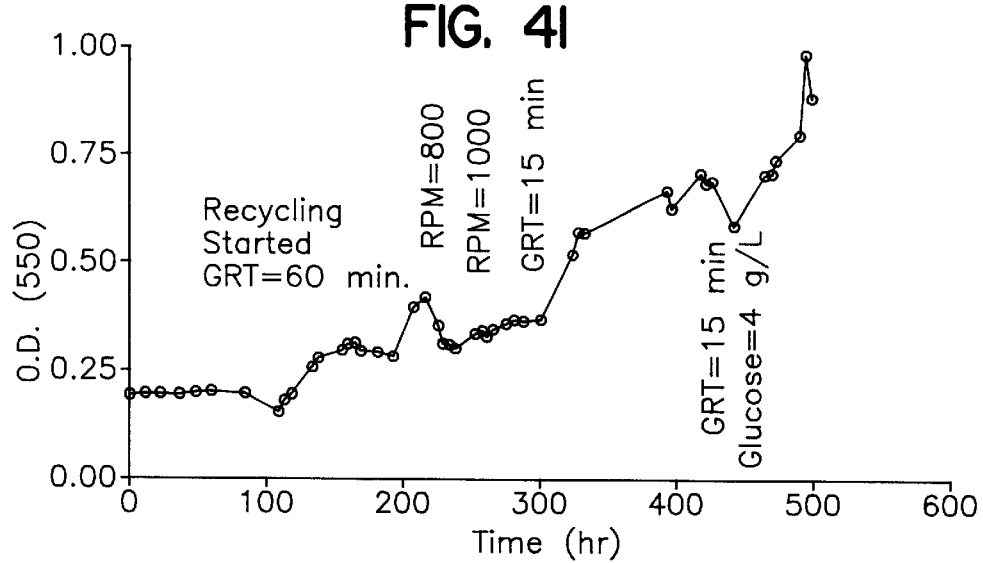
FIG. 42 Cell Growth (OD580) by ERIH2 in the CSTR with Cell Recycle (2–4 g/L glucose)
Figure 43:
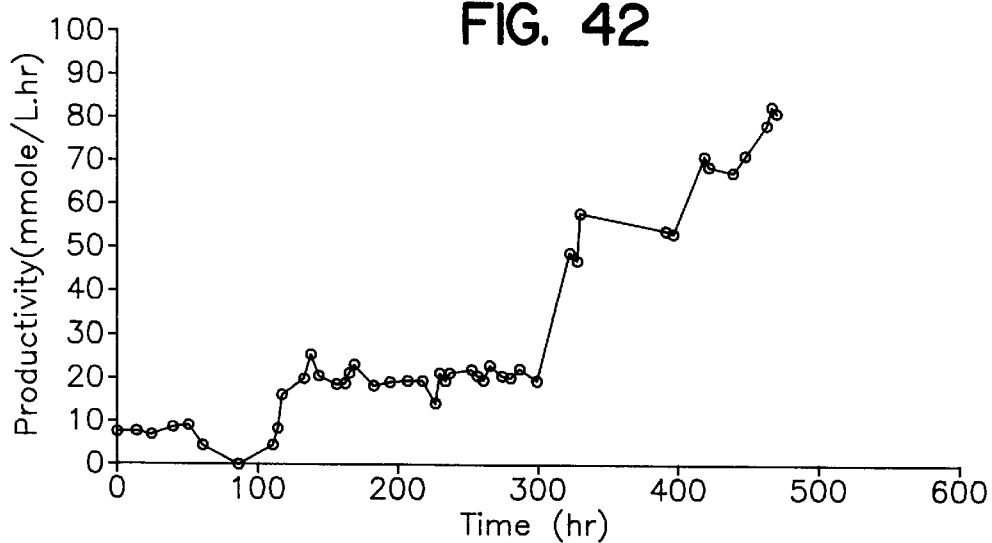
FIG. 43 $H_2$ Productivity of ERIH2 in the CSTR with Cell Recycle (2–4 g/L glucose)

FIGS. 41–43 show the performance of strain ERIH2 in the CSTR with cell recycle by plotting CO conversion, $H_2$ yield, optical density as a measure of cell concentration and reactor productivity as a function of time for various conditions in the reactor. The reactor was initially operated as a CSTR without recycle using 2 g/L glucose as the carbon source for growth. The gas retention time was 60 min at an agitation rate of 800 rpm. Cell recycle began after about 50 hrs of operation. Under these conditions, the steady state CO conversion was about 85 percent, the $H_2$ yield was 90–95 percent (FIG. 40), the cell concentration was 0.24 g/L (O.D.=0.3) (FIG. 41) and the $H_2$productivity was 20 mmole/L.hr (FIG. 42).

Figure 47:
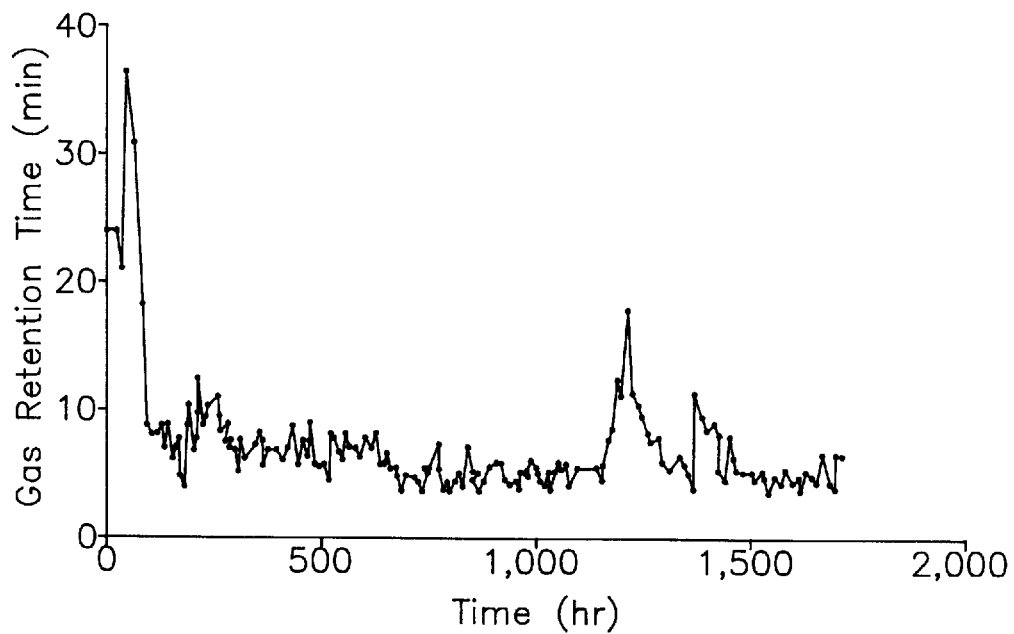
FIG. 47 Gas Retention Time Profile in the Immobilized Cell Reactor Using ERIH2

Several changes were made over the next 300 hr while still utilizing 2 g/L glucose. The agitation rate was changed to 100rpm at t=270 hr, and the gas retention time was lowered to 18 min at t=300 hr. During each of these changes the CO conversion and $H_2$ yield remained constant (FIG. 47), while the cell density steadily increased (FIG. 42). The optical density at 400 hr with a 15 min gas retention time was 0.7, over three times the initial value. The productivity also increased, reaching 50–60mmole/L.hr. (FIG. 43). When the glucose concentration was then raised to 4 g/L, the CO conversion was about 90 percent, the $H_2$ yield was 90–100 percent, the cell density was nearly 0.8 and the $H_2$ productivity was 80 mmole/L.hr.

Figure 44:
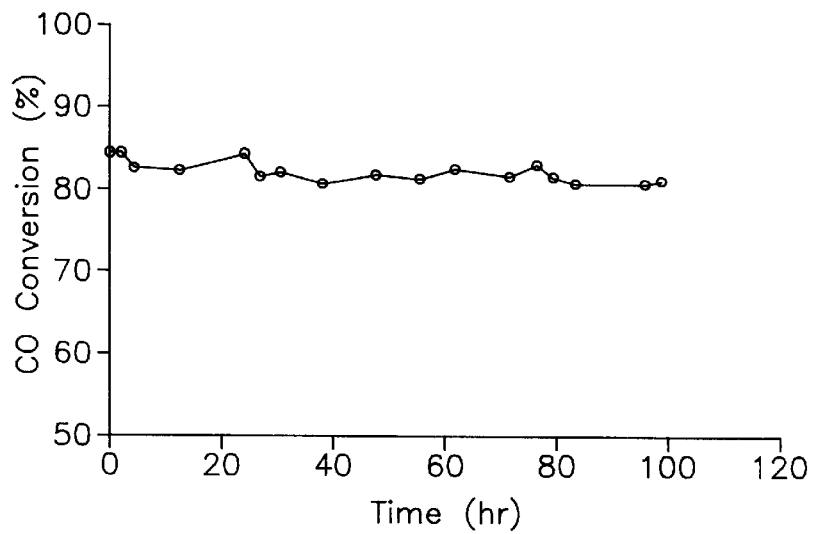
FIG. 44 CO Conversion by ERIH2 in the CSTR with Cell Recycle (1 g/L glucose)
Figure 45:
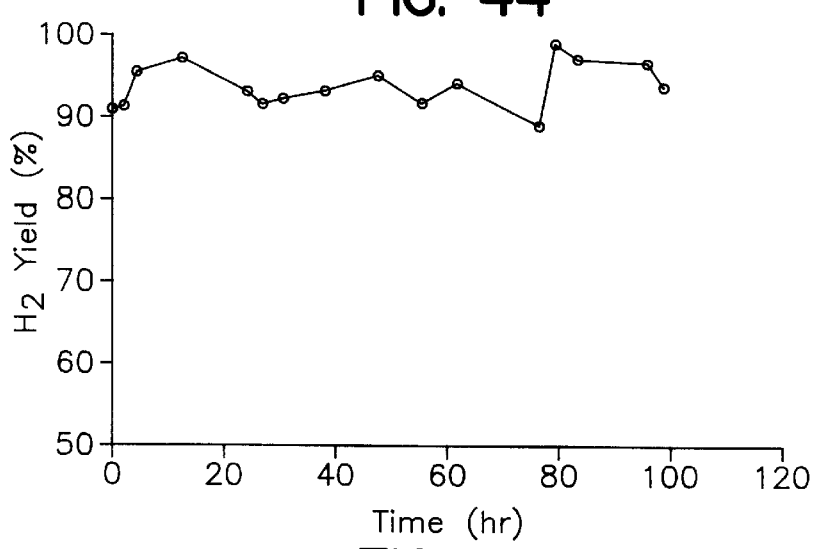
FIG. 45 $H_2$ Yield by ERIH2 in the CSTR with Cell Recycle (1g/L glucose)
Figure 46:
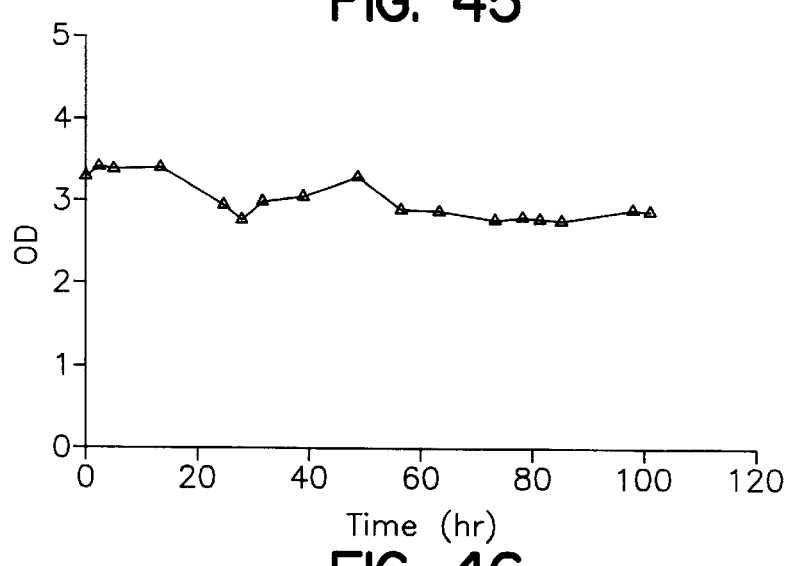
FIG. 46 Optical Density Measurements for ERIH2 in the CSTR with Cell Recycle (1 g/L glucose)

Based upon the success shown in FIGS. 41–43 with increasing glucose concentration, the concentration of glucose was further increased to 10 g/L. A tabulation of steady state data at this glucose concentration is shown in Table 13. The liquid dilution rate throughout the study was 0.026 hr$^{-1}$. As is noted in the table, the CO conversion decreased with gas retention time, ranging from 85 percent at a 21.6 min retention time to 79 percent at an 8.1 min retention time. The $H_2$ yield was 80–90 percent and the cell density was approximately 2.4(O.D.=3.0). The $H_2$ productivity increased with decreasing gas retention time, reaching a maximum of 134 mmole/L.hr. When the glucose concentration was again lowered to 1.0 g/L, the steady state CO conversion was 85 percent (FIG. 44), the $H_2$ yield was 100 percent (FIG. 45) and the cell density was 2.4 (FIG. 46). These latter measurements were obtained at a 21.6 min gas retention time, a 0.026 hr$^{-1}$ liquid dilution rate and 900 rpm.

It is interesting to note that the steady state conversions, yields and optical densities when using either 1 g/L or 10 g/L glucose were the same. The cell concentrations obtained in the CSTR/cell recycle system with 10 g/L glucose can apparently be viably sustained for long periods of time with the aid of cell recycle. A lower glucose feed concentration is thus possible.

The CSTR was operated without cell recycle in an effort to determine the effect of certain variables on the yield of cells from glucose. The reactor was first operated at a glucose concentration of 2 g/L, while varying the gas retention time and dilution rate. Table 14 shows preliminary results from this study. As is noted, the optical density is affected by increasing dilution rate, while the gas retention time affects CO conversion.

Experiments have been conducted with ERIH2 cells cross-linked to Ca-alginate to enable operating temperatures of 50° C. The culture was first centrifuged at 5000 rpm for 15minutes and the concentrated culture was washed with 35 ml of 0.9percent anaerobic NaCl solution. The concentrated culture solution was then mixed with an equal volume of 4 percent Na-alginate inside an anaerobic chamber. Calcium carbonate (0.79g) and glueanolactone (0.7 g) were added to the solution to form concentrated cell/gel beads. The cell/gel beads were maintained inside the anaerobic chamber for a few hours to dry and then placed into the column reactor. In the initial test, no solid support was provided. Without support, the beads deformed with the pressure of the fluid so that the column became plugged and even distribution of fluid could not be maintained. Therefore, subsequent experiments used sterilized 6 mm porcelain berl saddles as the support for the gel. With the gel on the surface of the saddles, the porosity of the column was maintained and flow problems were reduced. Operation of the column was satisfactory, although the volume of the support greatly increased the required retention time for a given conversion.

Finally, the performance of ERIH2 was demonstrated in an immobilized cell column reactor (ICR) packed with 4–12 mesh activated carbon. The total column volume was 635 mL and the column void volume was 265 mL. The temperature of the system was held constant at 50° C. and the liquid flow rate to the system was maintained at 0.4 mL/min. The gas retention time (based on void volume), shown in FIG. 47 as a function of operating time, was generally 5–10 hr, except during start-up and during a brief interruption in operation at t=1200 hr. The glucose concentration fed to the reactor to maintain growth was 6 g/L during the first 1000 hr of operation, was increased to 10 g/L during the next 200 hr, was decreased to 2 g/L for a short recovery period and was finally increased back to 6 g/L for the balance of the study.

Figure 48:
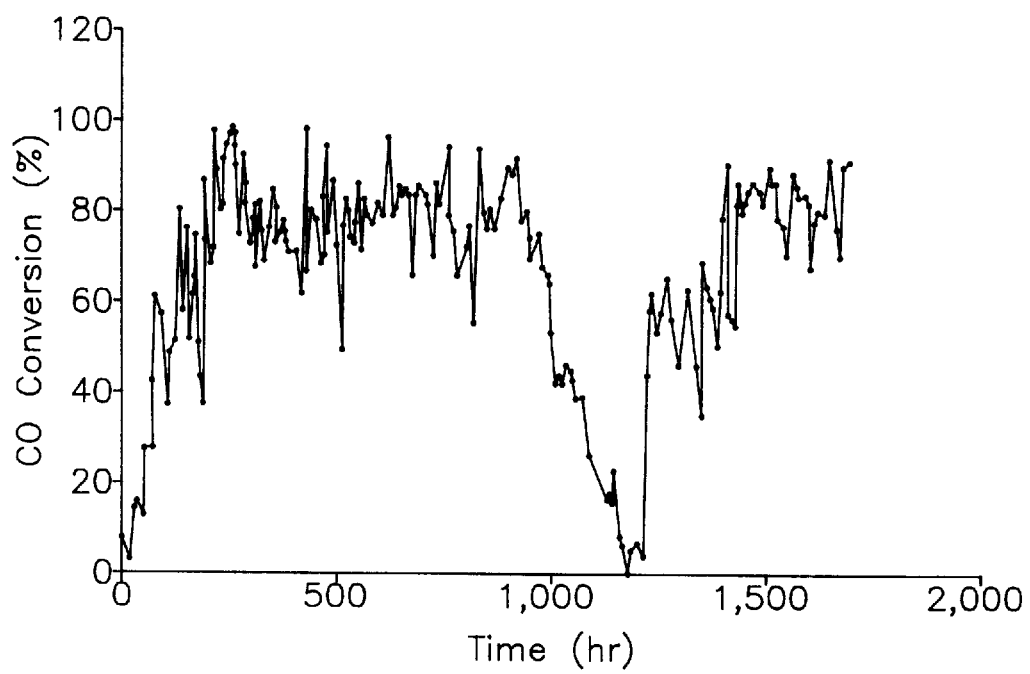
FIG. 48 CO Conversion in the Immobilized Cell Reactor Using ERIH2
Figure 49:
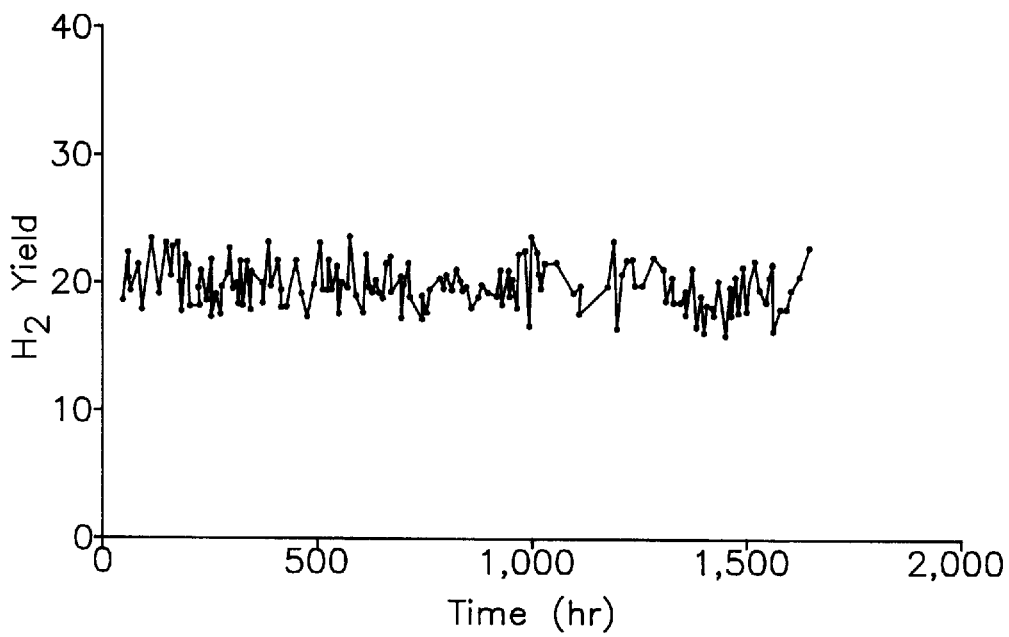
FIG. 49 $H_2$ Yield from CO in the Immobilized Cell Reactor with ERIH2

FIG. 48 shows the CO conversion profile in the reactor with time. The CO conversion was 80 percent or greater except during the upset at 1200 hr when the glucose concentration in the feed was too high. Since cells were accumulating in the reactor with time (as evidenced by the visual appearance of cells), it is noted that cell concentration had little to no effect on CO conversion at a given retention time. This surprising result was also seen in the CSTR studies (see Table 12), where CO conversions of 90–100 percent were seen at all retention times studied. Similarly, the yield of $H_2$ from CO, shown in FIG. 49, was constant at 1.0 (theoretical) regardless of the experimental conditions.

In comparing the immobilized cell reactor (ICR) with the CSTR with cell recycle (Table 13), it is seen that an 80 percent conversion of CO to $H_2$ can be obtained at a 10 min gas retention time in the CSTR with cell recycle. The $H_2$ productivity in the CSTR system was about 100 mmol/L-hr. In the immobilized cell reactor, an 80 percent CO conversion was attained at a 5 min gas retention time based on void volume, or a 12 min gas retention time based on total column volume. The productivity in the ICR was 270 mmole/L-hr based on void volume and 110 mmol/L.hr based on total column volume. The immobilized cell rea ctor is thus a suitable substitute for the CSTR with cell recycle and has the advantage of not requiring agitation.

Trickle bed reactors (TBR) are effective in promoting gas-liquid mass transfer and thus are ideal for this application. Mass transfer is effected by flowing (or trickling) a small stream of liquid over an inert packing while simultaneously flowing gas either concurrently or countercurrently. For a biological system, the liquid contains cells in addition to liquid medium. Also, the column is operated concurrently, which is a superior operating mode for irreversible biological reactions.

Figure 50:
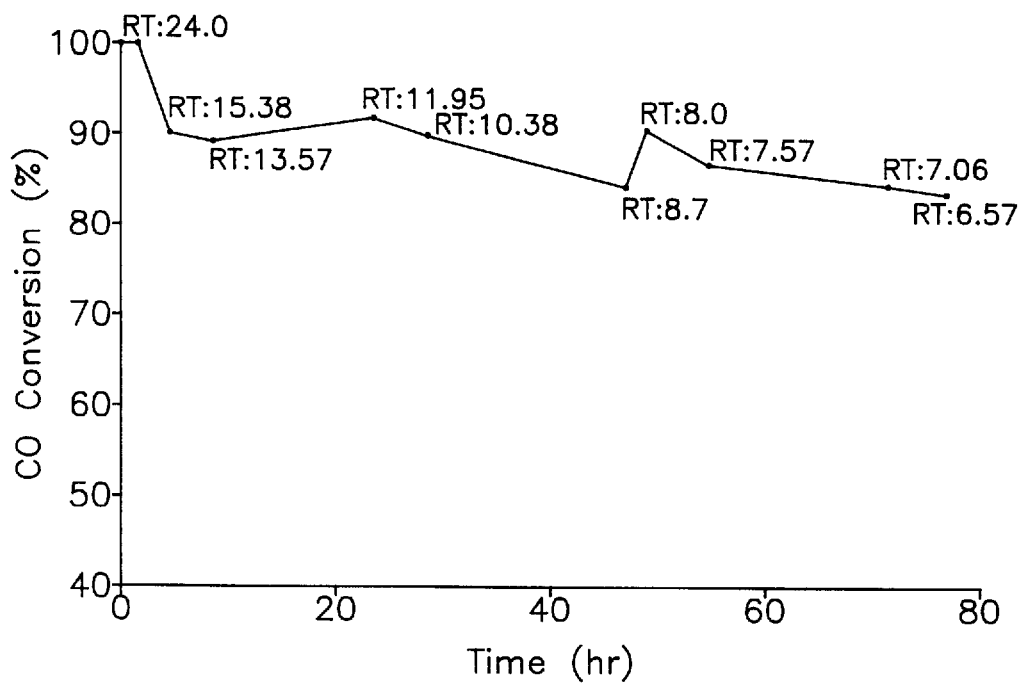
FIG. 50 CO Conversion in the Trickle Bed Reactor with ERIH2(2 g/L glucose)
Figure 51:
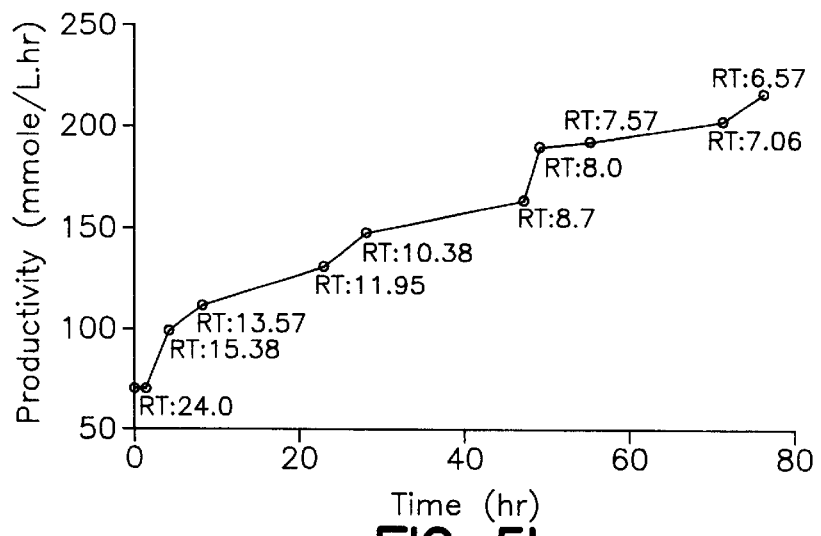
FIG. 51 $H_2$ productivity, Trickle Bed Reactor with ERIH2 (2g/L glucose)

FIGS. 50 and 51 present CO conversion and $H_2$, productivity data for the trickle bed reactor using ERIH2 at various gas retention times. All experiments were carried out at a 2 g/L glucose concentration, with 1 g/L yeast extract and 1 g/L trypticase in the medium. As the retention time decreased, the productivity increased (FIG. 51), while the CO conversion remained in the 80–100 percent range (FIG. 50). A summary of the trickle bed reactor data is shown in Table 15. Both the gas flow rate (gas retentions time) and liquid flow rate were changed during the study. As is shown in the table, the $H_2$ productivity (based upon liquid volume in the reactor) was 69–216 mmole/L.hr. This compares quite favorably with the CSTR productivities of 70–80 mmol/L.hr when the volume of the packing in the trickle bed is considered.

Reaction rate has been shown to be proportional to pressure for many organisms catalyzing gas-liquid reactions. More significantly, the size of the reactor in processing a given quantity of gas is inversely proportional to pressure. It is thus economically advantageous to operate at elevated pressures for these gas-liquid biological systems.

Experiments were carried out with ERIH2 in a batch high pressure Parr reaction vessel. Glucose (0.9 g/L) in combination with trypticase (1 g/L) and yeast extract (1 g/L), was added as the growth substrate. The key to success in these high pressure studies is to maintain a high cell concentration in the reactor in order to keep the dissolved CO tension (concentration) low. Since ERIH2 does not utilize CO for growth, an adequate carbon source (glucose) concentration must be present to keep the cell density high, especially when the pressure driving force is high.

Figure 52:
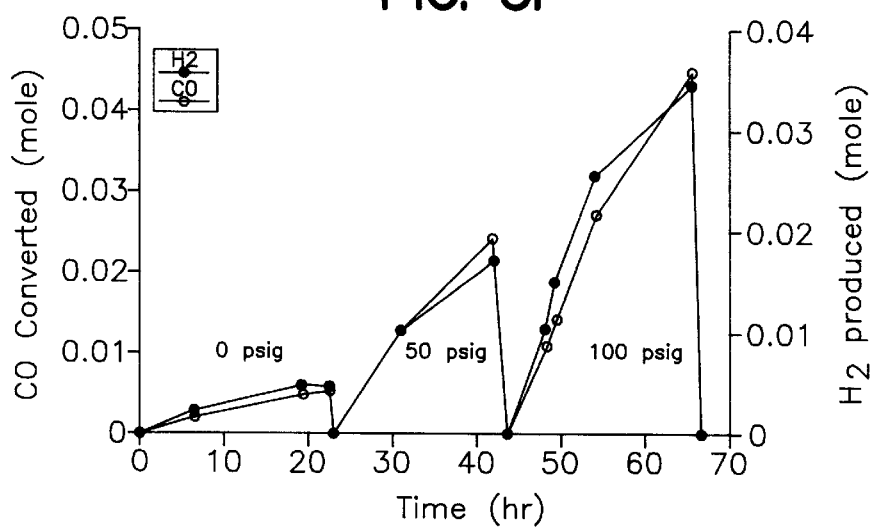
FIG. 52 CO Conversion and $H_2$ Production by ERIH2 in the High Pressure Parr Reactor (0.9 g/L glucose)
Figure 53:
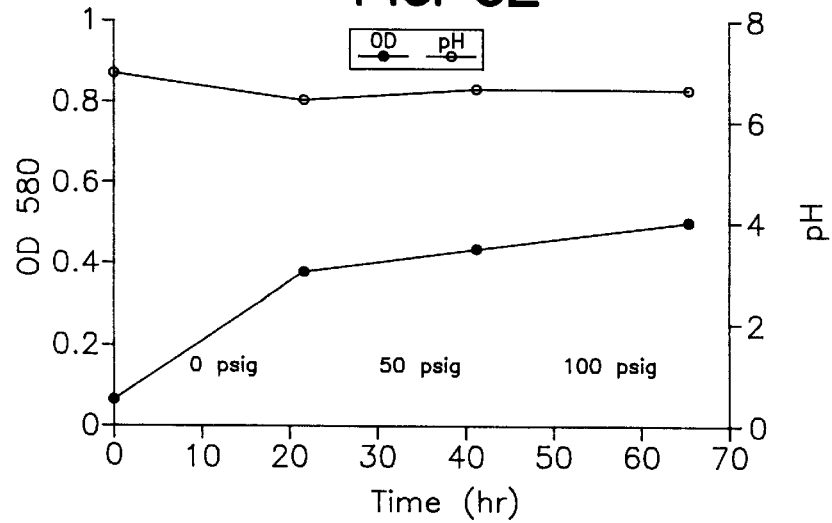
FIG. 53 Optical Density and pH Measurements in the High Pressure Parr Reactor with ERIH2 (0.9 g/L glucose)
Figure 54:
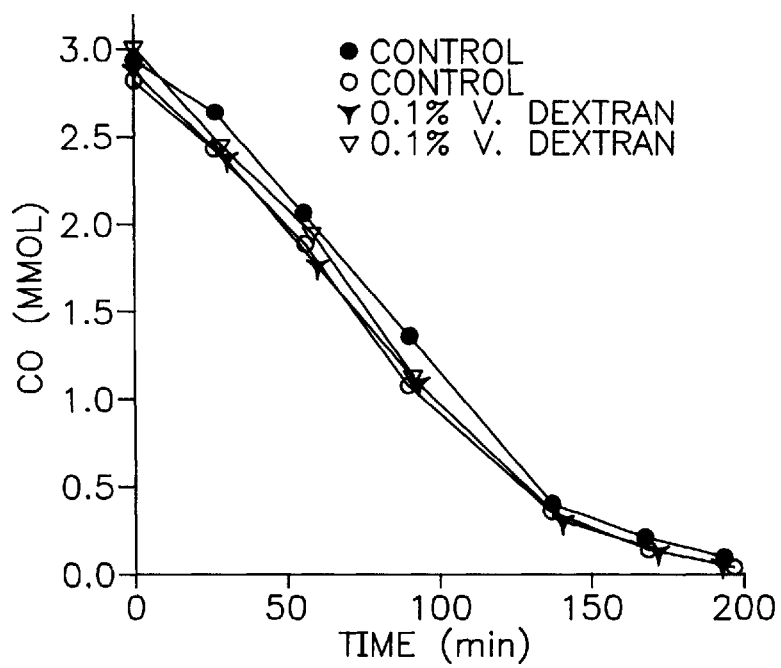
FIG. 54 The Effect of Dextran on CO Consumption
Figure 55:
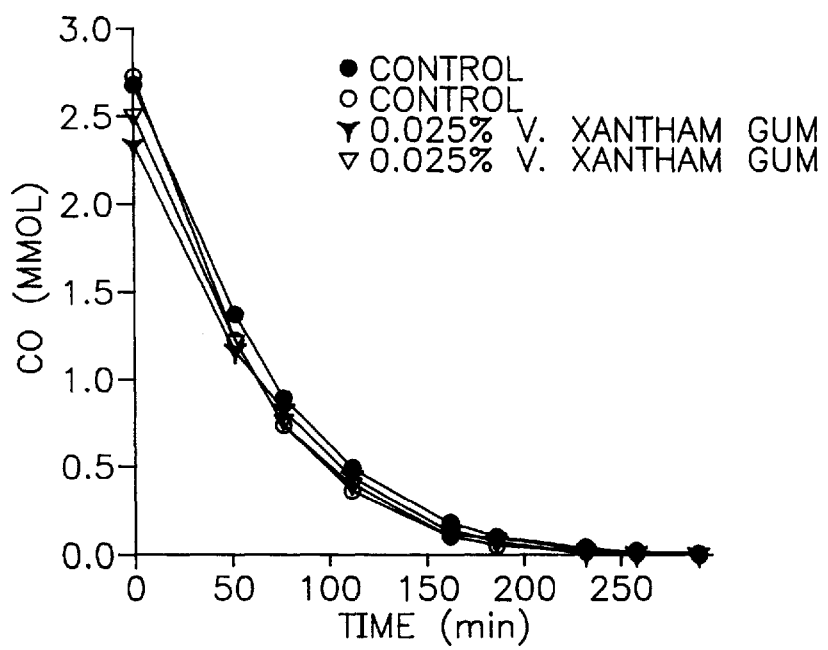
FIG. 55 The Effect of Xantham Gum on CO Consumption
Figure 56:
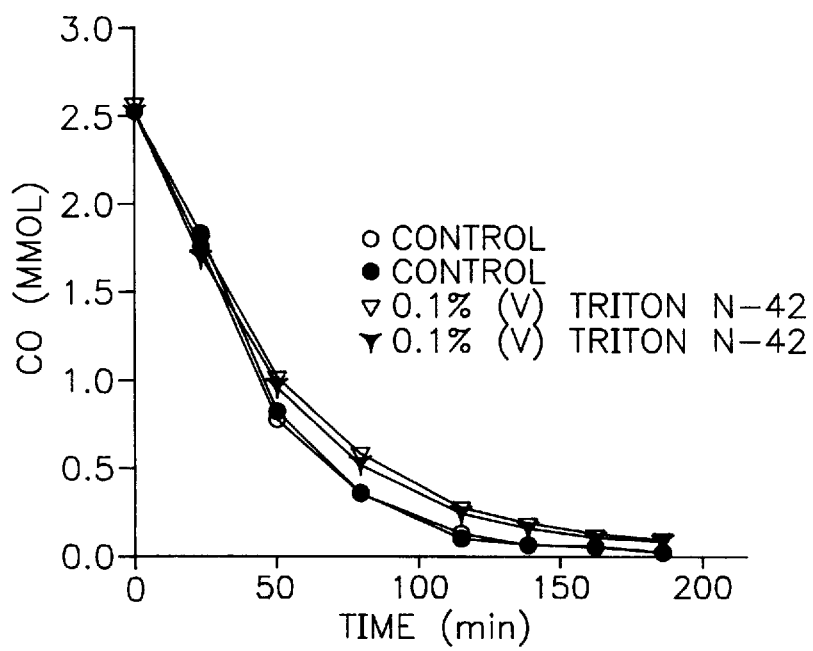
FIG. 56 The Effect of Triton N-42 on CO Consumption
Figure 57:
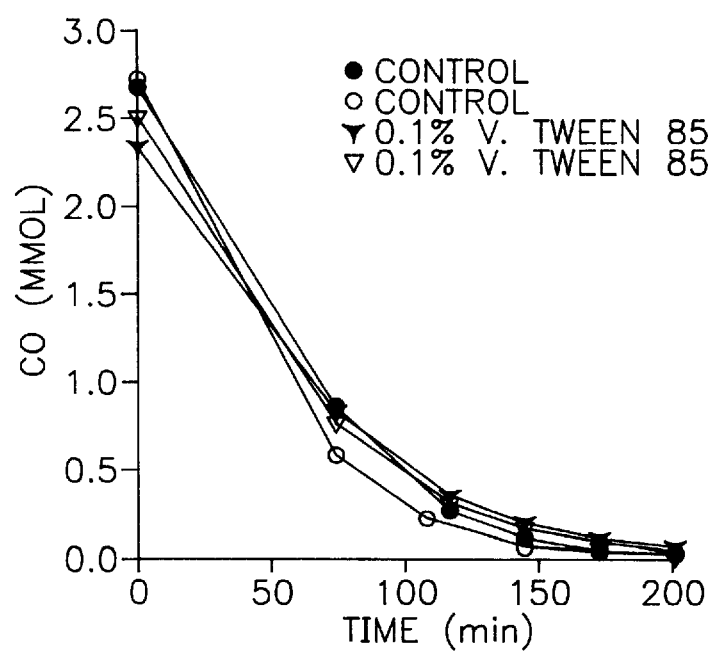
FIG. 57 The Effect of TWEEN-85™ detergent on CO Consumption
Figure 58:
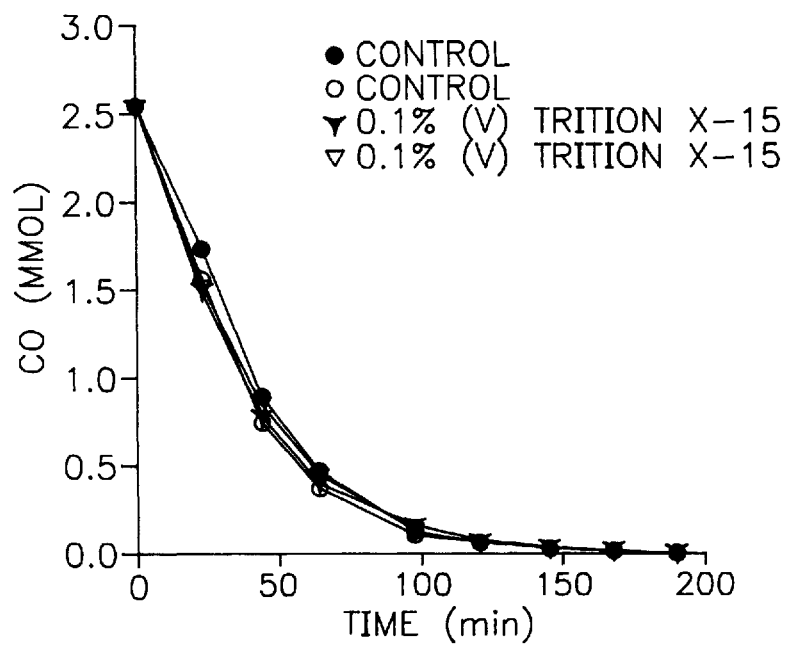
FIG. 58 The Effect of TRITON X-15™ detergent on CO Consumption
Figure 59:
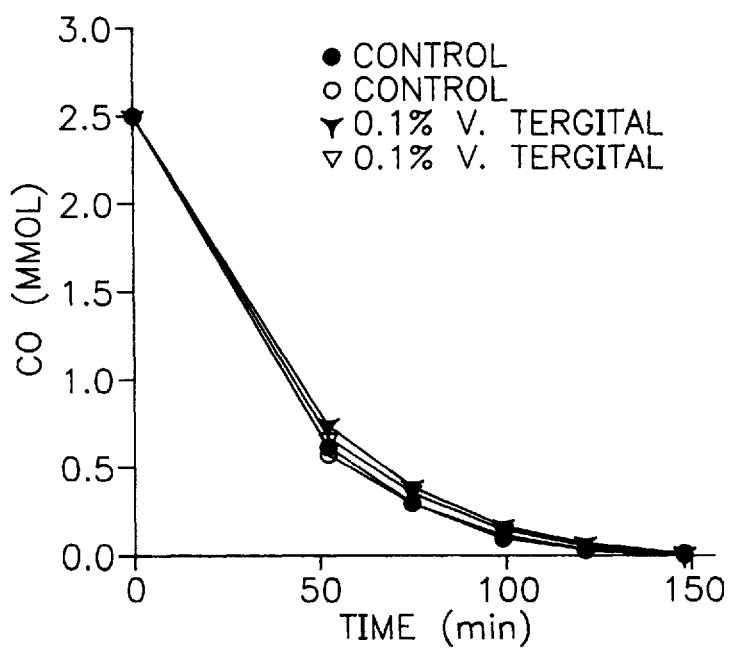
FIG. 59 The Effect of TERGITAL ™ detergent on CO Consumption
Figure 60:
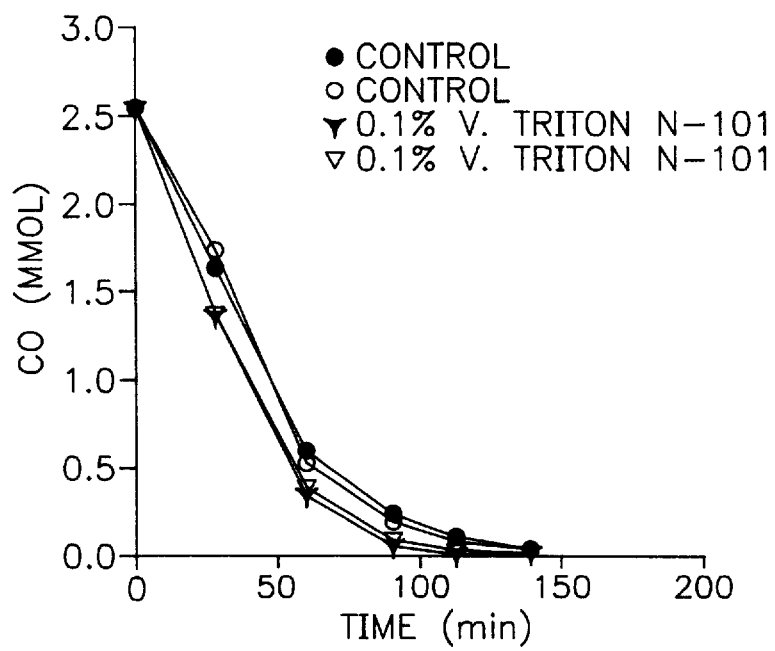
FIG. 60 The Effect of TRITON N-101™ detergent on CO Consumption
Figure 61:
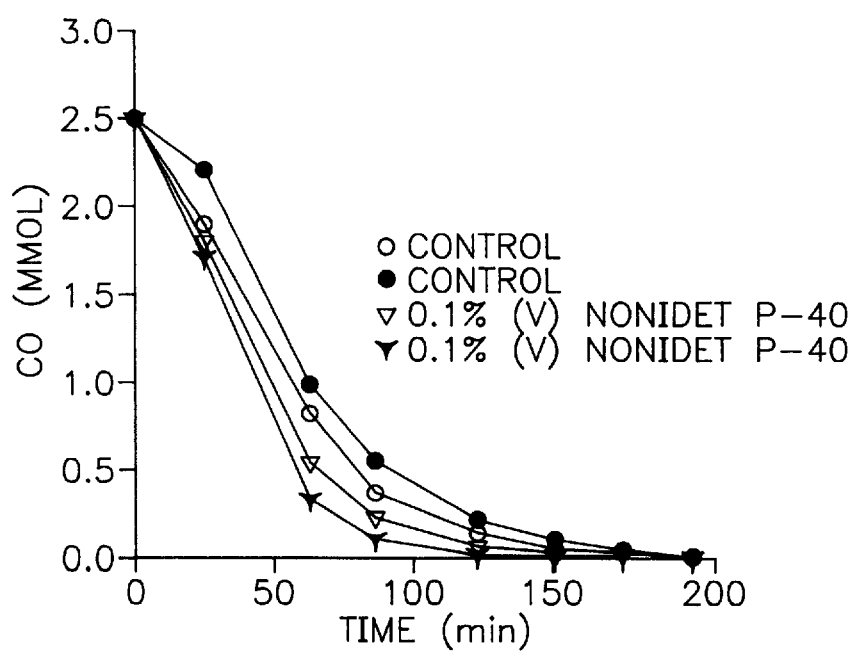
FIG. 61 The Effect of NONIDET P-40198 detergent on CO Consumption
Figure 62:
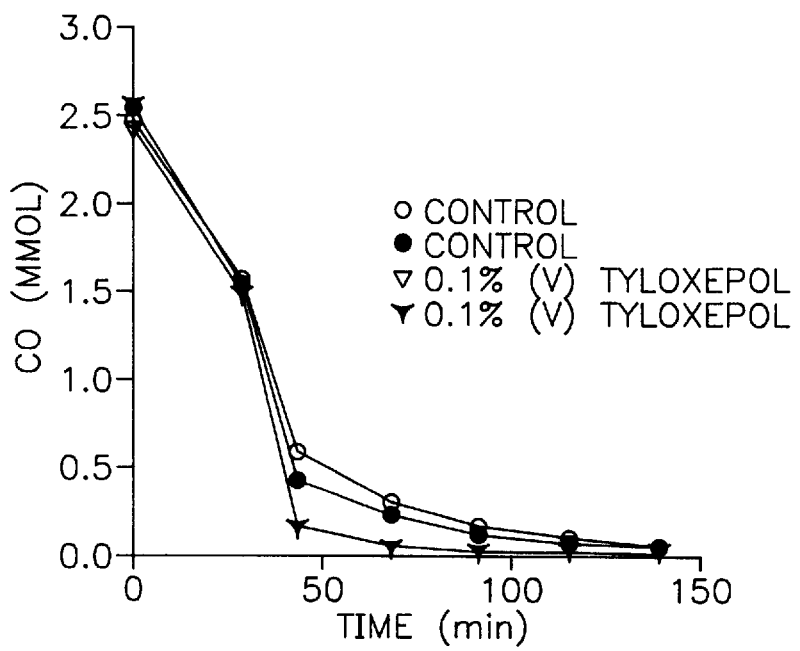
FIG. 62 The Effect of TYLOXAPOL™ detergent on CO Consumption
Figure 63:
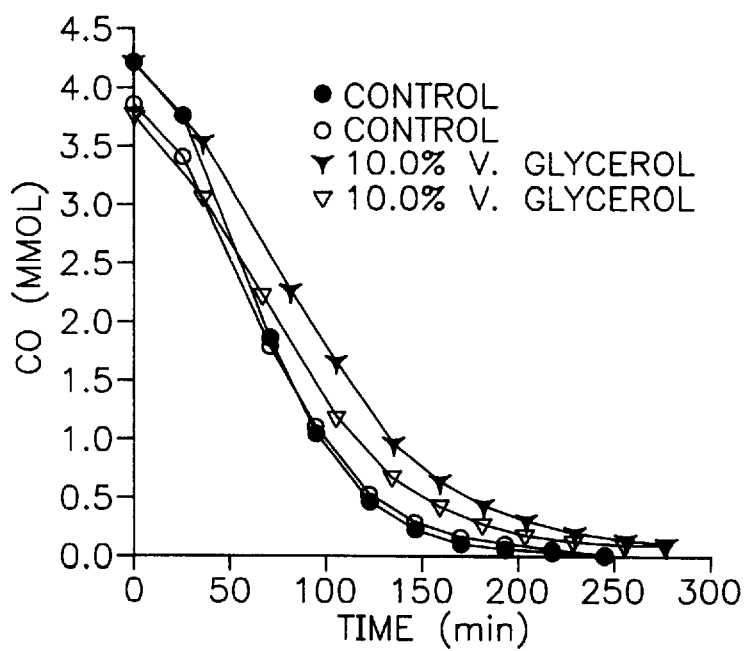
FIG. 63 The Effect of Glycerol on CO Consumption
Figure 64:
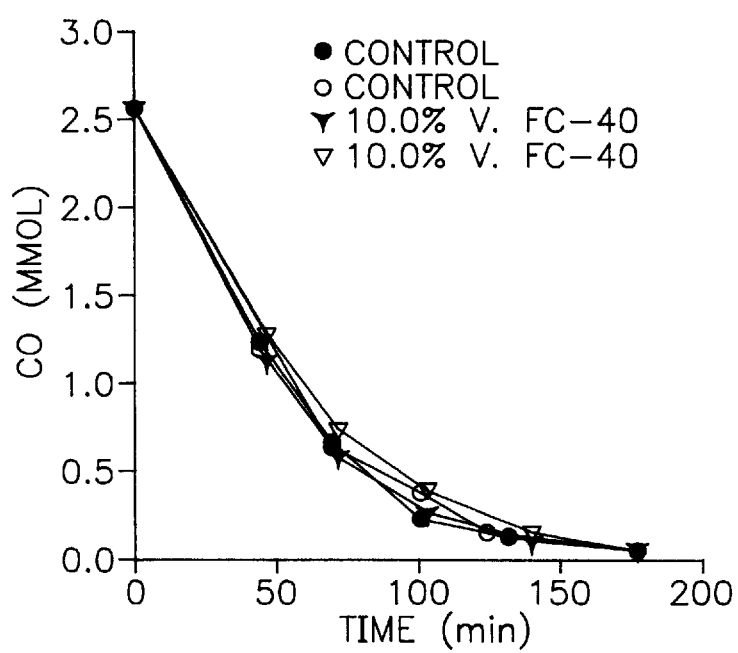
FIG. 64 The Effect of FC-40™ detergent on CO Consumption
Figure 65:
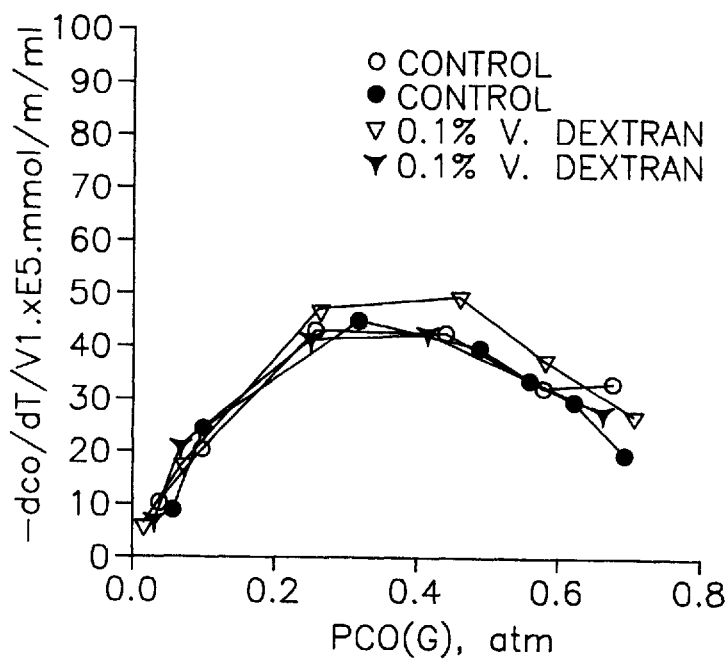
FIG. 65 Determination of Mass Transfer Coefficient Kla/H Plot Using Dextron at 0.1% V. Concentration FIG. 66 Determination of Mass Transfer Coefficient Kla/H Plot Using Xantham Gum at 0.25% V. Concentration FIG. 67 Determination of Mass Transfer Coefficient Kla/H Plot Using Triton N-42 at 0.1% V. Concentration FIG. 68 Determination of Mass Transfer Coefficient Kla/H Plot Using TWEEN-85198 detergent at 0.1% V. Concentration FIG. 69 Determination of Mass Transfer Coefficient Kla/H Plot Using TRITON X-15™ detergent 0.1% V. Concentration FIG. 70 Determination of Mass Transfer Coefficient Kla/H Plot Using TERGITOL™ detergent at 0.1% V. Concentration FIG. 71 Determination of Mass Transfer Coefficient Kla/H Plot Using TRITON N-101™ detergent at 0.1% V. Concentration FIG. 72 Determination of Mass Transfer Coefficient Kla/H Plot Using NONIDET P-40™ detergent at 0.1% V. Concentration FIG. 73 Determination of Mass Transfer Coefficient Kla/H Plot Using TYLOXAPOL™ detergent at 0.1% V. Concentration FIG. 74 Determination of Mass Transfer Coefficient Kla/H Plot Using Glycerol at 10% V. Concentration FIG. 75 Determination of Mass Transfer Coefficient Kla/H Plot Using FC-40™ detergent at 10% Concentration FIG. 76 The Effect of Tyloxapol on CO Conversion by ERIH2 in the CSTR FIG. 77 Effect of EMCOL CNP-110™ detergent on CO Conversion by ERIH2 in the CSTR FIG. 78 Gas Phase Partial Pressure Profiles for ERIH2 in Batch Culture FIG. 79 Determination of Mass Transfer Coefficient in the Batch Bottle Experiments FIG. 80 Liquid Phase CO Tension Profile for ERIH2 Obtained in Batch Culture FIG. 81 Determination of Monod Relationship for ERIH2.
Figure 66:
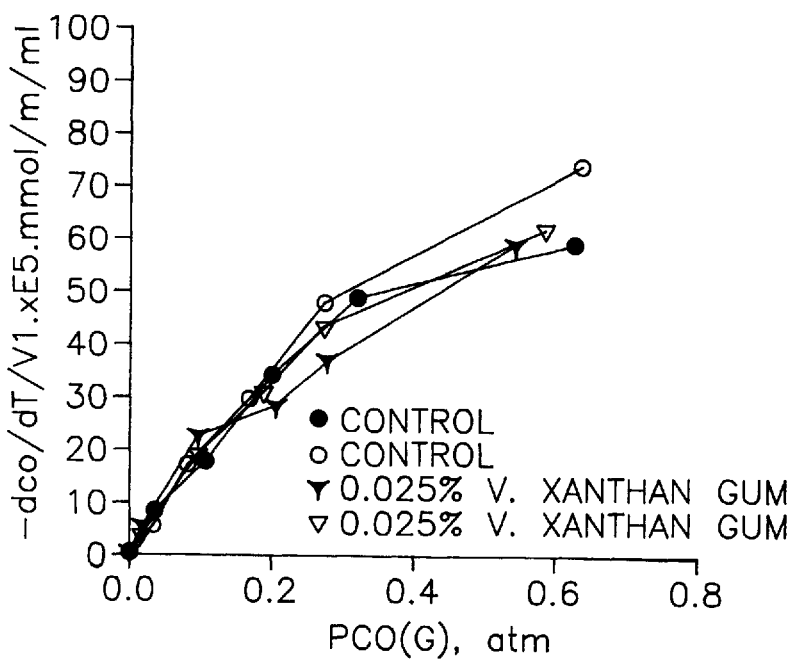
Figure 67:
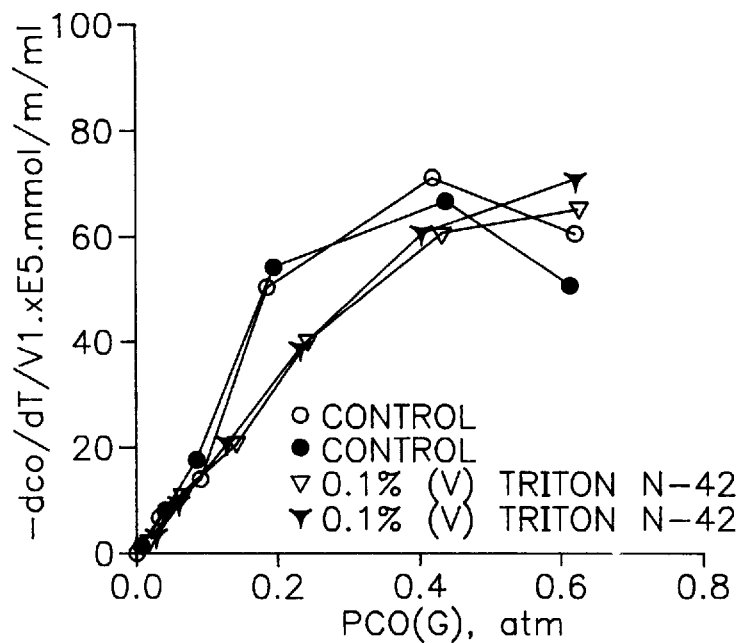
Figure 68:
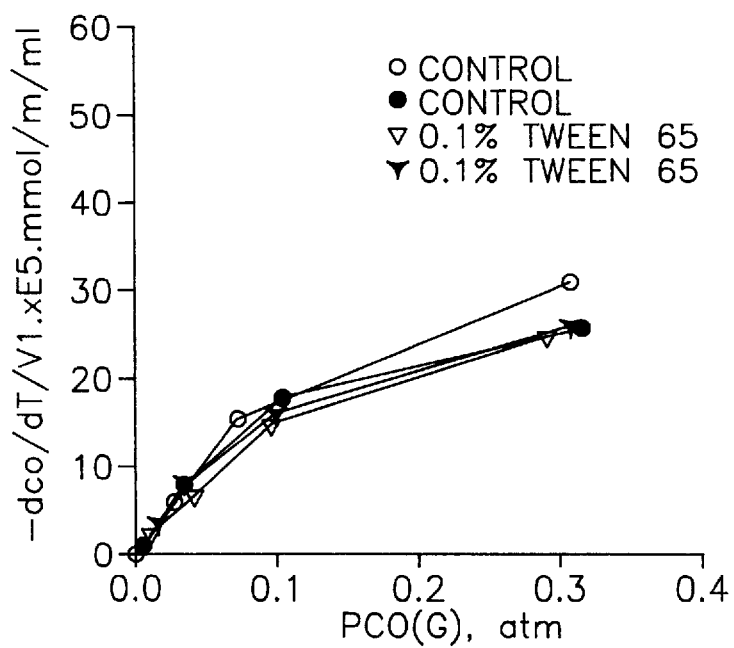
Figure 69:
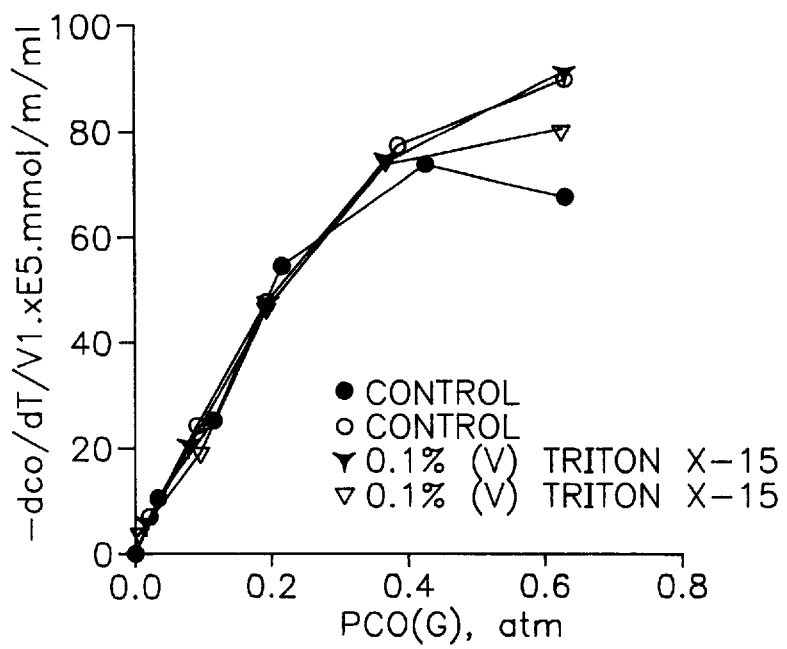
Figure 70:
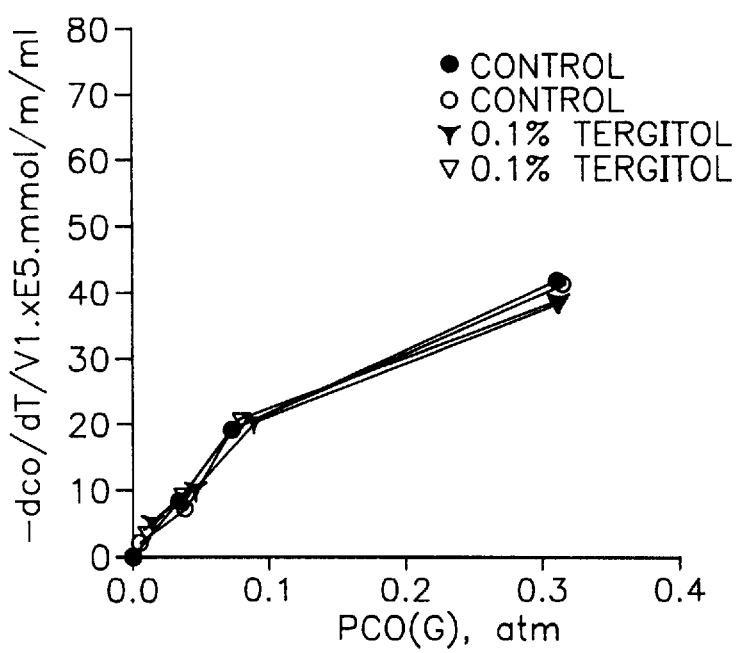
Figure 71:
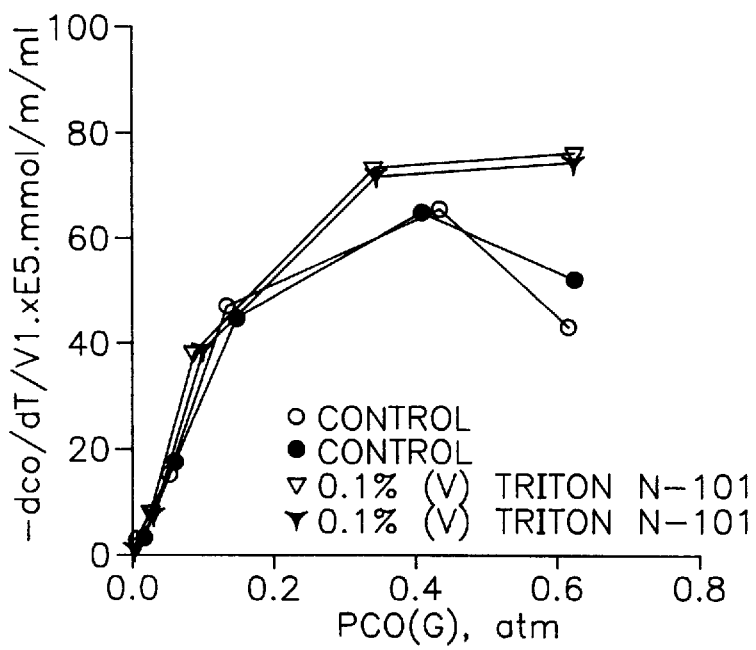
Figure 72:
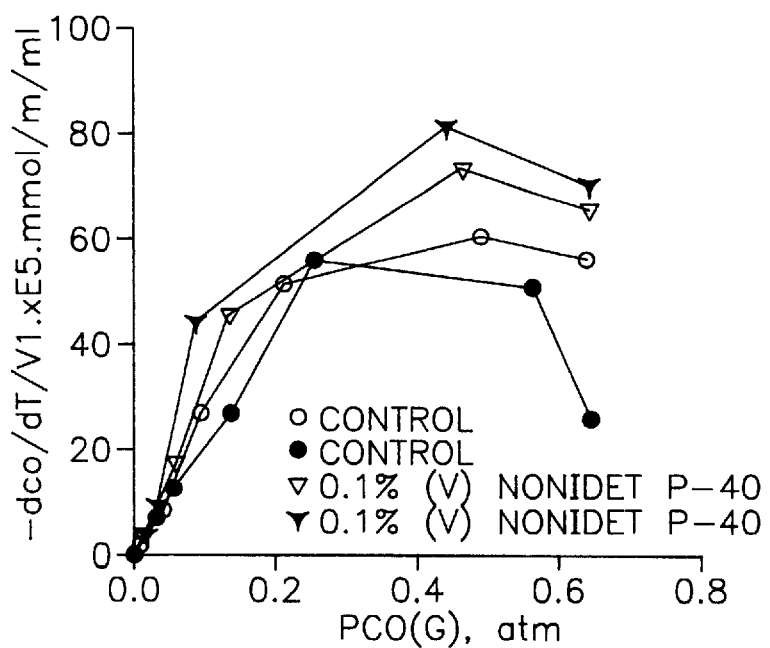
Figure 73:
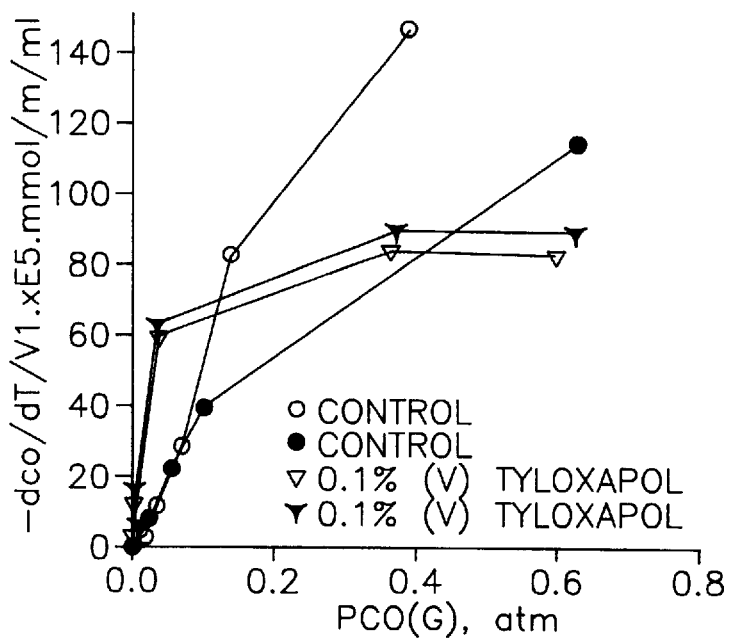
Figure 74:
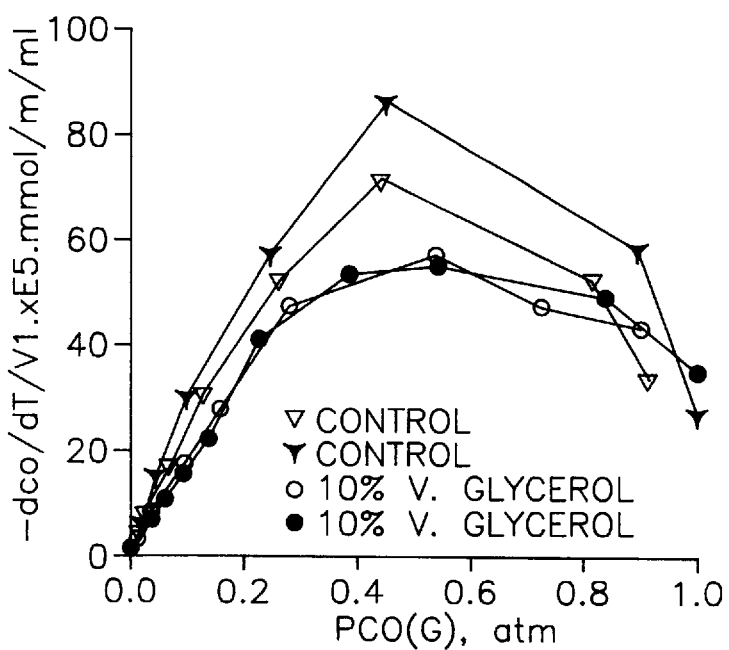
Figure 75:
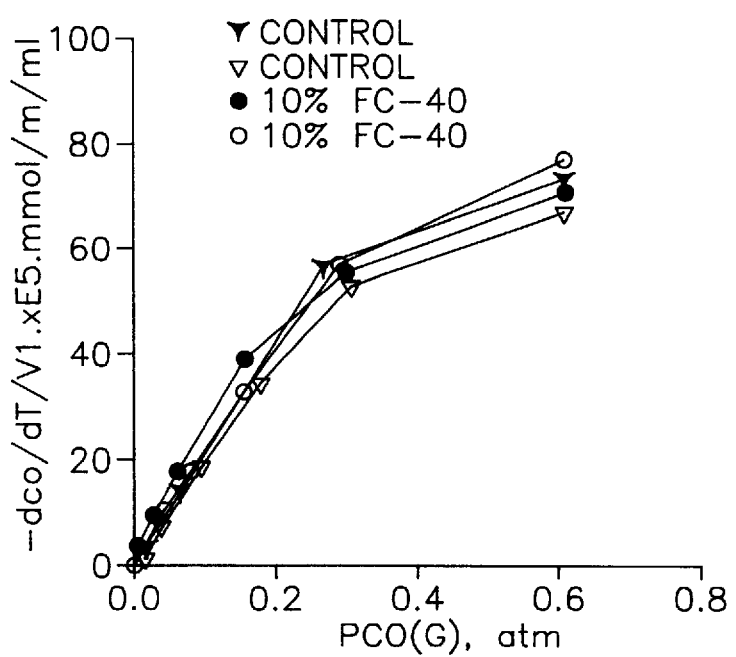

FIGS. 52 and 53 show CO conversion, $H_2$ production and optical density measurements for ERIH2 in the high pressure Parr reactor. The bacterium was able to utilize syngas at pressures as high as 100 psig. During the course of the experiment the rate of conversion of CO increased, as denoted by the increase in slopes in FIG. 52 with increased pressure. This indicates that operation at higher pressures is quite possible. $H_2$ production improved CO utilization as predicted by reaction stoichiometry. FIG. 53 shows that the pH dropped only slightly, perhaps because of the production of a by-product (maybe acetic acid) as the glucose was consumed for cell growth. The optical density rose from an initial level of 0.08 to 0.5.

Non-aqueous fermentation studies were conducted to enhance the mass transfer rate of the gaseous substrate, either by increasing the gas solubility or by reducing the mass transfer resistance through reduced surface tension at the gas-liquid interface. There is no information in the literature concerning the increase in CO solubility in the aqueous phase or reducing the mass transfer resistance of CO. The selection of chemicals for the study is based on the following criteria:

(1) Chemicals that can be dissolved into the aqueous phase.

(2) Chemicals with low toxicity, especially bio-products.

(3) Chemicals that can reduce the surface tension, which would increase the overall mass transfer rate.

Potential chemicals are bio-polymers, bio-surfactants, and metabolism reactants or products. Other possibilities are perfluorocarbons which have been reported to enhance $O_2$ transport into the aqueous phase. The study of the non-aqueous additives was separated into two stages: initial screening and CSTR studies. The initial screening studies were conducted in batch culture and only those materials showed good potential were studied later in the CSTR.

The identification of the increase of the CO solubility/mass transfer rate in batch culture is based on the CO consumption under mass transfer limited conditions. The gas phase CO material balance in the batch reactor can be described as follows:

$$\frac{1}{V_L} \frac{dN^G_{CO}}{dt} = \frac{K_L a}{H} (P^G_{CO} - P^L_{CO}) \quad (4)$$

The rate of disappearance of CO from the gas phase, $dN^G_{CO}/dt$, per unit of liquid volume, $V_L$, is proportional to the difference between the CO partial pressure in the gas and liquid phases, $P^G_{CO}$-$P^L_{CO}$ The proportionality constant is the mass transfer coefficient, $K_L a$, divided by Henry's Law constant, H, for CO. During the course of a batch fermentation, the reaction is begun with a high gas consumption. Eventually the reaction enters mass transfer limited conditions as $P^L_{CO}$ approaches zero. Under these conditions, the dissolved CO substrate cannot satisfy the bacterial consumption rate. Simultaneous cell growth with gas consumption is not needed to reach mass transfer limitations, although the time is shortened with cell growth. Under mass transfer limitations, $P^L_{CO}$ becomes zero and a plot of $dN^G_{CO}/dt$ verses $P^G_{CO}$ is linear through the origin, with a slope of $K_L a/H$.

This concept was used to evaluate the effect of adding chemicals to enhance CO solubility and gas transport. In the batch screening, the CO gas consumption is frequently monitored, especially in the later stages of the fermentation, in both amended and control runs. The gas consumption is computed and the value of $K_L a/H$ obtained as the slope of the plot of gas consumption rate and composition. The effect of solvent and chemical addition on CO utilization can be evaluated by comparing the values of $K_L a/H$. Since the Henry's law constant is defined as the solute partial pressure in the gas phase per unit concentration of the solute in the liquid phase, the smaller the value of H, the higher the gas solubility. Thus, larger values of $K_L a/H$ represent higher CO solubilities when mass transfer coefficients are the same. Similarly, for chemicals that do not affect solubility, higher $K_L a/H$ values show increased mass transfer rates.

In some cases, the mass transfer coefficient, $K_L a$, may be affected by the additive. The viscosity could be increased by the addition of a bio-polymer and $K_L a$ could be reduced. The mass transfer coefficient could be increased by the addition of a surfactant to reduce the surface tension. Under these conditions, the effect on CO solubility may be difficult to assess. However, $K_L a/H$ is still the proper indicator for selecting chemicals for non-aqueous fermentation.

Several chemicals were tested in batch culture. They include bio-polymers, bio-surfactants, and organic compounds. In the bio-polymer group, xantham gum and dextran were selected for study. The study of bio-surfactants concentrated on biological detergents. The organic compounds included high carbon alcohols and perfluorocarbon compounds. For each of these studies, four reactors of acclimated ERIH2 were used. The mass transfer enhancing agent was added to two of the batch reactors. All the batch reactors were regassed frequently with coal synthesis gas and gas compositions were closely monitored. FIGS. 54 to 64 show the CO consumption in these batch studies and FIGS. 65–75 show the plots of $(-dCo/dt)(1/V_L)$ vs $P^G_{CO}$. The values of $K_L a/H$ were calculated based on the above procedures. Table 17 summarizes the results of the various chemicals studied.

As is shown in Table 16, only some of the bio-surfactants, especially the non-ionic biological detergents, show significant improvement in mass transfer rate. Most impressive was the addition of 0.1 volume percent TYLOXAPOL ™ detergent which increased the CO mass transfer rate over 300 percent. Foaming during these studies indicates that the effect of the addition of biological detergents was reduction of the surface tension, rather than an increase in CO solubility. In general, bio-polymers significantly improved the performance of the culture by reducing the mass transfer resistance.

TYLOXAPOL ™ detergent was chosen for study in the CSTR. In these experiments, the gas retention time was controlled at 20 minutes. A dry cell density of at 0.4 g/L was used with a 1/2 horsepower agitator. The CO conversion was measured at steady state as the agitation was varied from 100 to 1000 rpm. At an agitation rate of 100 rpm, 0.01 or 0.015 volume percent TYLOXAPOL ™ detergent was added to the culture and the gas compositions were frequently monitored until equilibrium had been reached. The agitation rate was then increased in 100 rpm increments until no further improvement was observed.

Figure 76:
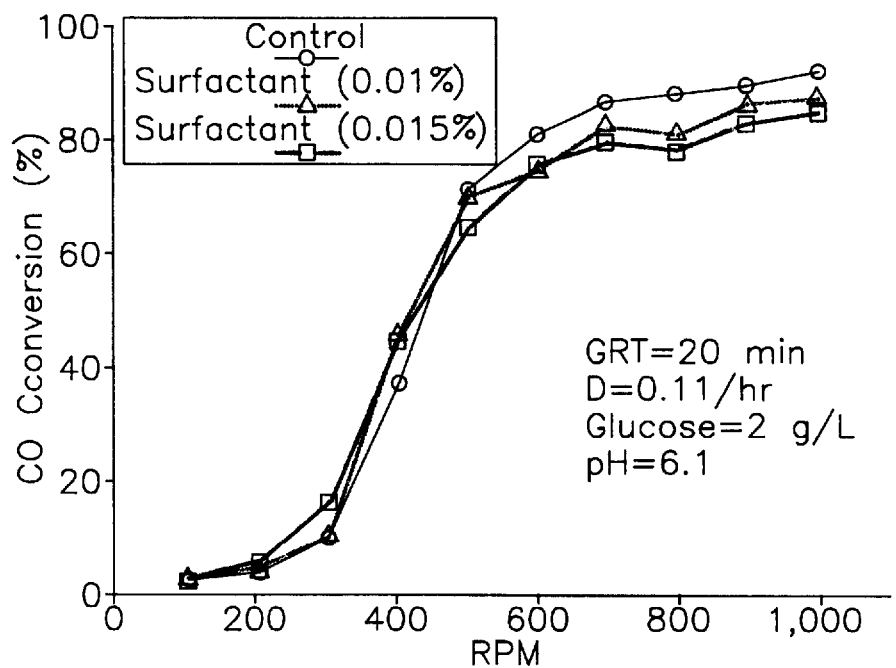
Figure 77:
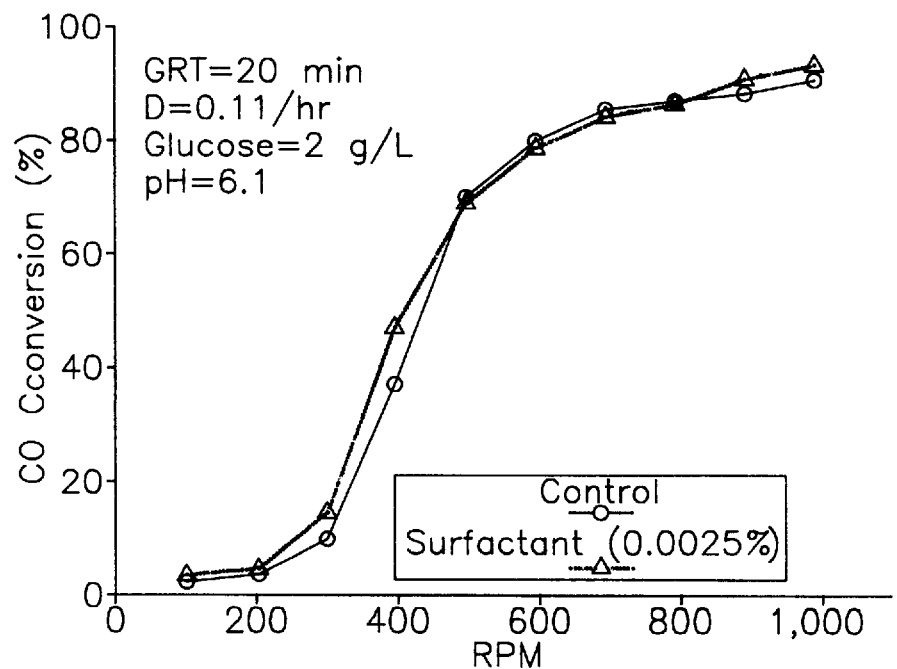

FIG. 76 shows the effect of TYLOXAPOL ™ detergent on CO conversion as a function of agitation rate. TYLOXAPOL ™ detergent had a minimal positive effect on conversion at agitation rates up to 400 rpm. TYLOXAPOL ™ detergent addition decreased CO conversion at higher agitation rates. FIG. 77 shows the effect of EMCOL CNP-110™ detergent on CO conversion by ERIH2. Again, the same trends as were shown in FIGS. 76 were observed. It appears that surfactant addition in the low concentrations needed to prevent toxicity are not sufficient to significantly promote mass transfer.

$K_L a/H$ for the CSTR system can also be estimated from Equation (4), which describes the CO material balance in a closed system. With the assumption of completely mixed flow mass transfer limitation, $P^L_{CO}$ becomes zero, and this equation can be modified to describe the CSTR system:

$$\frac{1}{V_L} \cdot \frac{dN_{CO}}{dt} = \frac{K_L a}{H} P^O_{CO} \qquad (5)$$

In this equation, $dN^G_{CO}/dt$ is the steady state CO consumption, $P^O_{CO}$ is the steady state outlet gas CO partial pressure, and $K_L a/H$ will be a function of agitation rate. The steady state CO consumption can further be related to the inlet CO partial pressure and conversion through the ideal gas law by the following equation:

$$\frac{dN^G_{CO}}{dt} = \frac{P^I_{CO} V^I_G}{RT} X \qquad (6)$$

where $P^I_{CO}$ is the inlet CO partial pressure, $V^I_G$ is the inlet gas flow rate, R is the ideal gas constant, T is absolute temperature, and X is the CO conversion.

Since for every mole of CO consumed, two moles of gas are produced (1 mole $H_2$ and 1 mole $CO_2$) the determination of the outlet CO partial pressure is complicated if the reaction is maintained at the same total pressure as the inlet gas. The flow rate of the outlet gas stream, $V^O_G$ will be larger than the inlet flow rate as shown by the following equation:

$$V^O_G = V^I_G + V^I_G \cdot \frac{P^I_{CO}}{P_T} \cdot X = V^I_G \left(1 + \frac{P^I_{CO}}{P_T} \cdot X\right) \qquad (7)$$

By the definition of conversion, $P^O_{CO}$ can be estimated by the following equations under constant temperature:

$$\frac{P^I_{CO} V^I_G - P^O_{CO} V^O_G}{P^I_{CO} V^I_G} = X \qquad (8)$$

$$P^O_{CO} = (1-X) P^I_{CO} \frac{V^I_G}{V^O_G} = (1-X) P^I_{CO} / \left(1 + \frac{P^I_{CO}}{P_T} \cdot X\right) \qquad (9)$$

Equation (4) can then be rearranged into:

$$\frac{1}{V_L} \cdot \frac{P^I_{CO} V^I_G}{RT} \cdot X = \frac{K_L a}{H} \cdot \frac{(1-X) P^I_{CO}}{(1 + P^I_{CO} X/P_T)} \qquad (10)$$

By defining $Y^I_{CO} = P^I_{CO}/P_T$, Equation (10) can be rearranged as follows and $K_L a$ can be calculated with Co conversion, X, as the major variable.

$$\frac{K_L a}{H} = \frac{V^I_G X}{RT V_L} \cdot \frac{(1 + Y^I_{CO} X)}{(1-X)} \qquad (11)$$

This equation can be further simplified by utilizing the definition of gas retention time, $\theta = V_L/V^I_G$.

$$\frac{K_L a}{H} = \frac{1}{RT\theta} \cdot \frac{X(1 + Y^I_{CO} X)}{(1-X)} \qquad (12)$$

For a given synthesis gas composition, $Y^I_{CO}$ will be constant; for this gas mixture (CO:65%, $H_2$: 20%, $CH_4$: 4%, $CO_2$: 11%), the value is 0.64. If the operating temperature and gas retention time are maintained constant, $K_La/H$ will only be a function of conversion, which is affected by the agitation rate. This equation is valid when the gas flow pattern inside the reactor is completely mixed flow; and the reaction is under mass transfer limitation. The gas flow pattern inside the reactor will change gradually from plug flow into completely mixed flow as the agitation rate is increased from zero. Thus, this equation should be appropriate under high cell concentrations and high agitation rates.

A summary of the mass transfer coefficients and CO consumption by ERIH2 in the presence of various co-solvents and surfactants in batch culture is listed in Tables 17 and 18. As is noted in Table 17, several co-solvents/surfactants brought about an increase in the mass transfer coefficient, $K_La$. The addition of 0.1 percent TRITON N-101™ detergent brought about an 84 percent increase in $K_La$ compared to the control. More significant were the additions of 0.1 percent NONIDET P-40™ detergent (107 percent increase), 0.1 percent Triton X-100 (203 percent increase) and 0.1 percent TYLOXAPOL™ detergent (340 percent increase). A comparison of CO consumption with and without some of the surfactants in Table 17 is presented in Table 18. Of the surfactants listed, BRIJ 96™ detergent and TYLOXAPOL™ detergent brought about increases in the Co consumption over the control. Longevity in increased CO consumption was seen only with TYLOXAPOL™ detergent, which showed an increase in CO consumption over the control even after two regassings. TYLOXAPOL™ detergent is thus the surfactant of choice for the ERIH2 system based upon increases in $K_La$ and CO conversion, and the longevity of the CO increase.

The intrinsic kinetics for gas fermentations can be described by a modified Monod model that includes substrate inhibition:

$$\mu = \frac{\mu_m P^L_{CO}}{K_S + P^L_{CO} + (P^L_{CO})^2/W} \tag{13}$$

In the above equation, q is the specific substrate uptake rate, $P^L_{CO}$ is the liquid phase substrate concentration, $q_m$ is the maximum achievable substrate uptake rate, $K_s$ is the monod saturation constant, and W is the substrate inhibition parameter. This equation can further be rearranged as:

$$\frac{P^L_{CO}}{q} = \frac{K_S}{q_m} + \frac{P^L_{CO}}{q_m} + \frac{P_{CO}{}^2_L}{q_M W} \tag{14}$$

The difficulty in using the above equations for determining the intrinsic kinetic parameters is the determination of the dissolved CO concentration, $P^L_{CO}$. The measurement of small concentrations of CO in the liquid would be very inaccurate and sensors are not available to determine the slightly soluble CO concentration. Therefore, an indirect estimation method is used.

A CO material balance equation in batch fermentation defines the rate of disappearance of CO from the gas phase, $dN^G_{CO}/V_L dt$, as proportional to the mass transfer driving force, the difference between CO partial pressure in the gas phase ($P^G_{CO}$) and liquid phase ($P^L_{CO}$), with the proportionality constant the mass transfer coefficient, $K_La/H$:

$$-\frac{1}{V_L} \frac{dN^G_{CO}}{dt} = \frac{K_L a}{H} (P^G_{CO} - P^L_{CO}) \tag{15}$$

The two unknowns in this equation are the dissolved CO concentration, $P^L_{CO}$ and the mass transfer coefficient, $K_La/H$. Thus, if the value of the mass transfer coefficient is known, the liquid phase CO concentration can be estimated from this equation. The mass transfer coefficient can be obtained from the above equation when the batch fermentation is mass transfer limited. In batch fermentations, the cell concentration increases as the gas is consumed. However, the supply of the gas becomes limited as the cell concentration continues to increase. $P^L_{CO}$ becomes zero under mass transfer limitation, and from Equation (15), the plot of the gas phase CO disappearance rate ($1/V_L$-$dN^G_{CO}/dt$) vs $P^G_{CO}$ is a linear relationship through the origin, with a scope of $K_La/H$.

Once the volumetric mass transfer coefficient is known, the material balance equation can be used to estimate the dissolved CO concentration in the region where $P^L_{CO}$ is not zero. These values can then be used to determine the values of kinetic parameters by curve fitting the data to Equation (14).

The procedure to determine intrinsic kinetic parameters is to conduct a series of batch fermentations with different CO partial pressure. From these data, mass transfer coefficients for each run can be estimated by finding the slope of the linear range of ($1/V_L$-$dN^G_{CO}/dt$) vs $P^G_{CO}$. Then the $P^L_{CO}$ value can be estimated by Equation (15). The intrinsic kinetic parameters, $q_m$, $K_s$, and W can then be estimated by curve fitting of $P^L_{CO}/q$ vs $P^L_{CO}$.

Figure 78:
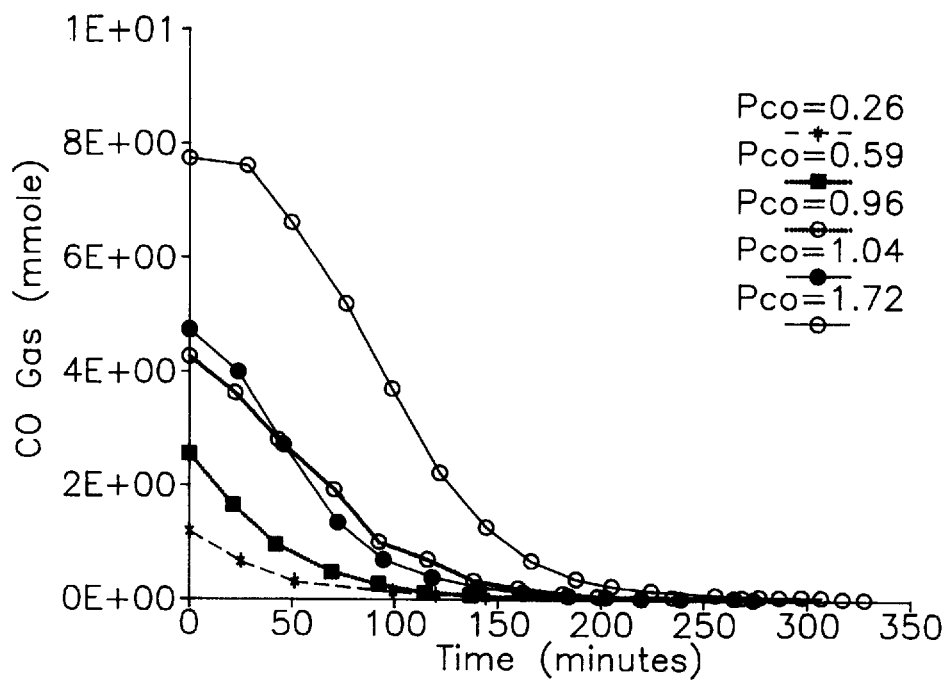

FIG. 78 shows gas phase partial pressure ($P^L_{CO}$) profiles for ERIH2 in batch culture. Initial CO partial pressures ranging from 0.25–1.72 atm were used in the study. As is noted, the times for complete CO utilization increased with increasing initial CO partial pressure, ranging from 125 hr at 0.25 atm to 240 hr at 1.72 atm.

Figure 79:
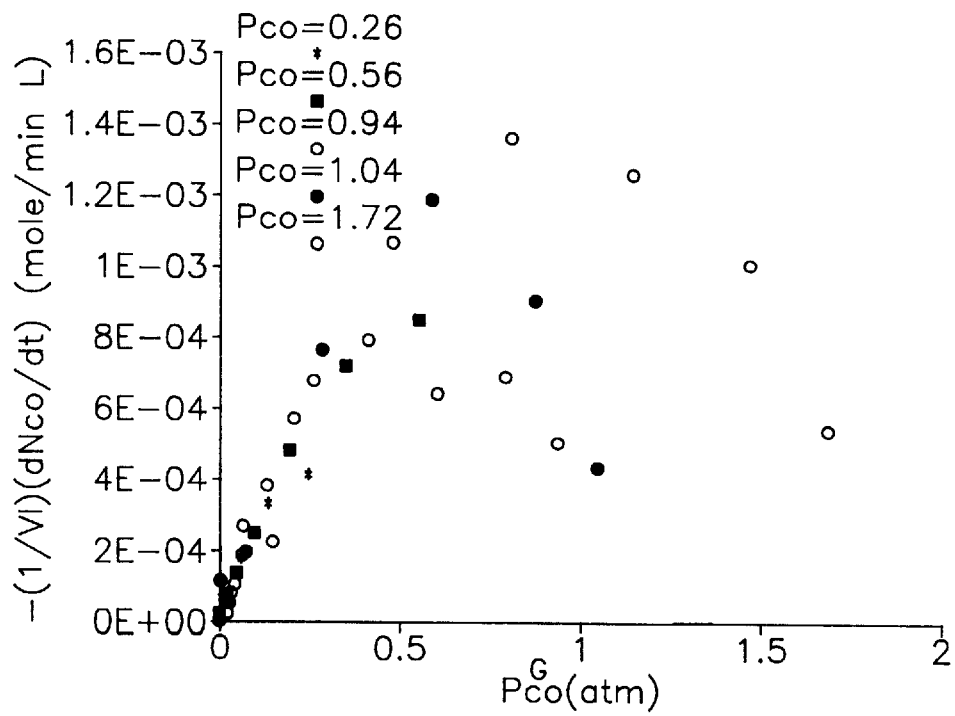

The determination of the mass transfer coefficient, $K_La/H$, for the batch bottle experiments by Equation (15) is illustrated in FIG. 79. As is noted, a single straight line is obtained for the mass transfer limited region of the fermentation, the $P^L_{CO}$ region from 0–0.3 atm. $K_La/H$ has a value of 0.0025mmol/min·mL·atm, as determined from the slope of the straight line. This compares well with previous batch experiments performed in these batch bottles at the same agitation rate.

Figure 80:
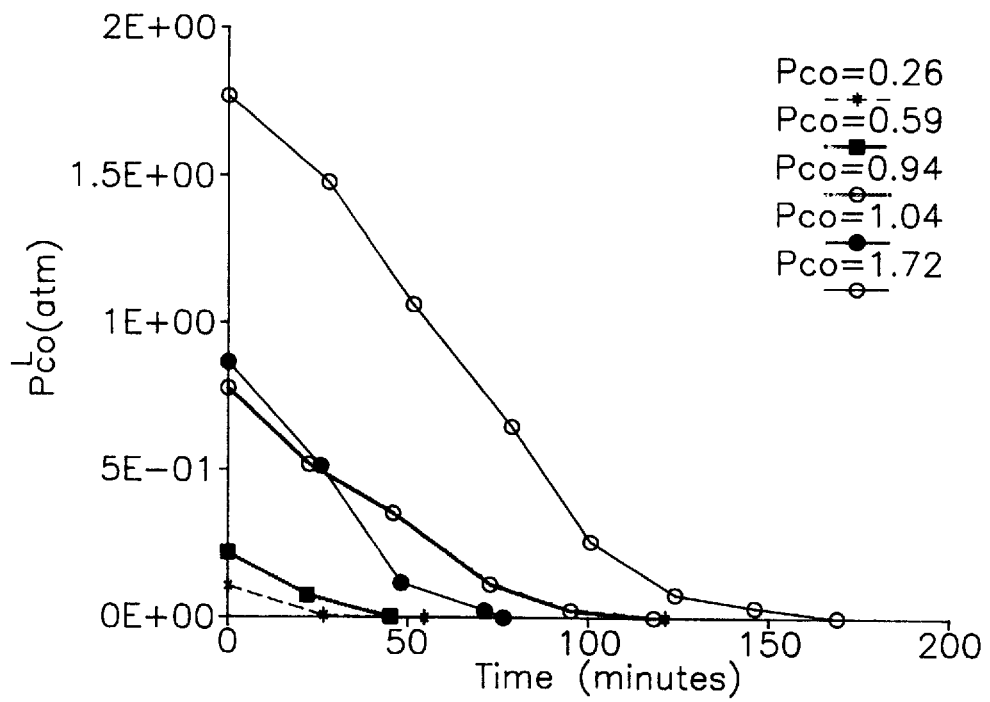

A plot of the liquid phase CO tensions, $P^L_{CO}$ determined using Equation (15) as a function of time is shown in FIG. 80. The liquid phase tensions range from 0 to 1.75 atm. Finally, a plot of $P^L_{CO}/q$ as a function of $P^L_{CO}$ is shown in FIG. 80. This plot is a rearrangement of Equation (13) as in Equation (14).

Thus, a plot of $P^L_{CO}/q$ as a function of PLCo should yield a quadratic equation of intercept $K_s/q_m$, slope $1/q_m$ and curvature $1/q_m W$.

Figure 81:
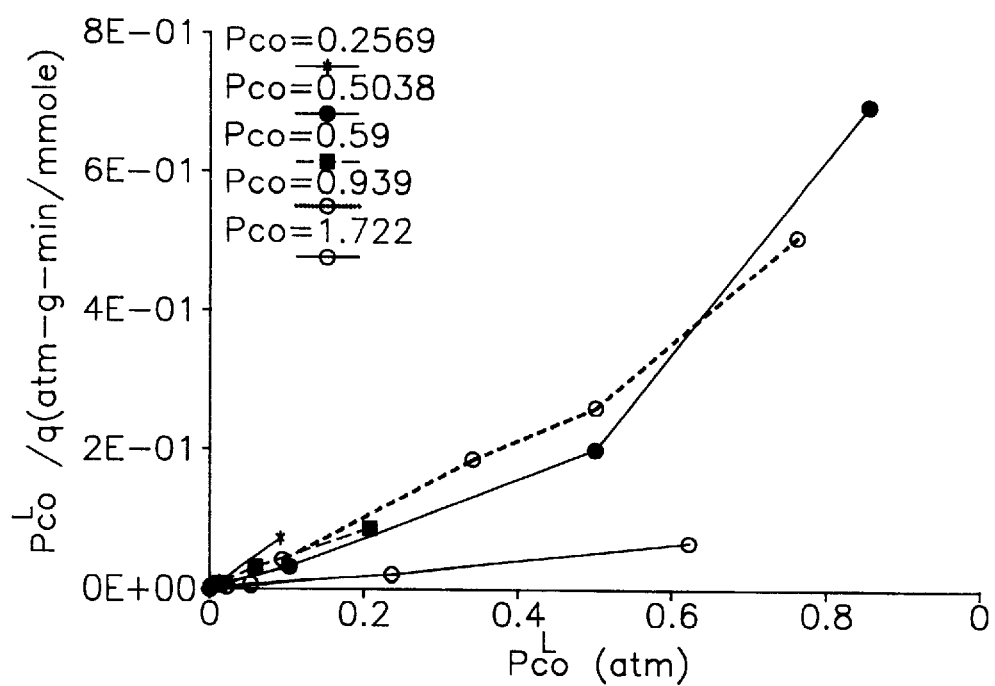

From FIG. 81, the following equation for the specific uptake rate of ERIH2 as a function of $P^L_{CO}$ is obtained:

$$q = \frac{1427 P^L_{CO}}{0.486 + P^L_{CO} + (P^L_{CO})^2/0.0497}, \text{mmol/hr} \cdot \text{gcells} \tag{16}$$

A similar expression was obtained for *R. rubrum*:

$$q = \frac{49.2 P^L_{CO}}{0.384 + P^L_{CO} + (P^L_{CO})^2/0.126}, \text{mmol/hr} \cdot \text{gcells} \tag{17}$$

These equations may be used to compare the performance of these two cultures.

A comparison of calculated specific CO uptake rates for the two bacteria is shown in Table 19. As is shown, the specific uptake rate for ERIH2 is 1200–2000% higher than the specific uptake rate of *R. rubrum*. This means that, for a given cell concentration, ERIH2 will utilize CO up to 20 times faster than *R. rubrum*, and without the need for light.

In a production scale operation the intermediate product will be primarily carbonic acid, $H_2CO_3$. Hydrogen removal from $H_2CO_3$ is the product recovery step for this example. There are a number of processes to remove $CO_2$ from gas streams. The separation is based on one of the following four principles (Eickmeyer et al., 1978):

(1) $CO_2$ is weakly acidic, forming $H_2CO_3$ when dissolved in water. This permits the use of liquid alkaline solutions, either regenerable or nonregenerable, for absorption of $CO_2$.

(2) $CO_2$ is soluble in water and in many organic liquids. Processes based on solubility as opposed to chemical affinity are also used.

(3) The molecular size and structure of $CO_2$ permit it to be selectively adsorbed on solid adsorbants, particularly molecular sieves.

(4) The acidic nature or size and structures of $CO_2$ in some mixtures permit it to be separated by the use of permeable membranes.

The amount of $CO_2$ removed by solid adsorbents is small compared to that removed by liquid absorbent systems. Permeable membrane separation is of minor commercial importance (Eickmeyer et al., 1978). Hence, commercial processes are limited to either alkaline solution absorption and physical solvents (solubility) absorption.

Figure 82:
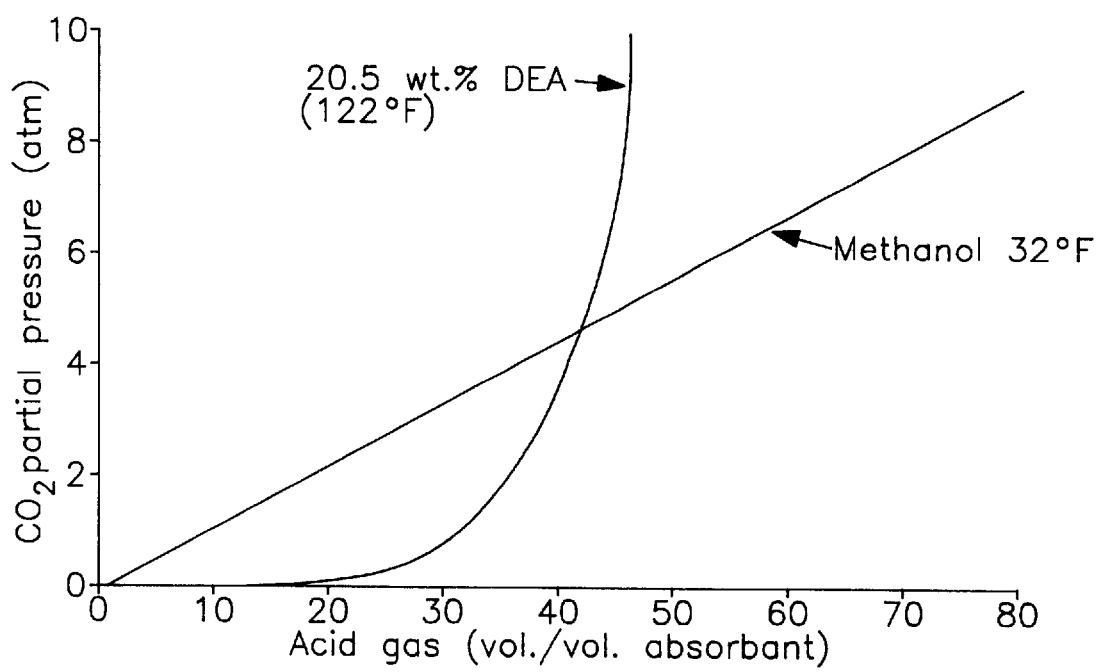

There are certain characteristic differences between processes based on physical solubility and those based on chemical reaction with an alkaline solution. FIG. 82 shows equilibrium lines for a typical chemical reaction system (20.5 wt % DEA) and for a typical methanol solvent system (Eickmeyer et al., 1978). For the solvent system, the $CO_2$ content of the liquid phase increases in direct proportion to the partial pressure of $CO_2$ in the vapor phase. For the chemical reaction system, the equilibrium pressure increases only slightly with loading of the liquid over the lower range of solution loadings, but curves upward sharply as the loading approaches the stoichiometric limit set by the chemical reaction. It is obvious that at high available partial pressures of $CO_2$ as in this application, the solvent system is capable of attaining a higher loading of the scrubbing solution and, therefore, will require lower solution circulation rates for the same degree of $CO_2$ removal.

Another important advantage of the solvent system is at regeneration. The ratio of stripping vapor/solution required to strip the solution to a very low residual $CO_2$ content will be substantially less for the solvent system than for the chemical system. Thus, a stripped solvent system will generally be capable of scrubbing the gas to be treated to a lower level of residual $CO_2$. Compared to a chemical system, the total energy required for the solvent system per mole of $CO_2$ removed is generally lower and is composed of power for circulating the solution and, in many cases, for refrigeration since the solubility of $CO_2$ is greatly increased by operating at less than ambient temperature.

Table 20 lists the typical operating conditions of various $CO_2$ removal processes (Eickmeyer et al., 1978). As discussed above, solvent systems involving sulfinol, selexol, rectisol, purisol, and fluor appear to be most suitable. The feed gas in this application will contain about 45% $CO_2$ and a total pressure of 400 psi, or 180 psi $CO_2$ partial pressure. The majority of these solvents can also simultaneously remove $H_2S$, and some solvents such as sulfinol and selexol even remove COS. The processes using these solvents have the advantages of a low solvent circulation rate, low plant costs, low utilities costs, high effectiveness for the removal of COS, $CS_2$ and HS, low solvent degradation and low corrosion rates (Eickmeyer et al., 1978). The use of these processes entails payment of a royalty.

In light of the foregoing the following conclusions are offered:

1. *Rhodospirillum rubrum*, strain ATCC 25903, has been identified as the best photosynthetic bacterium to perform the water gas shift, showing a maximum specific CO uptake rate of 16.0 mmol/g·hr.

2. A new bacterium, ERIH2, ATCC 55404 isolated from natural sources, rapidly catalyzes the water gas shift reaction with stoichiometric $H_2$ yields and without requiring light for growth. The maximum specific CO uptake rate of ERIH2 is 200mmol/g.hr. Small amounts of relatively inexpensive carbon sources such as glucose may be utilized as growth substrates.

3. Monod-type kinetic expressions for specific substrate uptake rate by *R. rubrum* and ERIH2 have been obtained.

4. Continuous culture operation with ERIH2 has been demonstrated in stirred tank and trickle bed bioreactors. As an example, a CO conversion of 85 percent and $H_2$ yield of 100percent have been demonstrated in the CSTR with a gas retention time of 20 minutes and a 900 rpm agitation rate.

5. Chemicals have been added to the medium which have brought about a 340 percent improvement in the rate of mass transfer of CO into the liquid phase in batch culture while not negatively affecting the performance of the culture.

In accordance with another example of the present invention, municipal solid waste (MSW) is converted to hydrogen by gasifying a municipal solid waste using air as the oxident to produce a raw synthesis gas having a composition (percent by volume) of about 16% CO, 8% $CO_2$, 12% $H_2$, and about 60% $N_2$ cooling the raw synthesis gas to about 30° C., adding the cooled synthesis gas to a bioreactor with an aqueous nutrient media and a microorganism ERIH2, converting at least the CO to $H_2$, venting the gases from the bioreactor, separating the hydrogen from the other gases so as to recover hydrogen product.

In accordance with another example of the present invention, municipal solid waste is converted to hydrogen by gasifying the municipal solid waste using an oxygen oxident to produce a raw synthesis gas having percent by volume composition of about 49% CO, about 15% $CO_2$, and about 30% $H_2$ cooling the raw synthesis gas to about 30° C., adding the cooled synthesis gas to a bioreactor with an aqueous nutrient media and the microorganism ERIH2, allowing the microorganism ERIH2 to convert at least the carbon monoxide to $H_2$, venting the gases from the bioreactor, and separating the hydrogen from the other gases so as to recover a hydrogen product.

In accordance with another example of the present invention, sewage sludge is converted to hydrogen by gasifying the sewage sludge to produce a raw synthesis gas having a volume percent composition of about 37% CO, 27% $CO_2$, and 35% $H_2$, cooling the synthesis gas to about 30° C., adding the cooled synthesis gas to a bioreactor with an aqueous nutrient media and the microorganism ERIH2, allowing the microorganism to convert at least the carbon monoxide to hydrogen, venting the gases from the bioreactor, separating the hydrogen from the other gases so as to recover a hydrogen product.

In accordance with another example of the present invention, municipal solid waste (MSW) is converted to hydrogen by gasifying a municipal solid waste using air as the oxident to produce a raw synthesis gas having a composition (percent by volume) of about 16% CO, 8% $CO_2$, 12% $H_2$, and about 60% $N_2$, cooling the raw synthesis gas to about 30° C., adding the cooled synthesis gas to a bioreactor with an aqueous nutrient media and a microorganism *R. rubrum*, converting at least the CO to $H_2$ venting the gases from the bioreactor, separating the hydrogen from the other gases so as to recover hydrogen product.

In accordance with another example of the present invention, municipal solid waste is converted to hydrogen by gasifying the municipal solid waste using an oxygen oxident to produce a raw synthesis gas having percent by volume composition of about 49% CO, about 15% $CO_2$, and about 30% $H_2$ cooling the raw synthesis gas to about 30° C., adding the cooled synthesis gas to a bioreactor with an aqueous nutrient media and the microorganism *R. rubrum*, allowing the microorganism *R. rubrum* to convert at least the carbon monoxide to $H_2$, venting the gases from the bioreactor, and separating the hydrogen from the other gases so as to recover a hydrogen product.

In accordance with another example of the present invention, sewage sludge is converted to hydrogen by gasifying the sewage sludge to produce a raw synthesis gas having a volume percent composition of about 37% CO, 27% $CO_2$, and 35% $H_2$, cooling the synthesis gas to about 30° C., adding the cooled synthesis gas to a bioreactor with an aqueous nutrient media and the microorganism *R. rubrum*, allowing the microorganism to convert at least the carbon monoxide to hydrogen, venting the gases from the bioreactor, separating the hydrogen from the other gases so as to recover a hydrogen product.

In accordance with yet another example of the present invention, raw synthesis gas is converted to hydrogen using the microorganism ERIH2 by cooling a synthesis gas to about 50° C. or less adding the cooled synthesis gas to a bioreactor along with an aqueous nutrient media and the microorganism ERIH2, allowing the microorganism to convert at least a substantial portion of the carbon monoxide to hydrogen, and recovering the hydrogen from the bioreactor.

In accordance with yet another example of the present invention, raw synthesis gas is converted to hydrogen by a microorganism *R. rubrum* by cooling the synthesis gas to about *50°* C. or less, adding the cooled synthesis gas to a bioreactor along with an aqueous nutrient media and the microorganism *R. rubrum*, allowing the microorganism to convert most of the carbon monoxide to hydrogen, and recovering the hydrogen from the bioreactor.

In accordance with still yet another example of the present invention, synthesis gas having a volume percent composition of about 10 to 50% CO, 5 to 40% $CO_2$ and 10 to 35% $H_2$ is supplied to a bioreactor as a gaseous substrate along with an aqueous nutrient media and an anaerobic bacteria capable of converting carbon monoxide to hydrogen, allowing the microorganism to convert most of the carbon monoxide to hydrogen, and recovering the hydrogen from the bioreactor.

In accordance with another embodiment of another example of the present invention, waste biomass is converted to hydrogen by gasifying the waste biomass to produce a synthesis gas having at least 10 to 50% by volume carbon monoxide, converting the carbon monoxide in the synthesis gas to hydrogen by a microorganism selected from at least one of ERIH2 or *R. rubrum* and a bioreactor along with an aqueous nutrient media, and recovering the hydrogen produced.

In accordance with another example of the present invention, hydrogen is separated from the other gases vented from a bioreactor by a sulfinol process.

In accordance with yet another example of the present invention, at least one of the microorganisms ERIH2 and/or *R. rubrum* is used to convert the carbon monoxide from a synthesis gas produced by gasification of waste biomass into hydrogen.

In accordance with yet still another example of the present invention, biomass waste selected from at least one of municipal solid waste, sewage sludge, plastic, tires, coal, and mixtures thereof is converted into a useful product hydrogen by gasifying the biomass waste to produce a synthesis gas containing carbon monoxide, converting the carbon monoxide to hydrogen using a microorganism selected from one of *R. rubrum* and ERIH2.

Thus, it will be appreciated that, as a result of the present invention, a highly effective, improved biological process for converting waste biomass to useful products, process for converting synthesis gas to hydrogen, and microorganism is provided by which the principal objective, among others, is completely fulfilled. It is contemplated, and will be apparent to those skilled in the art from the preceding description and accompanying drawings, that modifications and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

REFERENCES

Anderson, L. and R. C. Fuller. "Photosynthesis in *Rhodospirillum rubrum* I. Autotrophic Carbon Dioxide Fixation," *Plant Physiol* 42, p. 487 (1967).

Balch, N. E. and R. S. Wolfe. *Appl. Environ. MIcrobiol.*, 32, 781–791 (1976).

Barik, S., R. E. Corder, E. C. Clausen, and J. L. Gaddy. *Energy Progress*, 7, p. 157 (1987).

Bhatnagar, L., J. A. Krzycki, and J. G. Zeikas. "Analysis of Hydrogen Metabolism in *Methanosarcina barkeri*: Regulation of Hydrogenase and Role of C-dehydrogenase in $H_2$ Production," *FEMS Microbiology Letter*, 41, pp. 337–343 (1987).

Bott, M., and R. K. Thauer. "Proton Translocation Coupled to the Oxidation of Carbon Monoxide to $CO_2$ and $H_2$ in *Methanosarcina barkeri*," *Eur. J. Biochem.* 179, pp. 469–472 (1989).

Bryant, M. P. "Commentary on the Hungate Technique for Culture of Anaerobic Bacteria," *Amer. J. Clin. Nutr.* 25, pp. 1324–1328(1972).

Daniels, L. G., G. Fulton, R. W. Spencer, W. H. Orme-Johnson. "Origin of Hydrogen in Methane Produced by *M. thermoautotrophicum, J. Bacteriol.* 14, pp. 694–698 (1980).

Dashekvicz, M. P. and R. L. Uffen. "Identification of a Carbon Monoxide-Metabolizing Bacterium as a Strain of *Rhodopseudomonas gelatinosa* (Molisch) van Niel," *Int'l J. of Syst. Bacteriol,* 29, pp. 145–148 (1978).

Diekert, G. and M. Ritter. "Carbon Monoxide Fixation into the Carboxyl Group of Acetate During Growth of *Acetobacterium woodii*on $H_2$ and $CO_2$," *FEMS Microbiol. Letters,* 17, pp. 299–302 (1983).

Eickmeyer, A. G., R. R. Johnson, and B. G. Goar. "Carbon Dioxide Removal", Encyclopedia of Chemical Processing and Design. J. J. McKeHa Ed., V.6. 1978. pp.292–310.

Fuller, R. C. "Photosynthetic Carbon Metabolism in the Green and Purple Bacteria, "*The Photosynthetic Bacteria*, ed. by R. K. Clayton and W. R. Sistrom, Plenum Press, New York, pp. 691–705(1978).

Gest, H., M. D. Kamen and H. M. Bregoff. *J. Biolog. Chem.*, 182, p. 153 (1950).

Goar, G., "Sulfinol process has several key advantages", *Oil & Gas J.* Jun. 30, 1969. pp. 117–120.

Hansen, T. A. "Electron Donor Metabolism in Phototrophic Bacteria," in J. G. Ormerod (ed.) *The Phototrophic Bacteria: Anaerobic Life in the Light*, University of California Press, Berkeley and Los Angeles pp. 76–99 (1983).

Hegemann, G. "Oxidation of Carbon Monoxide by Bacteria," *Trends in Biochemical Sciences,* 5, pp. 256–259 (1980).

Hessley, R. K., J. W. Reasoner, and J. T. Riley. *Coal Science*, Wiley, N.Y. (1986).

Hirsch, P. "Photosynthetic Bacterium Growing Under Carbon Monoxide," *Nature,* 217, pp. 555–556 (1968).

Hungate, R. E. "A Roll Tube Method of Cultivation of Strict Anaerobes," in *Methods in Microbiology*, Vol. 5b, Academic Press, New York (1969).

Keppen, O. I., A. N. Nozhevnikova, and V. M. Gorlenko. *Microbiology*, 45, pp. 10–13 (1976).

Ko, C. W., J. L. Vega, S. Barik, E. C. Clausen, and J. L. Gaddy. "Biological Production of Methane from Coal Synthesis Gas Under High Pressure," presented at the AIChE Summer National Meeting, Minneapolis, Minn. (1987).

Lorowitz, W. H. and M. P. Bryant. "Peptostreptococcus productus Strain that Grows Rapidly with Carbon Monoxide as the Energy Source," *Appl. Environ. Microbiol.*, 47, p. 961–964 (1984).

Martin, D. R., L. L. Lundie, R. Kellum, and H. L. Drake. "Carbon Monoxide-Dependent Evolution of Hydrogen by the Homoacetate-Fermenting Bacterium *Clostridium thermoaceticum*," *Curr. Microbiol*, 8, pp. 337–340 (1983).

Meyer, O. and H. G. Schlegal. "Biology of Aerobic Carbon Monoxide-Oxidizing Bacteria," *Annual Reviews of Microbiology*, 37, pp. 277–310 (1983).

O'Brien, J. M., R. H. Wolkin, T. T. Moench, J. B. Morgan, and J. G. Zeikus. "Association of Hydrogen Metabolism with Unitrophic or Mixotrophic Growth of *Methanosarcina barkeri* on Carbon Monoxide," *J. Bacteriol.* 158, pp. 373–375 (1984).

Payne, K. R. *Chemicals from Coal*, Wiley, N.Y. (1987).

Quayle, J. R. and N. Pfenning. "Utilization of Methanol by Rhodospirillaceae," *Arch. Microbiol.*, 102, pp. 193–198 (1975).

Spratt, H. G. and J. S. Hubbard. "Carbon Monoxide Metabolism in Roadside Soils," *Appl. and Environ. Microbiol.*, 41, pp. 1192–1201(1981).

Stupperich, E., K. E. Hammel, G. Fuchs, and R. K. Thauer. "Carbon Monoxide Fixation into the Carboxyl Group of Acetyl Coenzyme A During Autotrophic Growth of Methanobacterium," *FEBS Lett.*, 152, pp. 21–23 (1983).

Tracy, C. A., and E. Ashare. "Biomethanation of Biomass Pyrolysis Gases," Dynatech R/D Company Final Report on SERI Contract No. XB-9-8356-1, Cambridge, Minn. (1981).

Uffen, R. L. "Anaerobic Growth of a Rhodopseudomonas Species in the Dark with Carbon Monoxide as Sole Carbon and Energy Substrate," *Proc. Nat'l. Acad. Sci.*, 73, pp. 3298–3302 (1976).

Uffen, R. L. "Metabolism of Carbon Monoxide," *Enzyme and Microbiol. Technol.*, 3, pp. 197–206 (1981).

Uffen, R. L., C. Sybesma, and R. S. Wolfe. "Mutants of *Rhodospirillum rubrum* Obtained After Long-Term Anaerobic Dark Growth," *J. Bacterio.* 108, pp. 1348–1356 (1971).

Vega, J. L., G. M. Antorrena, E. C. Clausen, and J. L. Gaddy. "Biological Production of Liquid and Gaseous Fuels from Coal Synthesis Gas," *ACS Symposium Series*, (1988a).

Vega, J. L., G. M. Antorrena, E. C. Clausen, and J. L. Gaddy. "Study of Gaseous Substrate Fermentations: Carbon Monoxide Conversion to Acetate, 2. Continuous Cultures," *Biotechnol. and Bioeng.*, (1989b).

Vega, J. L., V. L. Holmberg, E. C. Clausen, and J. L. Gaddy. "Fermentation Parameters of Peptostreptococcus productus on Gaseous Substrates (CO, $H_2/CO_2$)," *Archives in Microbiology*, (1988b).

Vega, J. L., K. T. Klasson, D. E. Kimmel, C. W. Ko, E. C. Clausen, J. L. Gaddy, "Sulfur Toxicity," Topical Report DOE Contract DE-AC-21-86MC23281, METC (1989).

Wender, I. "Catalysts in Conversion of Synthesis Gas," in *Chemicals from Coal*, K. R. Payne (ed.) Wiley, N.Y. (1987).

TABLE 1

Municipal Solid Waste (MSW) Gasification - Syngas Composition (% by vol)

| Gasification Medium (Plant) | Vigel et al air (pilot) | Black et al air (pilot) | Groeneveld Purox oxygen (commercial) | Groeneveld Bailie oxygen and steam (pilot) | Groeneveld Purox oxygen (pilot) |
|---|---|---|---|---|---|
| CO | 16.5 | 11.6 | 49.0 | 20.0 | 40.0 |
| $CO_2$ | 8.5 | 15.4 | 15.0 | 39.0 | 24.0 |
| $H_2$ | 12.5 | 12.5 | 30.0 | 30.0 | 24.0 |
| $O_2$ | 2.4 | 0.8 | | | |
| $N_2$, Ar | 60.1 | 45.1 | 1.0 | | 1.0 |
| $CH_4$ | | 2.5 | 3.0 | 5.0 | 5.6 |
| $C_2^+$ | | 3.2 | 2.0 | 6.0 | |
| $H_2S$, COS | | | | | 5.4 |
| for CO, $CO_2$, $H_2$ only basis | | | | | |
| CO | 44.0 | 29.4 | 52.1 | 22.5 | 45.4 |
| $CO_2$ | 22.7 | 39.0 | 16.0 | 43.8 | 27.3 |
| $H_2$ | 33.3 | 31.6 | 31.9 | 33.7 | 27.3 |

TABLE 2

Syngas Produced by the Gasification of Sewage Sludge

| | Vol % | | | |
|---|---|---|---|---|
| Component | Davis et al., 1990 | Texaco Zimpro A, 1989 | Texaco Carver-Greenfield B, 1989 | Texaco Carver-Greenfield C, 1989 |
| CO | 37.0 | 37.09 | 36.40 | 34.96 |
| $CO_2$ | 27.0 | 25.30 | 25.31 | 27.63 |
| $H_2$ | 35.0 | 35.26 | 35.74 | 35.49 |
| $N_2$ + Ar | 0.6 | 1.68 | 1.84 | 1.10 |
| $H_2S$, $CS_2$, COS | 0.3 | 0.65 | 0.71 | 0.80 |
| $CH_4$ | 0.1 | 0.02 | 0 | 0.02 |

TABLE 3

Characteristics of Generic Types of Gasification Reactors

| | MOVING-BED | | FLUIDIZED-BED | | ENTRAINED-FLOW |
|---|---|---|---|---|---|
| Ash Conditions | Dry Ash | Slagging | Dry Ash | Agglomerating | Slagging |
| Feed Characteristics Size | Coarse (0–2 inch) | Coarse (0–2 inch) | Crushed (0–¼ inch) | Crushed (0–¼ inch) | Pulverized (0–100 mesh) |
| Acceptability of Fines | Limited | Better than dry ash | Good | Better | Unlimited |
| Acceptability of Caking Coal | Yes (with/ modifications) | Yes (with/ modifications) | Possibly | Yes | Yes |
| Preferred Coal Rank Operating | Low | High | Low | Any | Any |

TABLE 3-continued

Characteristics of Generic Types of Gasification Reactors

| Ash Conditions | MOVING-BED | | FLUIDIZED-BED | | ENTRAINED-FLOW |
|---|---|---|---|---|---|
| | Dry Ash | Slagging | Dry Ash | Agglomerating | Slagging |
| Characteristics | | | | | |
| Exit Gas Temperature | Low (800° F.–1200° F.) | Low (800° F.–1200° F.) | Moderate (1700° F.–1900° F.) | Moderate (1700° F.–1900° F.) | High (>2300° F.) |
| Oxidant Requirement | Low | Low | Moderate | Moderate | High |
| Steam Requirement | High | Low | Moderate | Moderate | Low |
| Key Distinguishing Characteristics | Hydrocarbon liquids/ in the raw gas | | Large char recycle | | Large amount/ of sensible heat energy/ in the hot/ raw gas |

TABLE 4

Summary of Performance of R. rubrum strains

| Strain | 25903 | | 9791 | | 11170 | | 19613 | |
|---|---|---|---|---|---|---|---|---|
| Inoculum level g/L | CO Concen. mmol/g hr | $H_2$ Yield % | CO Concen. mmol/g hr | $H_2$ Yield % | CO Concen. mmol/g hr | $H_2$ Yield % | CO Concen. mmol/g hr | $H_2$ Yield % |
| 0.50 | 17.3 | 84 | 16.6 | 74 | 17.3 | 84 | 16.8 | 79 |
| 0.57 | 14.7 | 79 | 16.0 | 85 | 14.1 | 89 | 12.7 | 87 |
| 0.54 | 13.3 | 78 | 13.5 | 77 | 13.9 | 74 | 12.5 | 72 |
| 0.40 | 14.3 | 83 | 16.8 | 72 | 13.9 | 76 | 18.5 | 67 |
| 0.45 | 18.0 | 82 | 17.8 | 78 | 15.8 | 82 | 18.6 | 79 |
| Average | 15.5 | 81 | 16.1 | 77 | 15.0 | 81 | 15.8 | 77 |

TABLE 5

Growth of ERIH2 on Different Sugars, 2 g/L.

| | Day 0 | Day 1 | | Day 2 |
|---|---|---|---|---|
| Sugar | Cells (g/L) | Cells (g/L) | pH | Cells (g/L) |
| Arabinose | 0.054 | 0.230 | 7.15 | 0.188 |
| Fructose | 0.051 | 0.353 | 6.78 | 0.250 |
| Galactose | 0.061 | 0.447 | 6.89 | 0.578 |
| Glucose | 0.046 | 0.438 | 6.83 | 0.257 |
| Mannose | 0.053 | 0.490 | 6.74 | 0.294 |
| Ribose | 0.051 | 0.176 | 6.60 | 0.362 |
| Rhamnose | 0.053 | 0.421 | 7.02 | 0.147 |
| Xylose | 0.050 | 0.513 | 6.65 | 0.249 |

TABLE 6

Evaluation of Corn Steep Liquor as a Growth Co-Substrate for ERIH2
Cell Concentration (g/L)

| | 0 | 3 hr | 5.5 hr | 22 hr | 27 hr |
|---|---|---|---|---|---|
| Glucose (2 g/L) | 0.042 | 0.070 | 0.216 | 0.283 | 0.254 |
| Glucose (2 g/L) + Corn steep Liquor (2 g/L) | | 0.064 | 0.140 | 0.319 | 0.301 0.282 |
| Glucose (4 g/L) | 0.038 | 0.071 | 0.195 | 0.458 | 0.391 |
| Glucose (4 g/L) + Corn steep liquor (2 g/L) | | 0.064 | 0.140 | 0.302 | 0.499 0.466 |

TABLE 7

The Growth of ERIH2 on 5 g/L Glucose and Galactose.

| | Day 0 | Day 1 | | Day 2 | |
|---|---|---|---|---|---|
| Sugar | Cells (g/L) | Cells (g/L) | pH | Cells (g/L) | pH |
| Galactose | 0.062 | 0.185 | 7.21 | 0.774 | 5.87 |
| Glucose | 0.054 | 0.779 | 5.50 | 0.872 | 5.06 |

TABLE 8

Growth and Metabolism of Glucose by ERIH2 (0.75 g/L Glucose)

| Time (hr) | pH | Cells (g/L) | Ammonia (mg/L) | Glucose (g/L) |
|---|---|---|---|---|
| 0 | 6.9 | 0.061 | 131 | 0.73 |
| 4 | 7.0 | 0.163 | 139 | 0.58 |
| 8 | 7.2 | 0.298 | 154 | 0.45 |
| 11.5 | 6.9 | 0.430 | 161 | 0.04 |
| 24 | 6.6 | 0.343 | 170 | 0.04 |

TABLE 9

Growth and Metabolism of Glucose by ERIH2 (1.5 g/L Glucose)

| | pH | | Cells (g/L) | | Ammonia (mg/L) | | Glucose (g/L) | |
|---|---|---|---|---|---|---|---|---|
| Time (hr) | Bot. 1 | Bot. 2 | Bot. 1 | Bot. 2 | Bot. 1 | Bot. 2 | Bot. 1 | Bot. 2 |
| 0 | 6.94 | 6.73 | 0.073 | 0.073 | 124 | 128 | 1.54 | 1.63 |
| 4 | 7.30 | 7.01 | 0.142 | 0.241 | 141 | 163 | 1.40 | 1.34 |
| 8 | 7.11 | 6.57 | 0.258 | 0.718 | 162 | 147 | 1.24 | 0.17 |
| 20 | 6.58 | 6.35 | 0.579 | 0.479 | 171 | 170 | 0.10 | 0.11 |

TABLE 10

Maximizing the Growth of ERIH2 in Various Supplemented Nutrient Media.

| Medium supplement (g/L) | | | |
|---|---|---|---|
| Glucose | Yeast Extract | Tripticase | Cells (g/L) |
| 10 | 15 | 2 | 1.39 |
| 10 | 15 | 5 | 1.50 |

TABLE 10-continued

Maximizing the Growth of ERIH2 in Various Supplemented Nutrient Media.

Medium supplement (g/L)

| Glucose | Yeast Extract | Tripticase | Cells (g/L) |
|---|---|---|---|
| 10 | 15 | 10 | 1.39 |
| 10 | 15 | 15 | 1.43 |
| 10 | 15 | 20 | 1.40 |
| 5 | 5 | 2 | 0.91 |
| 5 | 10 | 2 | 0.97 |
| 5 | 15 | 2 | 1.02 |
| 5 | 20 | 2 | 1.10 |
| 25 | 10 | 5 | 3.50 |
| 25 | 20 | 5 | 4.92 |
| 25 | 20 | 5 | 4.96 |

(with pH adjustment)

TABLE 11

The Comparison of CO Conversion in the CSTR

| Gas Retention Time | CO Conversion (percent) | | |
|---|---|---|---|
| | R. rubrum | Isolate 1 | Isolate 2 |
| 10 min | 20.0 | 52.5 | 75.0 |
| 20 min | 38.0 | 81.3 | 87.0 |
| 30 min | 52.0 | 87.8 | 91.2 |
| 45 min | 65.0 | 91.7 | 93.5 |
| 60 min | 73.8 | 93.0 | 94.7 |
| 90 min | 81.2 | 94.1 | 96.8 |
| Average $H_2$ Yield | 70.0 | 95.0 | 95.0 |

TABLE 12

CO Conversion (percent) in the CSTR with ERIH2

| Agitation | Gas Retention Time | | |
|---|---|---|---|
| (rpm) | 30 minutes | 15 minutes | 10 minutes |
| 200 | 3.50 | 3.5 | 3.65 |
| 300 | 10.48 | 8.01 | 13.56 |
| 400 | 44.37 | 27.52 | 26.67 |
| 500 | 56.0 | 54.01 | 38.68 |
| 600 | 65.15 | 62.26 | 49.21 |
| 700 | 74.65 | 66.31 | 58.65 |
| 800 | 78.43 | 70.92 | 61.58 |
| 900 | 80.96 | 73.75 | 65.6 |
| 1000 | 82.85 | 75.80 | 68.88 |

TABLE 13

Steady State Performance of ERI2 in the CSTR with Cell Recycle
(10 g/L glucose)

| Retention Time (min) | CO Conversion (%) | $H_2$ Yield (%) | Cell Conc. g/L | $H_2$ Productivity (mmole/1 hr) |
|---|---|---|---|---|
| 21.6 | 85.3 | 100.0 | 3.312 | 59.7 |
| 18.4 | 85.0 | 100.0 | 3.064 | 69.2 |
| 16.0 | 83.6 | 90.9 | 3.088 | 71.1 |
| 12.8 | 81.4 | 86.9 | 3.128 | 82.6 |
| 8.1 | 78.5 | 93.3 | 3.0 | 134.0 |

Dilution rate: 0.026 $hr^{-1}$

TABLE 14

Effects of Dilution Rate and Gas Retention Time on the Performance of ERIH2 in the CSTR (2 g/L glucose)

| Liquid Dilution Rate ($hr^{-1}$) | Retention Time (min) | CO Conversion (%) | $H_2$ Yield (%) | Cell g/L |
|---|---|---|---|---|
| 0.007 | 18.9 | 73.6 | 100 | 0.603 |
| 0.014 | 21.2 | 80.4 | 94.5 | 0.686 |
| 0.021 | 19.6 | 83.4 | 93.7 | 0.84 |

TABLE 15

Performance of ERIH2 in the Cocurrent Trickle Bed Reactor

| Gas Flow Rate (ml/min) | Liquid Flow Rate (ml/min) | Gas Retention Time* (min) | CO Conversion (%) | $H_2$ Productivity (mmole/L · hr) |
|---|---|---|---|---|
| 12.50 | 0.28 | 24.00 | 99.40 | 69.0 |
| 19.50 | 0.28 | 15.38 | 90.08 | 97.2 |
| 22.10 | 0.28 | 13.57 | 89.21 | 109.2 |
| 25.10 | 0.28 | 11.95 | 92.13 | 127.8 |
| 28.90 | 0.28 | 10.38 | 90.42 | 144.6 |
| 34.50 | 0.37 | 8.70 | 85.16 | 162.6 |
| 39.63 | 0.37 | 7.57 | 87.80 | 192.6 |
| 42.50 | 0.37 | 7.06 | 86.07 | 202.2 |
| 45.60 | 0.37 | 6.57 | 85.47 | 216.0 |

*based upon fluid volume in reactor

TABLE 16

Calculated Mass transfer Coefficients for ERIH2 in the Presence of Co-Solvents/Surfactants

| Co-Solvents/Surfactant | Concentration (v/v %) | $K_La$ (mmol/ml/min/atm × 1000) | | % Change |
|---|---|---|---|---|
| | | Control | Sample | |
| Glycerol | 10.0 | 2.05 | 1.66 | −16 |
| Dextran | 0.1 | 2.64 | 2.33 | −15 |
| Xantham Gum | 0.025 | 1.70 | 1.67 | −2 |
| FC-40 | 10.0 | 3.02 | 2.84 | −6 |
| Tween 85 | 0.1 | 1.91 | 1.46 | −25 |
| Tergital | 0.1 | 2.08 | 1.99 | −4 |
| Tyloxapol | 0.1 | 3.41 | 15.00 | +340 |
| Nonidet P-40 | 0.1 | 2.54 | 5.25 | +107 |
| Triton N-42 | 0.1 | 2.95 | 1.65 | −44 |
| Triton N-101 | 0.1 | 3.12 | 5.75 | +84 |
| Triton X-15 | 0.1 | 2.40 | 2.27 | −5 |
| Triton X-100 | 0.1 | 2.35 | 7.12 | +203 |
| Span 85 | 0.1 | 2.12 | 1.95 | −8 |
| Tyloxapol + Corn Oil | 0.1 0.2 | 2.77 | 2.61 | −6 |

TABLE 17

Summary of Non-Aqueous Solvent Screening

| Compounds | Addition (Volume %) | $K_La/H$ ($10^3$ mmol/ml/min/atm) | | Increase (percent) |
|---|---|---|---|---|
| | | Control | Amendment | |
| A. Bio-polymers | | | | |
| Dextran | 0.1 | 2.64 | 2.33 | −15 |
| Xanthan gum | 0.025 | 1.70 | 1.67 | −2 |

TABLE 17-continued

Summary of Non-Aqueous Solvent Screening

| Compounds | Addition (Volume %) | $K_La/H$ ($10^3$ mmol/ml/min/atm) Control | Amendment | Increase (percent) |
|---|---|---|---|---|
| B. Bio-surfactants | | | | |
| Triton N-42 | 0.1 | 2.95 | 1.65 | −44 |
| Tween 85 | 0.1 | 1.91 | 1.46 | −25 |
| Triton X-15 | 0.1 | 2.40 | 2.27 | −5 |
| Tergital | 0.1 | 2.08 | 1.99 | −4 |
| Triton N-101 | 0.1 | 3.12 | 5.75 | +84 |
| Nonidet P-40 | 0.1 | 2.54 | 5.25 | +107 |
| Tyloxapol | 0.1 | 3.41 | 15.00 | +340 |
| C. Organic Compounds | | | | |
| Glycerol | 10.0 | 2.05 | 1.66 | −16 |
| FC-40 (perfluoro) | 10.0 | 3.02 | 2.84 | −6 |

TABLE 18

Comparison of CO Consumption by ERIH2 In the Presence of Surfactants

| | CO Consumption (%) | |
|---|---|---|
| | Control | Sample |
| Tyloxapol (0.1%, v/v) | | |
| First Gassing | 100 | 113.24 |
| Regassing | 100 | 129.14 |
| Second Regassing | 100 | 124.18 |
| Brij 96 (0.025%, w/v) | | |
| First Gassing | 100 | 101.70 |
| Regassing | 100 | 24.65 |
| (0.05%, w/v) | | |
| First Gassing | 100 | 110.08 |
| Regassing | 100 | 33.62 |
| (0.0107%, w/v) | | |
| First Gassing | 100 | 109.61 |
| Regassing | 100 | 24.91 |
| Nonyl Alcohol (0.1%, v/v) | 100 | 98.93 |
| Oleyl Alcohol (0.1%, v/v) | 100 | 95.02 |
| Propylene Glycol (0.1%, v/v) | 100 | 98.33 |
| Cyclohexane (0.1%, v/v) | 100 | 97.76 |

TABLE 19

Comparison of Calculated Specific CO Uptake Rates of R. rubrum and ERIH2

| | q, mmol/hr · gcells | |
|---|---|---|
| $P^L_{CO}$, atm | R. rubrum | ERIH2 |
| 0.1 | 8.73 | 181.39 |
| 0.2 | 10.92 | 191.56 |
| 0.4 | 9.58 | 139.13 |
| 0.6 | 7.69 | 102.86 |
| 0.8 | 6.28 | 80.65 |

TABLE 20

Typical Operating Conditions of Various $CO_2$ Removal Processes

| Process | Solution Composition | Net Loading (scf/gal) | $CO_2$ in Feed Gas $CO_2$ by Volume | Operating Conditions Pressure (lb./in$^2$ gauge) | Temperature (°F.) | Utilities Heat | Power |
|---|---|---|---|---|---|---|---|
| Catacarb | Varies | 3–5.5 | 2–27 | 100–1200 | 100–260 | Low | Medium |
| Benfield | $K_2CO_3$ + promotor | 3–5.5 | 2–27 | 100–2000 | 100–260 | Low | Medium |
| Vetrocoke | Varies | Not known | 2–27 | 100–1200 | 120–212 | Low | Medium |
| Conventional MEA | 15–20% | 2.5–3.5 | 0.5–10.0 | 25–950 | 80–130 | High | High |
| High-loaded MEA | 30–40% | 7 | 15–25 | 400–900 | 130–160 | Medium | Medium |
| Conventional DEA | 20–25% | 2–3 | 0.5–0.8 | 175–500 | 80–130 | High | High |
| High-loaded DEA | 25–27% | 5–5.4 | 2.0–20 | 175–950 | 80–130 | Medium | Medium |
| SNPA:DEA | 25–30% | 5.5–6.2 | 2.0–30 | 200–2000 | 80–130 | Medium | Medium |
| DGA | 65–70% | 5–7 | 5.0–20 | 150–950 | 80–130 | Medium | Medium |
| Sulfinol | Varies | 8–16 | 2.0–30 | 300–1000 | 100–160 | Medium | Low |
| Selexol | DMPEG | 11–15 | 2.0–45 | 500–1400 | 100–160 | Low | Low–medium |
| Rectisol | Methanol | 5–20 | 2.0–35 | 300–1200 | −5 to −100 | Low | Medium |
| Purisol | NMP | 5–10 | 5.0–35 | 450–1200 | 40–105 | Low | Medium |

TABLE 20-continued

Typical Operating Conditions of Various $CO_2$ Removal Processes

| Process | Solution Composition | Net Loading (scf/gal) | $CO_2$ in Feed Gas $CO_2$ by Volume | Operating Conditions Pressure (lb./in$^2$ gauge) | Temperature (°F.) | Utilities Heat | Power |
|---|---|---|---|---|---|---|---|
| Fluor | Propylene carbonate | | 5.0–53 | | | | |

*/Depends on solubility and recompression of flash gas
Note:
NMP: n-methyl 2-pyrrolidone
DMPEG: dimethyl ether of polyethylene glycol
Sulfinol solvent: sulfolane, di-isopropanol amine

TABLE 21

Modified Medium for *R. rubrum*
(without YE, NH3 and Trypticase)

| | | | |
|---|---|---|---|
| 1. | Salt C | 80.0 | ml |
| 2. | PFN trace | 1.0 | ml |
| 3. | Vitamin | 5.0 | ml |
| 4. | Cysteine HCL | 0.5 | g |
| 5. | $CaCl_2 2H_2O$ | 0.06 | g |
| 6. | $NaHCO_3$ | 2.0 | g |
| 7. | Distilled water | 920.0 | ml |
| 8. | Adjust pH to 7.0 under 20% $CO_2$ and 80% $N_2$. | | |
| 9. | Bubbled under 20% $CO_2$ and 80% $N_2$ for 30 min. | | |
| 10. | Tubed anaerobically and autoclaved for 15 min. | | |
| 11. | Trypticase, glucose or $NH_3$ is added as required. | | |

TABLE 22

Medium for ERIH2

| | | | |
|---|---|---|---|
| 1. | Salt C | 80.0 | ml |
| 2. | Yeast extract | 1.0 | g |
| 3. | Trypticase | 1.0 | g |
| 4. | PFN trace | 3.0 | ml |
| 5. | Vitamin | 10.0 | ml |
| 6. | Glucose | 2.0 | g |
| 7. | $CaCl_2 2H_2O$ | 0.06 | g |
| 8. | NaHCO3 | 2.0 | g |
| 9. | Resazurin (0.01%) | 1.0 | ml |
| 10. | Distilled water | 920.0 | ml |
| 11. | Adjust pH to 6.6 under 20% $CO_2$ and 80% $N_2$. | | |
| 12. | Bubbled under 20% $CO_2$ and 80% $N_2$ for 20 min. | | |
| 13. | Tubed anaerobically and autoclaved for 15 min. | | |

TABLE 23

Medium for *R. rubrum* (ATCC)

| | | | |
|---|---|---|---|
| 1. | PFN salt | 50.0 | ml |
| 2. | PFN trace | 1.0 | ml |
| 3. | B-vitamin | 5.0 | ml |
| 4. | $NH_4Cl$ | 2.7 | g |
| 5. | Yeast Extract | 1.0 | g |
| 6. | Distilled water | 944.0 | ml |
| 7. | Boiled under 80% $N_2$ and 20% $CO_2$. | | |
| 8. | Cooled and add 4.0 g $NaHCO_3$. | | |
| 9. | Tubed under 80% $N_2$ and 20% $CO_2$. | | |
| 10. | Autoclaved for 15 min. | | |

We claim:

1. A biologically pure culture of the microorganism *Bacillus smithii* ERIH2 having all of the identifying characteristics of ATCC No. 55404.

2. The culture according to claim 1, having the ability to produce hydrogen under anaerobic conditions upon fermentation in an aqueous nutrient medium containing synthesis gas as a substrate.

3. The culture according to claim 2 wherein said substrate is selected from the group consisting essentially of CO, $CO_2$, and $H_2$.

4. The culture according to claim 1, having the ability to produce hydrogen under anaerobic conditions in an aqueous nutrient medium comprising sources of carbon.

5. The culture according to claim 4 wherein said carbon source is a sugar.

6. The culture according to claim 1, said culture being rod-shaped, non-sporeforming, gram-positive, and facultatively anaerobic.

7. The culture according to claim 1, having the ability to ferment glucose under anaerobic conditions and produce formate, acetate and lactate.

* * * * *

UNITED STATES PATENT AND TRADEMARK OFFICE
CERTIFICATE OF CORRECTION

PATENT NO. : 5,821,111
DATED : October 13, 1998
INVENTOR(S) : James L. Grady et al.

It is certified that error appears in the above-identified patent and that said Letters Patent is hereby corrected as shown below:

<u>Title page,</u>
Item [75], Inventors, replace "Grady" with -- Gaddy --.

Signed and Sealed this

Thirteenth Day of May, 2003

JAMES E. ROGAN
*Director of the United States Patent and Trademark Office*